United States Patent
Mautino et al.

(10) Patent No.: US 9,732,035 B2
(45) Date of Patent: Aug. 15, 2017

(54) SALTS AND PRODRUGS OF 1-METHYL-D-TRYPTOPHAN

(71) Applicant: NewLink Genetics, Corp., Ames, IA (US)

(72) Inventors: Mario Mautino, Ankeny, IA (US); Sanjeev Kumar, Ames, IA (US); Firoz Jaipuri, Ames, IA (US); Jesse Waldo, Huxley, IA (US); Hima Potturi, Ames, IA (US); Hong Zhuang, Ames, IA (US)

(73) Assignee: NEWLINK GENETICS CORPORATION, Ames, IA (US)

( * ) Notice: Subject to any disclaimer, the term of this patent is extended or adjusted under 35 U.S.C. 154(b) by 0 days.

(21) Appl. No.: 15/171,031

(22) Filed: Jun. 2, 2016

(65) Prior Publication Data

US 2017/0022157 A1   Jan. 26, 2017

Related U.S. Application Data

(60) Provisional application No. 62/196,671, filed on Jul. 24, 2015, provisional application No. 62/305,748, filed on Mar. 9, 2016.

(51) Int. Cl.

| | | |
|---|---|---|
| A61K 31/675 | (2006.01) | |
| A61K 31/405 | (2006.01) | |
| C07F 9/02 | (2006.01) | |
| C07D 209/20 | (2006.01) | |
| C07F 9/6574 | (2006.01) | |
| C07D 405/12 | (2006.01) | |
| C07D 401/12 | (2006.01) | |
| C07C 309/04 | (2006.01) | |
| C07C 309/20 | (2006.01) | |

(52) U.S. Cl.
CPC .......... *C07D 209/20* (2013.01); *C07C 309/04* (2013.01); *C07C 309/20* (2013.01); *C07D 401/12* (2013.01); *C07D 405/12* (2013.01); *C07F 9/65742* (2013.01)

(58) Field of Classification Search
CPC .... C07D 209/08; C07D 209/20; C07F 9/6561
USPC .................. 514/80, 415; 558/70
See application file for complete search history.

(56) References Cited

U.S. PATENT DOCUMENTS

| | | |
|---|---|---|
| 3,825,559 A | 7/1974 | Tazuke et al. |
| 4,072,691 A | 2/1978 | Chibata et al. |
| 5,185,157 A | 2/1993 | Caston |
| 7,598,287 B2 | 10/2009 | Munn et al. |
| 7,705,022 B2 | 4/2010 | Prendergast et al. |
| 7,714,139 B2 | 5/2010 | Prendergast et al. |
| 8,476,454 B2 | 7/2013 | Prendergast et al. |
| 8,846,726 B2 | 9/2014 | Combs et al. |
| 8,951,536 B2 | 2/2015 | Combs et al. |
| 8,993,605 B2 | 3/2015 | Combs et al. |

| | | |
|---|---|---|
| 2005/0032804 A1 | 2/2005 | Cypes et al. |
| 2013/0060048 A1 | 3/2013 | Tam et al. |
| 2014/0377307 A1 | 12/2014 | Munn et al. |

FOREIGN PATENT DOCUMENTS

| | | |
|---|---|---|
| WO | WO 2008/115804 A1 | 9/2008 |
| WO | WO 2009/073620 A2 | 6/2009 |
| WO | WO 2009/132238 A2 | 10/2009 |
| WO | WO 2011/056652 A1 | 5/2011 |
| WO | WO 2012/142237 A1 | 10/2012 |
| WO | WO 2014/081689 A1 | 5/2014 |
| WO | WO 2014/141110 A2 | 9/2014 |
| WO | WO 2014/150646 A1 | 9/2014 |
| WO | WO 2014/150677 A1 | 9/2014 |
| WO | WO 2014/159248 A1 | 10/2014 |
| WO | WO 2014/186035 A1 | 11/2014 |
| WO | WO 2015/002918 A1 | 1/2015 |
| WO | WO 2015/006520 A1 | 1/2015 |
| WO | WO 2017/019175 A1 | 2/2017 |

OTHER PUBLICATIONS

Banerjee, T., et al. "A key in vivo antitumor mechanism of action of natural product-based brassinins is inhibition of indoleamine 2, 3-dioxygenase." Oncogene (2008); 27.20: 2851-2857.

Fallarino, Francesca, et al. "The combined effects of tryptophan starvation and tryptophan catabolites down-regulate T cell receptor ζ-chain and induce a regulatory phenotype in naive T cells." The Journal of Immunology (2006); 176.11: 6752-6761.

Holmgaard, Rikke B., et al. "Indoleamine 2, 3-dioxygenase is a critical resistance mechanism in antitumor T cell immunotherapy targeting CTLA-4." The Journal of Experimental Medicine (2013); 210.7: 1389-1402.

Hou, De-Yan, et al. "Inhibition of indoleamine 2, 3-dioxygenase in dendritic cells by stereoisomers of 1-methyl-tryptophan correlates with antitumor responses." Cancer Research (2007); 67.2: 792-801.

Kumar, Sanjeev, et al. "Structure based development of phenylimidazole-derived inhibitors of indoleamine 2, 3-dioxygenase." Journal of Medicinal Chemistry (2008); 51.16: 4968-4977.

Li, Lingqian, et al. "Altered tryptophan metabolism as a paradigm for good and bad aspects of immune privilege in chronic inflammatory diseases." Frontiers in Immunology (2012); 3(109): 1-14.

McGaha, Tracy L., et al. "Amino acid catabolism: a pivotal regulator of innate and adaptive immunity." Immunological Reviews (2012); 249.1: 135-157.

(Continued)

*Primary Examiner* — Raymond Henley, III

(74) *Attorney, Agent, or Firm* — Cooley LLP

(57) ABSTRACT

Presently provided are indoximod prodrug and salt compounds and pharmaceutical compositions comprising salts and prodrugs of indoximod, that produce enhanced plasma concentration and exposure to indoximod compared to direct administration of indoximod, in patients in need of treatment of immunosuppression mediated by the indoleamine-2,3-dioxygenase pathway, such as patients with cancer or chronic infectious diseases.

30 Claims, 6 Drawing Sheets

(56) References Cited

OTHER PUBLICATIONS

Metz, Richard, et al. "IDO inhibits a tryptophan sufficiency signal that stimulates mTOR: a novel IDO effector pathway targeted by D-1-methyl-tryptophan." OncoImmunology (2012); 1.9: 1460-1468.
Muller, Alexander J., et al. "Inhibition of indoleamine 2, 3-dioxygenase, an immunoregulatory target of the cancer suppression gene Bin1, potentiates cancer chemotherapy." Nature Medicine (2005); 11.3: 312-319.
Munn, David H., et al. "GCN2 kinase in T cells mediates proliferative arrest and anergy induction in response to indoleamine 2, 3-dioxygenase." Immunity (2005); 22.5: 633-642.
Munn, David H., et al. "Prevention of allogeneic fetal rejection by tryptophan catabolism." Science (1998); 281.5380: 1191-1193.
Peterson, A. C., et al. "Evaluation of functionalized tryptophan derivatives and related compounds as competitive inhibitors of indoleamine 2, 3-dioxygenase." Med Chem Res (1994); 3: 531-544.
Sharma, Madhav D., et al. "Indoleamine 2, 3-dioxygenase controls conversion of Foxp3+ Tregs to TH17-like cells in tumor-draining lymph nodes." Blood (2009); 113.24: 6102-6111.
Sharma, Madhav D., et al. "Plasmacytoid dendritic cells from mouse tumor-draining lymph nodes directly activate mature Tregs via indoleamine 2, 3-dioxygenase." The Journal of Clinical Investigation (2007); 117.9: 2570-2582.
PCT/US2016/035391, International Search Report and Written Opinion mailed Nov. 16, 2016, 11 pages.

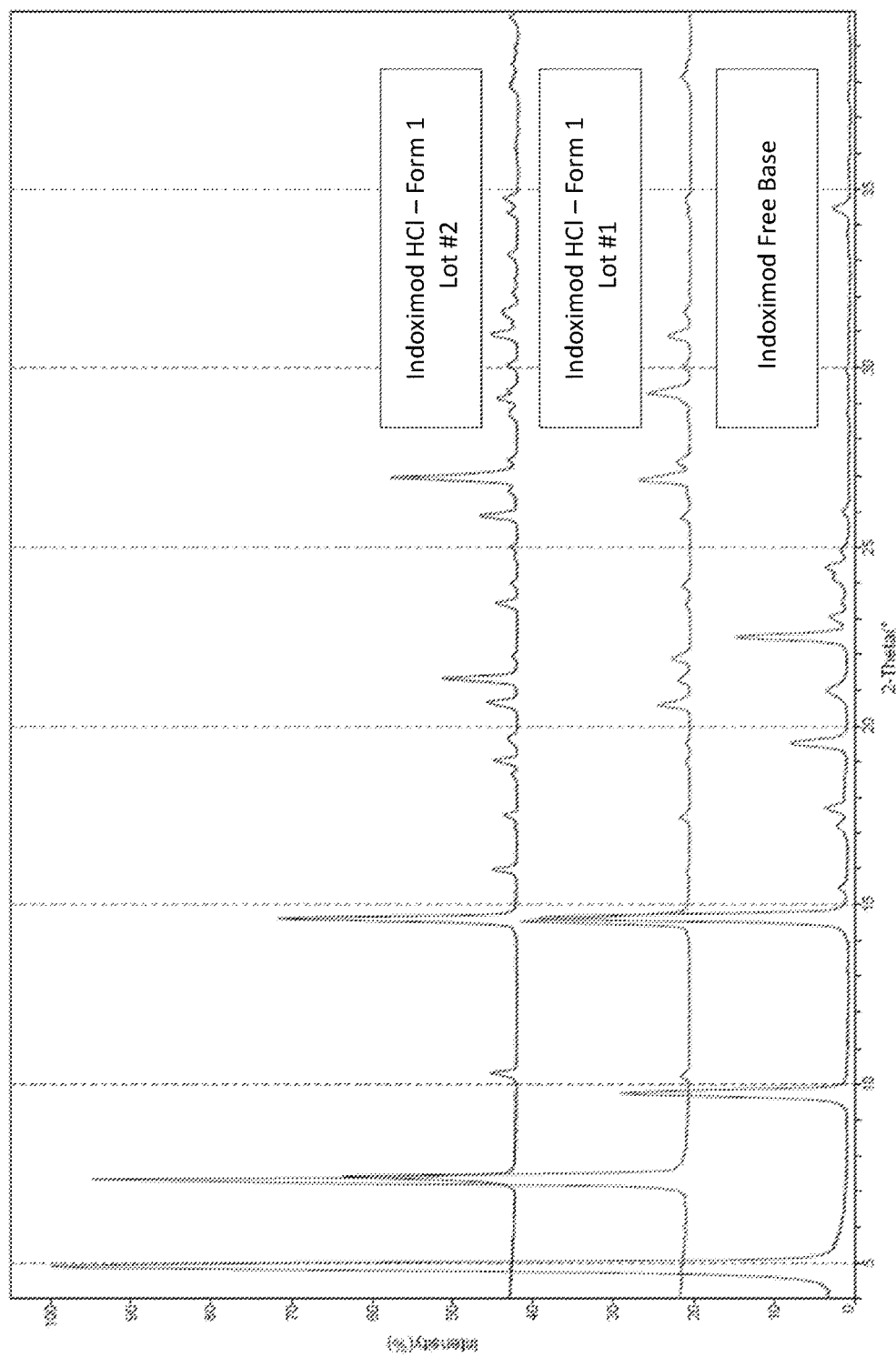
Figure 1: XRPD of indoximod and indoximod HCl

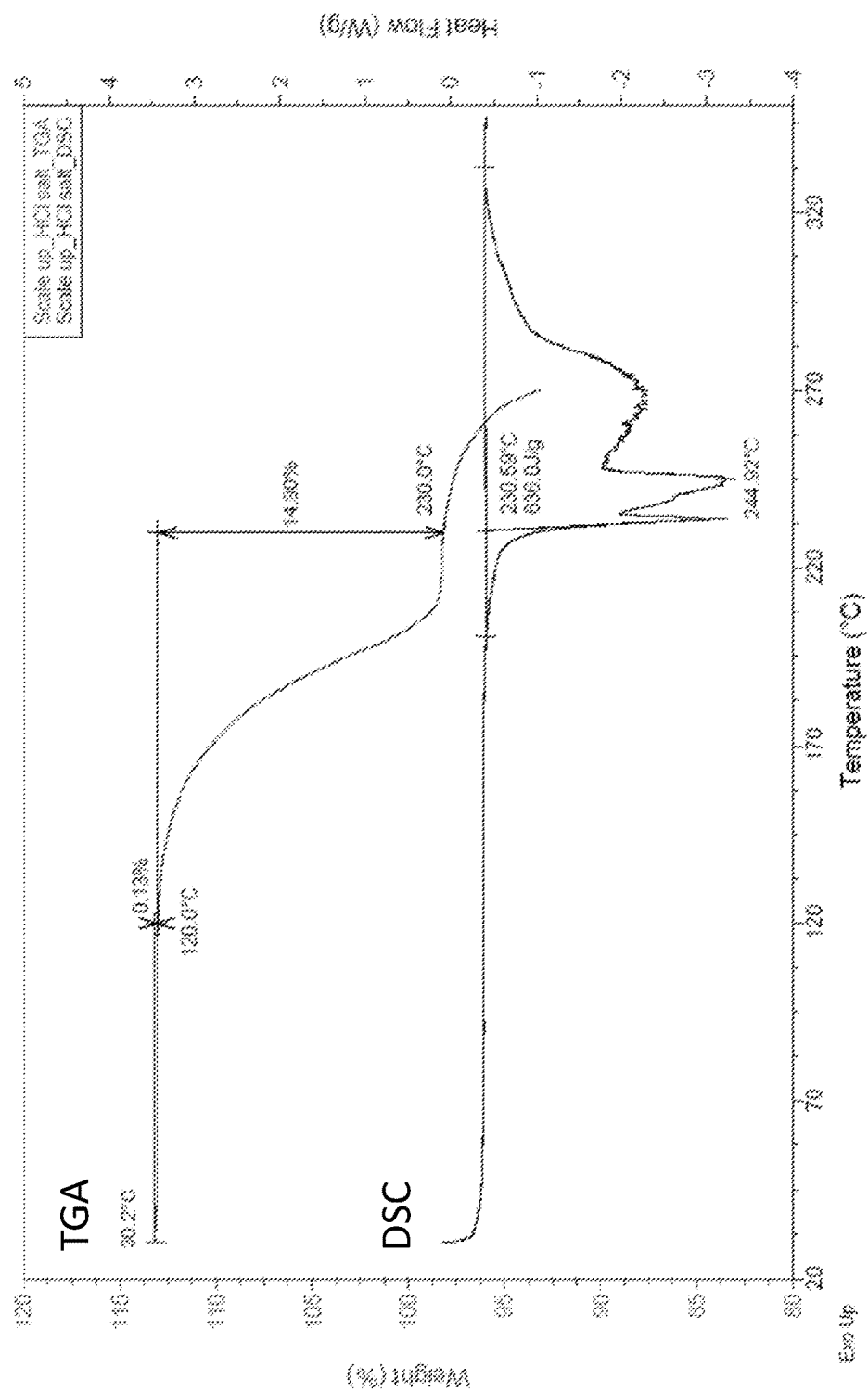
Figure 2: TGA and DSC analysis of indoximod HCl

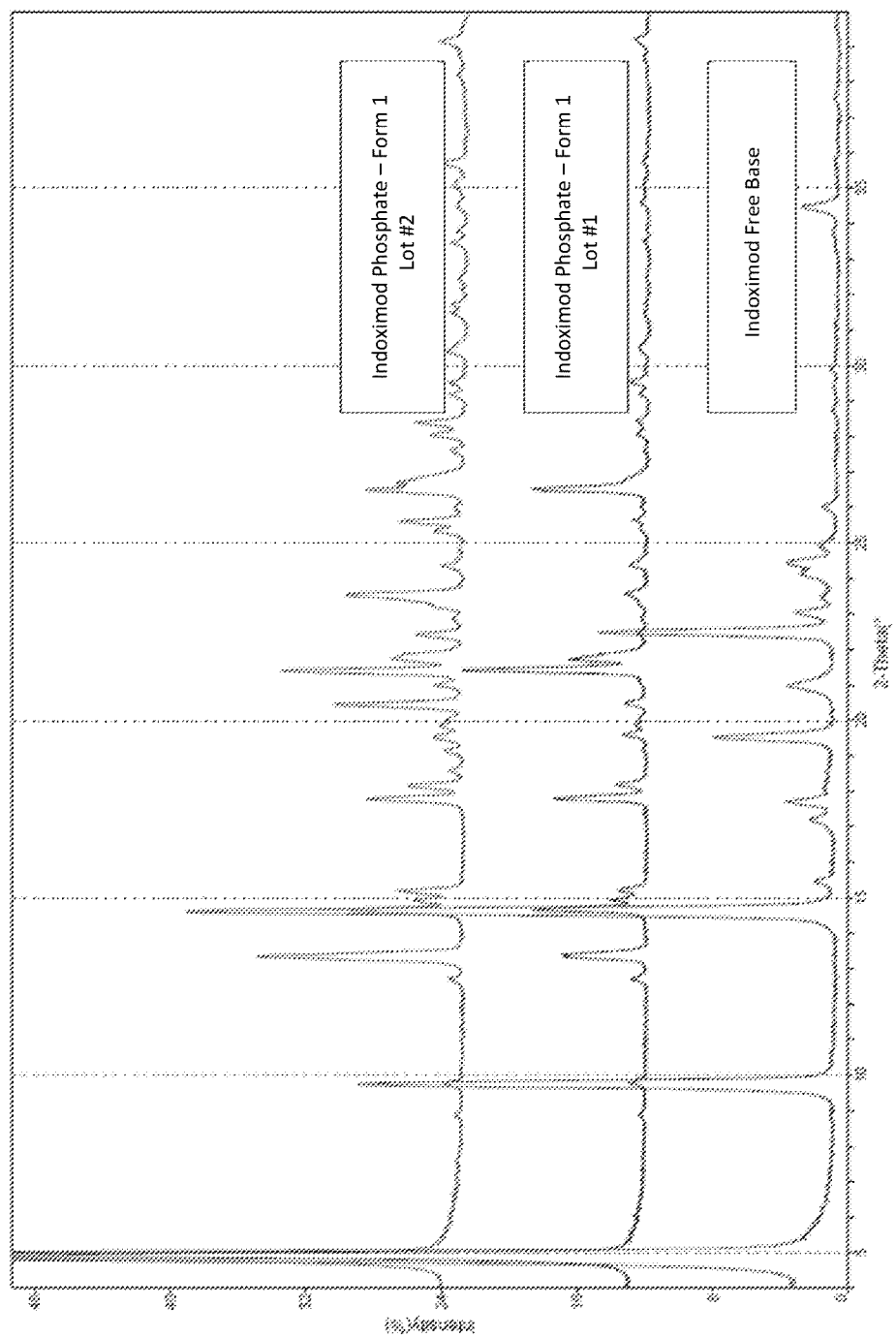
Figure 3: XRPD of indoximod and indoximod phosphate

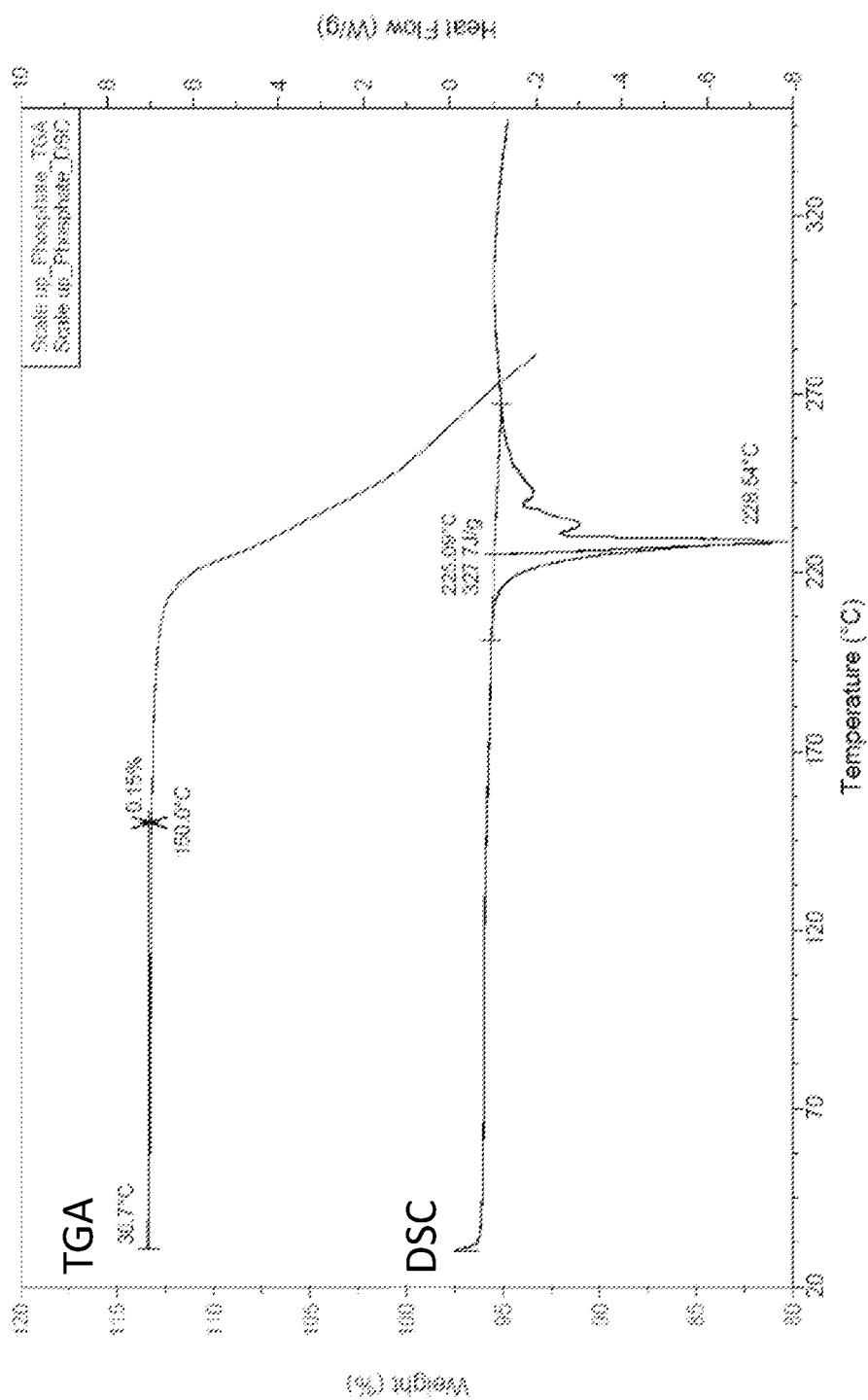
Figure 4: TGA and DSC analysis of indoximod phosphate

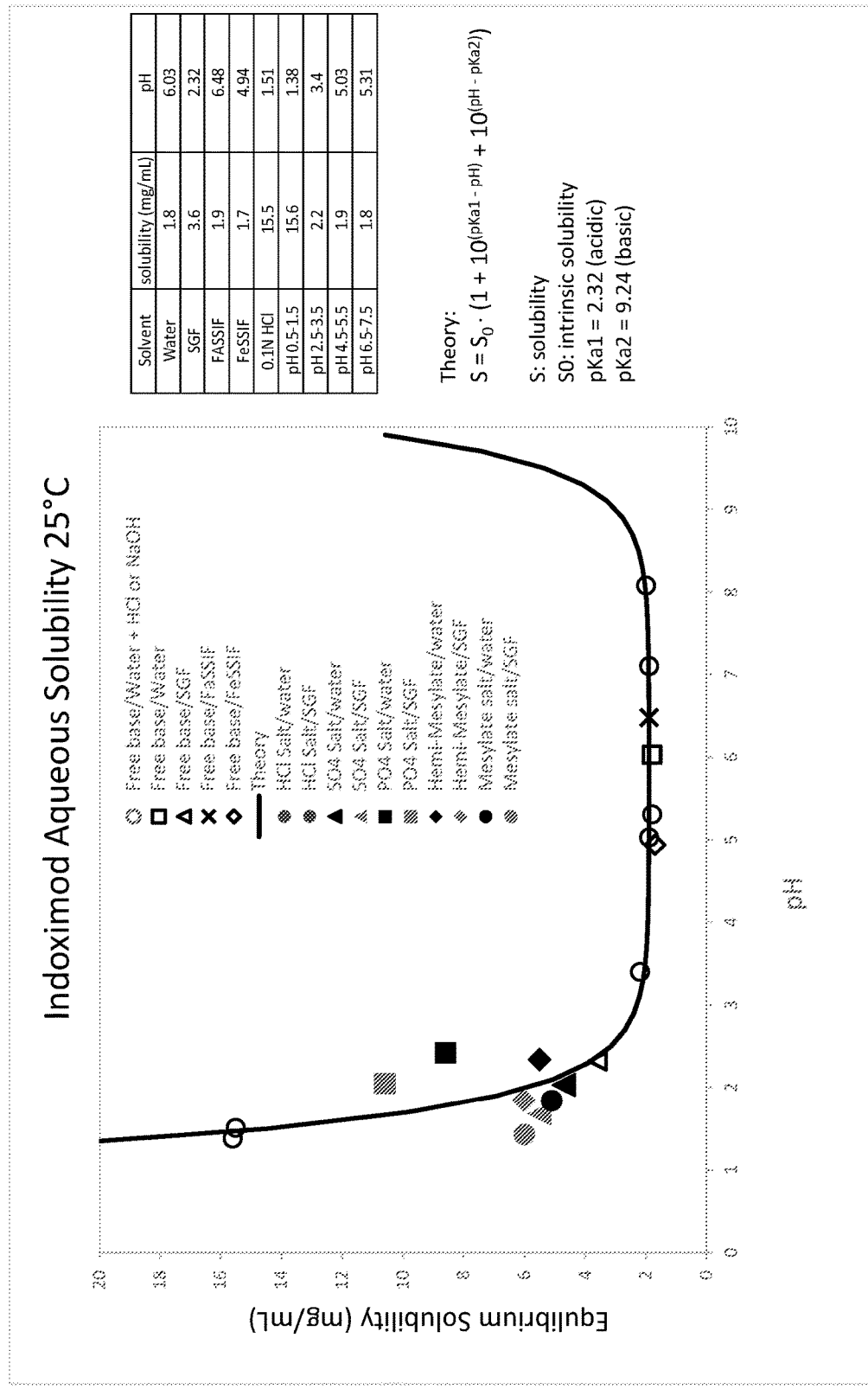
Figure 5: Solubility of indoximod and its salts in different solvents

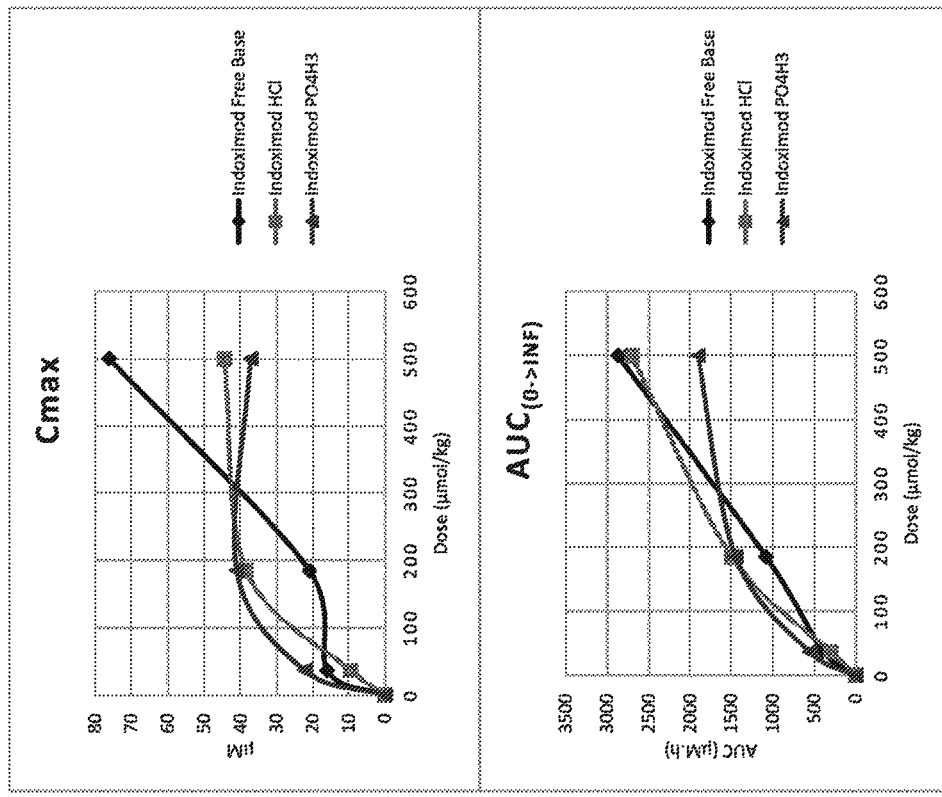
Figure 6: Dose dependency of Cmax and AUC for indoximod and its salts rats after oral dosing in capsule form

SALTS AND PRODRUGS OF 1-METHYL-D-TRYPTOPHAN

CROSS-REFERENCE TO RELATED APPLICATIONS

This application claims priority to U.S. Provisional Application Ser. No. 62/196,671 filed on Jul. 24, 2015 and U.S. Provisional Application Ser. No. 62/305,748 filed on Mar. 9, 2016, the entire contents of which are hereby incorporated by reference in their entirety.

BACKGROUND OF THE INVENTION

Field of the Invention

The present disclosure is related to compounds for inhibition of indoleamine-2,3-dioxygenase pathway, in particular salts and prodrugs of indoximod with enhanced pharmacokinetic properties relative to indoximod Summary of Related Art Tryptophan degradation into kynurenine is mediated by indoleamine-2,3-dioxygenase (IDO1) expressed by plasmacytoid dendritic cells, placental, epithelial and tumor cells and by tryptophan-2,3-dioxygenase (TDO2) expressed mainly by the liver and tumor cells.

IDO1 plays an important role in the regulation of immune responses by triggering anergy on reactive effector T cells and by modulating differentiation and activation of regulatory T cells (Tregs). From a more general viewpoint, the IDO enzyme is involved in pathway that comprises all proteins that directly or indirectly contribute to modulate the immunosuppressive functions dependent on IDO activity, including proteins that mediate induction of IDO expression, activation of enzymatic activity by reductases, post-translational modifications that regulate activity, protein degradation, and the interpretation and transmission of the signals elicited by low concentrations of Trp and the presence of Trp catabolites [collectively known as kynurenines (Kyns)] including catabolic stress sensors integrated into the General Control Nonrepressed-2 (GCN2) pathway, the Aryl Hydrocarbon Receptor (AhR) pathway, and the mammalian Target Of Rapamycin (mTOR) pathways. This concept of integrated downstream regulatory pathways with IDO at the center has emerged from studies on multiple model systems by many research groups and this notion may be critically important for understanding how the IDO pathway is induced, how IDO exerts downstream effects, and the mechanism of action of IDO pathway inhibitors that target IDO directly or target other components of the IDO pathway [1,2].

Therefore, direct pharmacological inhibition of IDO1 enzymatic activity or inhibition of the upstream factors that activate IDO1 enzyme or inhibition of the downstream effects of IDO1 enzymatic activity should stimulate an immune response by multiple mechanisms that may involve preventing anergy of effector T cells, reactivating anergic effector T cells, preventing the activation of regulatory T cells, promoting phenotypic conversion of Tregs to pro-inflamatory TH17 cells and promoting phenotypic reprogramming of immunosuppressive dendritic cells into immunostimulatory dendritic cells.

For these reasons, numerous enzymatic inhibitors of IDO have been described and are being developed to treat or prevent IDO related diseases such as cancer and infectious diseases. Numerous molecules that inhibit IDO enzymatic activity either as competitive or non-competitive inhibitors have been described in the literature, for example in patent applications WO2012142237, WO2014159248, WO2011056652, WO2009132238, WO2009073620, WO2008115804, WO 2014150646, WO 2014150677, WO 2015002918, WO 2015006520, WO 2014141110, WO 2014/186035, WO 2014/081689, U.S. Pat. No. 7,714,139, U.S. Pat. No. 8,476,454, U.S. Pat. No. 7,705,022, U.S. Pat. No. 8,993,605, U.S. Pat. No. 8,846,726, U.S. Pat. No. 8,951,536, U.S. Pat. No. 7,598,287.

One of the first IDO pathway inhibitors studied in preclinical models has been 1-methyl-DL-tryptophan (1mT), a racemic mixture of enantiomers, which was shown to mediate immune dependent rejection of allogeneic fetuses in mice [3] and immune dependent enhancement of antitumor activity of chemotherapy and radiotherapy [4]. Each one of these enantiomers shows different biological properties. 1-methyl-L-tryptophan (L1mT) has been shown to inhibit IDO1 enzymatic activity (Ki=34 µM, [5]) in cell-free assays using purified recombinant IDO1 enzyme, and in tumor cells treated with INFγ or in tumor cell lines transfected with expression vectors that encode IDO1 under the control of an heterologous promoter, while the D isomer (indoximod) does not inhibit enzymatic activity in these type of assays [6]. Nonetheless, both isomers are capable of restoring T cell proliferation in an MLR assay with IDO+ dendritic cells as the stimulator cells, or in syngeneic antigen-dependent T cell proliferation assays using IDO+ DCs isolated from tumor draining lymph nodes [6]. In this type of assay, where IDO+ DCs are present, T cells do not proliferate. However, inhibition of the IDO pathway by these inhibitors restores the proliferative capacity of T cells. Interestingly, both isomers show different potency in this assay, with indoximod being more potent (EC50=30 µM) than L1mT (EC50=80-100 µM) or the racemic mixture (80-100 µM) [6]. Moreover, despite the fact that indoximod does not show inhibition of enzymatic activity in other types of assays, it shows inhibition of enzymatic activity in this co-culture assay, as seen by reduced Trp degradation and Kyn synthesis.

A somewhat puzzling issue has been the fact that indoximod does not show inhibition of IDO1 enzymatic activity in vitro, but somehow mimics the biological consequences of IDO1 inhibition in vivo or in cell based assays. Experimental evidence from a number of research laboratories points to the conclusion that indoximod is participating in the inhibition of the IDO1 pathway. Several possible mechanisms by which this could be taking place are: 1) inhibition of isoforms of IDO1, 2) inhibition of IDO2, 3) alternative formation of indoximod derived metabolites, 4) racemization of indoximod into L1mT, 5) inhibition of Trp transport, 6) inhibition of the GCN2 pathway by formation of indoximod-tRNA complexes, 7) inhibition of enzymes involved in Trp sensing such as WARS1 or WARS2, 8) alteration of autophagy under conditions of amino acid deprivation induced stress or 9) bypassing mechanisms that inactivate mTOR under conditions of amino acid deficiency [7]. These mechanisms are not necessarily mutually exclusive, and so far are compatible with the current experimental data. Further investigations are needed to elucidate which of these biochemical mechanisms is responsible for the biological activity of indoximod.

The biological activity of indoximod to relieve immunosuppression in vivo and in vitro is supported by studies performed in several laboratories in murine preclinical models. Indoximod has demonstrated activity in the following biological assays:

1. In combination with chemotherapy, indoximod demonstrates antitumor effects in animal models of ectopic melanoma, colon and lung tumors, and in orthotopic and autochtonous breast tumor models. The antitumor effect of indoximod is lost in nude and IDO1-KO mice [6].
2. indoximod can prevent the process of activation of mature Tregs in vivo, and facilitates the in vitro and in vivo trans-differentiation of Tregs into pro-inflamatory TH17-like T cells [8, 9].
3. In tumor vaccination protocols, the combination of two different antitumor vaccines with indoximod was effective in converting a higher proportion of Treg cells into TH17-like T cells, with concomitant antitumor effect [9].
4. In melanoma models, combination of anti-CTLA4 (ipilimumab) and indoximod, results in synergistic antitumor effect [10].
5. In vivo, indoximod was more efficacious as an anticancer agent in chemo-immunotherapy regimens using cyclophosphamide, paclitaxel, or gemcitabine, when tested in mouse models of transplantable melanoma and transplantable (4T1) and autochthonous (mmTV-neu) breast cancer [6].
6. IDO1 has also been implicated in the differentiation of nave CD4 T cells into Tregs, by the combined effect of Trp deprivation and the presence of Trp catabolites, through a mechanism that depends on GCN2 [11, 12]. This conversion is interrupted in vivo in the presence of indoximod.
7. Similarly, IDO+ pDCs have also been implicated in the activation of mature Tregs in vivo, which also required an intact GCN2 pathway in the Treg population. This phenomenom could be prevented by excess Trp or by indoximod [8].
8. In addition to preventing the activation of mature Treg cells, indoximod can mediate the conversion of suppressive FoxP3$^+$ Tregs into pro-inflamatory TH17 cells in vitro and in vivo. This conversion of Tregs into TH17 cells required the presence of antigen or engagement of B7 in the pDCs, and the presence of functional IDO1 and GCN2 genes in the pDCs. Indoximod was able to mimic the phenotypic consequences of IDO1 or GCN2 gene ablation [9], therefore supporting its role in inhibition of the IDO pathway.
9. Antitumor and immunologic studies using IDO1-KO mice or pDCs derived from IDO1-KO mice demonstrated that the beneficial effects of indoximod are lost in the context of a genetic background lacking a functional IDO1 [6]. In particular, it was observed that IDO1-KO mice develop tumors, which are not sensitive to treatment with indoximod in combination with chemotherapy. Additionally, pDCs derived from tumor draining lymph nodes of IDO1-KO mice are able to stimulate the proliferation of T cells in culture, to the same extent as IDO(−) APCs. These observations were interpreted as a genetic validation of IDO1 as the pharmacologic target of indoximod. However, this could also be interpreted as indoximod blocking some other point of action within the IDO pathway.
10. The antitumor and immunologic observations made by administration of indoximod were also reproduced by administration of other well documented IDO1 inhibitors (i.e. molecules that inhibit the enzymatic activity of IDO1 in vitro and in cell based assays) such as 5-Br-brassinin, menadione, methyl-thiohydantoin-tryptophan, and analogs of phenylimidazole (unpublished), thereby validating the IDO1 pathway as the pharmacologic target [4, 13, 14].
11. In preclinical animal models, the in vivo pharmacodynamic effects of indoximod are seen mainly in tumor draining lymph nodes, where the effect is seen as activation and proliferation of CD8α+ cells, reduction in the number of FoxP3+ Tregs, reprogramming of Tregs (CD40L$^-$) to immunostimulatory T cells (CD40L$^+$) and reprogramming of IDO$^+$ antigen presenting cells from CD11c$^+$/CD80/86$^-$ to CD80/86$^+$ phenotype.

For these reasons, indoximod is being investigated in human clinical trials for cancer indications. Indoximod is being studied in several cancer indications in combination with different chemotherapeutic and biological immunotherapeutic agents, such as docetaxel, paclitaxel, gemcitabine, Nab-paclitaxel, temozolomide, ipilimumab, sipuleucel-T, or vaccines.

Indoximod is orally bioavailable with a favorable pharmacokinetic (PK) profile (Tmax: ~3 h; half-life: ~10 h) and an excellent safety profile. Pharmacokinetic studies in patients have demonstrated that indoximod shows a linear PK profile at doses of up to 800 mg/dose, with maximum plasma concentration (Cmax) of 15 µM and drug exposure (AUC$_{(0-last)}$) levels of ~100 µM·h. However, increasing doses above 800 mg/dose up to 2000 mg/dose, does not result in a linear or proportional increase in Cmax or drug exposure, thus potentially limiting the therapeutic activity of this investigational drug.

Mixed-lymphocyte response (MLR) T cell proliferation assay show that T cells that are in an IDO$^+$ environment restore ~50% of their proliferative capacity at concentrations of indoximod higher than 30 µM. Murine antitumor experiments show that biological effects of indoximod are observed when mice are dosed with indoximod in the drinking water at 3 mg/mL (~500 mg/kg/day), or dosed orally at 200 mg/kg bid, which results in Cmax higher than 20 µM and exposures greater than 300 µM·h. For these reasons, it is desirable to increase the Cmax and exposure to indoximod in human clinical trials so they may reach the levels necessary for therapeutic activity. However, the non-linear pharmacokinetic profile of this drug makes it unlikely that this could be solved by increasing the dose given to patients.

For the above mentioned reasons we investigated whether different formulation of indoximod such as spray dry dispersions or salts or indoximod prodrugs in different salt forms would increase solubility and absorption rate or reduce blood clearance to levels that increase the maximum concentration and exposure to indoximod. Moreover, we looked for prodrugs and its salts that could result in increases parameters of exposure when dosed orally and in pill (capsule or tablet) dosage formulation.

The results of these investigations showed that a few selected prodrugs resulted in increases in parameters of exposure; and that increases in in vitro solubility and in vivo exposure could be achieved by a few salts of indoximod upon oral administration.

SUMMARY OF THE INVENTION

In one aspect the invention describes compounds and pharmaceutical compositions comprising compounds according to Formula 1a and 1b

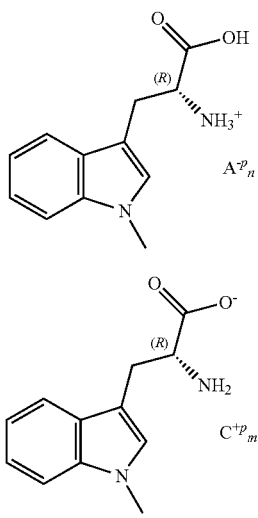

Formula 1a

Formula 1b

Wherein $A^{-p}{}_n$ is an inorganic or organic anion and $C^{+p}{}_m$ is an inorganic cation as defined herein.

In another aspect, the invention comprises compounds and pharmaceutical compositions comprising compounds according to formula (2)

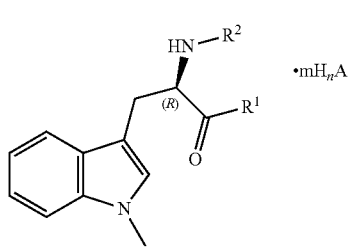

Formula 2

Where $R^1$, $R^2$ and $mH_nA$ are defined herein

In another aspect, the present disclosure provides a) pharmaceutical compositions comprising compounds of formula 1a, 1b or formula 2, that result in elevated exposure and maximum concentration to 1-methyl-D-tryptophan (indoximod) after oral administration to a subject, compared to administration of an equivalent molar dose of indoximod formulated as a free base.

b) methods of use of compositions comprising compounds of formulas 1a, 1b or 2, to modulate the activity of indoleamine-2,3-dioxygenase pathway in a subject in need thereof, comprising the oral administration of sufficient amounts such compositions to such subject in an appropriate pharmaceutical form or vehicle.

c) methods of use of compositions comprising compounds of formulas 1a, 1b or 2, for the treatment of cancer in a subject in need thereof, comprising the oral administration of sufficient amounts of such compositions to such subject in an appropriate pharmaceutical form or vehicle.

d) methods of use of compositions comprising compounds of formulas 1a, 1b or 2, to treat tumor-specific immunosuppression associated with cancer, in a subject in need thereof, comprising the oral administration of sufficient amounts such compositions to such subject in an appropriate pharmaceutical form or vehicle.

e) methods of use of compositions comprising compounds of formulas 1a, 1b or 2, to treat immunosuppression associated with infectious diseases (e.g HIV-1 infection, influenza), in a subject in need thereof, comprising the oral administration of sufficient amounts such compositions to such subject in an appropriate pharmaceutical form or vehicle.

BRIEF DESCRIPTION OF THE DRAWINGS

FIG. 1 shows the XRPD spectrum of indoximod in free base and in its hydrochloride salt form.

FIG. 2 shows the thermos gravimetric (TGA) and differential scanning calorimetry (DSC) analysis of indoximod hydrochloride salt.

FIG. 3 shows the XRPD spectrum of indoximod in free base and in its phosphate salt form.

FIG. 4 shows the thermos gravimetric (TGA) and differential scanning calorimetry (DSC) analysis of indoximod phosphate salt.

FIG. 5 shows the measured solubility profile vs. pH of indoximod and its salts in various solvent solutions and simulated biological fluids.

FIG. 6 shows the maximum plasma concentration (Cmax) and exposure ($AUC_{0-inf}$) of indoximod vs the molar dose of indoximod, indoximod hydrochloride or indoximod phosphate given to rats in oral capsule form.

DETAILED DESCRIPTION OF THE INVENTION

Indoximod (1-methyl-D-tryptophan, D1mT) is an investigational inhibitor of the indoleamine-2,3-dioxygenase (IDO) pathway that is being tested in several human clinical trials for multiple cancer indications, in combination with standard and experimental chemotherapeutic and immunomodulatory agents and active immunotherapies.

In the presence of $IDO^+$ dendritic cells, $CD8^+$ effector T cells become anergic and unable to proliferate. Moreover, regulatory T cells ($CD4^+$ $CD25^+$ $FoxP3^+$) are activated in the presence of $IDO^+$ DCs and become able to mediate systemic immunosuppression to tumor or viral antigens. Indoximod is capable to revert these processes, allowing effector T cells to proliferate and directing reprogramming of Tregs to a TH17 helper-like phenotype. In in vitro assays, these effects are mediated by indoximod with an EC50 of ~30 μM [6]. In preclinical murine tumor models, antitumor effects, stimulation of effector T cells and reprogramming of Tregs in the draining lymph nodes requires daily doses of ~500 mg/kg, with exposures>300 μM·h.

Human pharmacokinetic experiments at oral doses that range between 200 mg to 2000 mg/dose have shown that the pharmacokinetic parameters $C_{max}$ and exposure ($AUC_{0-inf}$) increase linearly with dose, up to a range of ~800 mg/dose. At these doses, $C_{max}$ in plasma reaches an average of ~15 μM and $AUC_{0-inf}$ reaches ~100 μM·h. The $C_{max}$ and AUC parameters do not significantly increase above those values at higher doses of up to 2000 mg/dose. Therefore, in order to achieve indoximod concentration and exposure levels that are comparable to those that produce immunomodulatory and antitumor therapeutic effects in murine models it would be useful to increase the $C_{max}$ and exposure levels of indoximod.

The present invention describes compounds of formula 1a, 1b and formula 2 that produce a higher exposure and maximum serum concentration of indoximod upon oral administration, compared to oral administration of equivalent molar doses of indoximod.

Salts of Indoximod

In one embodiment, a salt of indoximod is disclosed. In one embodiment, the salt has a structure according to Formula 1a:

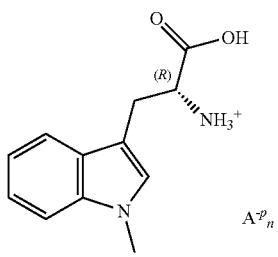

Formula 1a wherein $A^{-p}{}_n$ is an inorganic or organic anion in an ionization state $-p$. In one embodiment, the anion is present at a stoichiometric ratio n that ensures molecular charge neutrality.

In one embodiment, the anion $A^{-p}{}_n$ is selected from the group consisting of chloride, mesylate, besylate, acetate, ascorbate, sulfate, phosphate, glutamate, glutarate, lactate, maleate, malonate, oxalate, succinate, fumarate, tartrate and citrate. In one embodiment, the anion is presented at a stoichiometric ratio n such that the resulting salt is charge neutral. Accordingly, in one embodiment, the anion has an ionization state p of $-1$, $-2$ or $-3$ and is presented at a stoichiometric ratio n of 1, ½ or ⅓, respectively, such that the stoichiometric conditions of charge neutrality are satisfied. In one embodiment, the phosphate is $HPO_4^{-2}$, and the $HPO_4^{-2}$ is present at a stoichiometric ratio n of 0.5. In one embodiment, the phosphate is $HPO_4^{-}$, and the $HPO_4^{-}$ is present at a stoichiometric ratio n of 1. In one embodiment, the sulfate is $SO_4^{-2}$, and the $SO_4^{-2}$ is present at a stoichiometric ratio n of 0.5. In one embodiment, the mesylate is $CH_3SO_3^{-}$, and the $CH_3SO_3^{-}$ present at a stoichiometric ratio n of 0.5.

In another embodiment the anion $A^{-p}{}_n$ is $Cl^-$ at a stoichiometric ratio n of 1. In another preferred embodiment the anion $A^{-p}{}_n$ is $Cl^-$ at a stoichiometric ratio n of 1 and the crystalline form is an anhydrous isoform of Form 1.

In one embodiment, the salt has a structure according to Formula 1b:

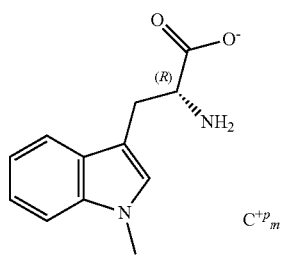

Formula 1b wherein $C^{+p}{}_m$ is a cation in an ionization state $+p$. In one embodiment, the cation is present at a stoichiometric ratio m that ensures molecular charge neutrality. In one embodiment, the $C^{+p}{}_m$ is selected from the group consisting of $Li^+$, $Na^+$, $K^+$, $Mg^{+2}$ and $Ca^{+2}$. In one embodiment, when p is +1, m is 1, and when p is +2, m is ½.

Indoximod Prodrugs

In one embodiment, a prodrug of indoximod is disclosed. In one embodiment, the structure of the prodrug, in free base or salt form, is provided in Formula 2:

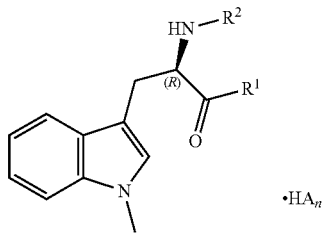

Formula 2

In one embodiment, $R^1$ is —OH, —$OC_{2-3}$alkyl, —$OCH_2CH(OH)CH_2OH$, —$O(CH_2)_2N(CH_3)_2$, —$OC_{1-3}$alkyl-$R^3$, —$NHC^{(S)}HR^4(COOH)$, —$NHC^{(R)}HR^4(COOH)$, —$OC_{1-6}$alkyl$R^6$, —$OC_{1-2}$alkyl-$C^{(S)}H(NH_2)(COOH)$, or —$OC_{1-2}$alkyl-$C^{(R)}H(NH2)(COOH)$. In one embodiment, $R^1$ is —$NHC^{(S)}HR^4(COOCH_3)$ or —$NHC^{(R)}HR^4(COOCH_3)$.

In one embodiment, $R^2$ is —H, —$C(O)C^{(S)}H(NH_2)R^4$, —$C(O)C^{(R)}H(NH_2)R^4$, —$C(O)CH_2C^{(S)}H(NH_2)$—$C(O)OCH_3$, —$C(O)OR^5$, or —$C(O)NHR^5$.

In one embodiment, $R^3$ is tetrahydropyran or

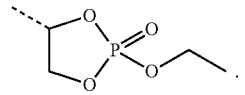

In one embodiment, $R^4$ is —H, —$C_{1-5}$alkyl, —$(CH_2)_{1-2}SH$, —$C_{1-5}$alkyl$SC_{1-5}$alkyl, —$C_{1-5}$alkyl$OC_{1-5}$alkyl, —$CH_2$—$R^6$, —$CH_2OH$, —$CH(OH)CH_3$, —$(CH_2)_{1-2}C(O)NH_2$, —$(CH_2)_{1-3}C(O)OH$, —$(CH_2)_{1-4}NH_2$, or —$(CH_2)_{1-3}NC(NH_2)NH_2$.

In one embodiment, when $R^4$ is not —H, $C^{(S)}$ and $C^{(R)}$ are carbons with the S or R stereochemistry, respectively.

In one embodiment, $R^5$ is —H, $C_{1-6}$alkyl$R^6$, or $R^6$. In one embodiment, $R^6$ is selected from the group consisting of —H, aryl, alkylaryl, heteroaryl, cycloalkyl, and heterocycloalkyl, wherein the aryl, alkylaryl, heteroaryl, cycloalkyl or heterocycloalkyl is optionally substituted with one two or three $R^7$ groups.

In one embodiment, each $R^7$ is independently halogen, cyano, nitro, —OR, —$N(R)_2$, —SR, —C(O)OR, $C_{1-6}$alkyl, $C_{1-6}$haloalkyl, —$C(O)N(R)_2$, —C(O)R, —S(O)R, —S(O)OR, —$S(O)N(R)_2$, —$S(O)_2R$, —$S(O)_2OR$, —$S(O)_2N(R)_2$, —OC(O)R, —OC(O)OR, —$OC(O)N(R)_2$, —N(R)C(O)R, —N(R)C(O)OR, or —$N(R)C(O)N(R)_2$, wherein R is H or $C_{1-4}$alkyl.

In some embodiments of the prodrug of Formula 2, $R^1$ cannot be OH when $R^2$ is H.

Furthermore, in all embodiments, the prodrug cannot be $N^\alpha$-tert-butoxycarbonyl-1-methyl-D-tryptophan, ethyl $N^\alpha$-benzyl-1-methyl-D-tryptophanate, or benzyl $N^\alpha$-(tert-butoxycarbonyl)-1-methyl-D-tryptophanate.

In one embodiment, $HA_n$ is an acid. In one embodiment, the acid HA is selected from the group consisting of $PO_4H_3$ (phosphoric acid), $SO_4H_2$ (sulfuric acid), HCl (hydrochloric acid), $HSO_3CH_3$ (methyl sulfonic acid), $C_6H_5SO_3H$ (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid.

In one embodiment, the acid HA$_n$ is present at a stoichiometric ratio n such that the resulting prodrug is charge neutral. Accordingly, in one embodiment, the stoichiometric ratio n of the acid HA$_n$ is 0, 0.5, 1 or 2 such that the prodrug is charge neutral.

The invention also provides prodrugs of indoximod, in their free base or salt form. In one embodiment, the prodrugs of indoximod are represented by compounds of Formula 2,

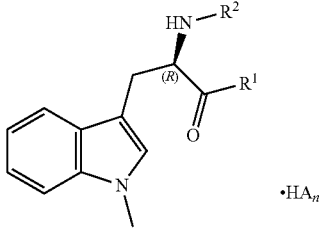

Formula 2 wherein
R$^1$ is —OH, —OC$_{2-3}$alkyl, —OCH$_2$CH(OH)CH$_2$OH, —O(CH$_2$)$_2$N(CH$_3$)$_2$, —OC$_{1-3}$alkyl-R$^3$, —NHC$^{(S)}$ HR$^4$(COOH), —NHC$^{(R)}$HR$^4$(COOH), —OC$_{1-6}$ alkylR$^6$, —OC$_{1-2}$ alkyl, —C$^{(S)}$H(NH$_2$)(COOH), or —OC$_{1-2}$alkyl-C$^{(R)}$H(NH2)(COOH);
R$^2$ is —H, —C(O)C$^{(S)}$H(NH$_2$)R$^4$, —C(O)C$^{(R)}$H(NH$_2$)R$^4$, —C(O)CH$_2$C$^{(S)}$H(NH$_2$)—C(O)OCH$_3$, —C(O)OR$^5$, or —C(O)NHR$^5$,
R$^3$ is tetrahydropyran, or

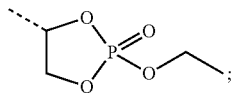

wherein R$^4$ is H, —C$_{1-5}$alkyl, —(CH$_2$)$_{1-2}$SH, C$_{1-5}$alkylSC$_{1-5}$alkyl, —C$_{1-5}$alkylOC$_{1-5}$alkyl, —CH$_2$—R$^6$, —CH$_2$OH, —CH(OH)CH$_3$, —(CH$_2$)$_{1-2}$C(O)NH$_2$, —(CH$_2$)$_{1-3}$C(O)OH, —(CH$_2$)$_{1-4}$NH$_2$, or —(CH$_2$)$_{1-3}$NC(=NH$_2$)NH$_2$;
wherein C$^{(S)}$ and C$^{(R)}$ represents a carbon with the S or R stereochemistry, respectively,
when R$^4$ is not —H; wherein R$^5$ is —H, C$_{1-6}$alkylR$^6$; or R$^6$
wherein R$^6$ is H, aryl, alkylaryl, heteroaryl, cycloalkyl, or heterocycloalkyl, wherein such aryl, alkylaryl, heteroaryl, cycloalkyl or heterocycloalkyl is optionally substituted with one two or three R$^7$ groups;
wherein each R$^7$ is independently selected from halogen, cyano, nitro, —OR, —N(R)$_2$, —SR, —C(O)OR, C$_{1-6}$alkyl, C$_{1-6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;
wherein R is —H or C$_{1-4}$alkyl;
with the proviso that R$^1$ cannot be —OH when R$^2$ is —H, and the compound cannot be
N$^\alpha$-tert-butoxy carbonyl-1-methyl-D-tryptophan
ethyl N$^\alpha$-benzyl-1-methyl-D-tryptophanate
benzyl N$^\alpha$-(tert-butoxycarbonyl)-1-methyl-D-tryptophanate
HA$_n$ is an acid selected from the group consisting of PO$_4$H$_3$ (phosphoric acid), SO$_4$H$_2$ (sulfuric acid), HCl (hydrochloric acid), HSO$_3$CH$_3$ (methyl sulfonic acid), C$_6$H$_5$SO$_3$H (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid; and n is the stoichiometric ratio of 0, 0.5, 1 or 2 that ensure charge neutrality of the resulting salt.

In a another embodiment, the invention provides prodrugs of indoximod, in their free base or salt form, as represented by compounds of Formula 2,

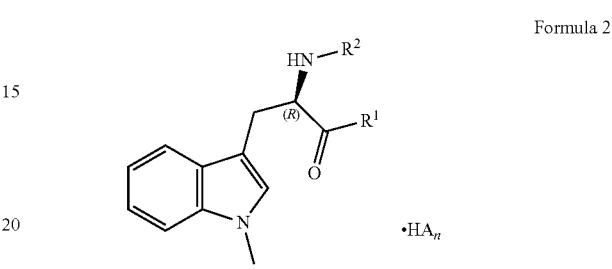

Formula 2 wherein R$^1$ is —OH, —OCH$_2$CH(OH)CH$_2$OH, —O(CH$_2$)$_2$N(CH$_3$)$_2$, or —OC$_{1-3}$alkyl-R$^3$, —
R$^2$ is H, or —C(O)C$^{(S)}$H(NH$_2$)R$^4$,
R$^3$ is tetrahydropyran, or wherein R$^4$ is H, —(CH$_2$)$_{1-2}$SH, —(CH$_2$)$_{1-3}$SCH$_3$, —(CH$_2$)$_{1-3}$OCH$_3$, —CH$_2$—R$^6$, —CH$_2$OH, —CH(OH)CH$_3$, —(CH$_2$)$_{1-2}$C(O)NH$_2$, —(CH$_2$)$_{1-3}$C(O)OH, —(CH$_2$)$_{1-4}$NH$_2$, or —(CH$_2$)$_{1-3}$NC(=NH$_2$)NH$_2$;
wherein C$^{(S)}$ represents a carbon with the S stereochemistry, when R$^4$ is not H;
wherein R$^6$ is H, aryl, alkylaryl, heteroaryl, cycloalkyl, heterocycloalkyl, wherein such aryl, alkylaryl, heteroaryl, cycloalkyl or heterocycloalkyl is optionally substituted with one two or three R$^7$ groups;
wherein each R$^7$ is independently halogen, cyano, nitro, —OR, —N(R)$_2$, —SR, —C(O)OR, C$_{1-6}$alkyl, C$_{1-6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;
wherein R is H or C$_{1-4}$alkyl;
with the proviso that R$^1$ cannot be —OH when R$^2$ is H;
HA$_n$ is an acid selected from the group consisting of PO$_4$H$_3$ (phosphoric acid), SO$_4$H$_2$ (sulfuric acid), HCl (hydrochloric acid), HSO$_3$CH$_3$ (methyl sulfonic acid), C$_6$H$_5$SO$_3$H (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid; and n is the stoichiometric ratio of 0, 0.5, 1 or 2 that ensure charge neutrality of the resulting salt.

In a preferred embodiment, the invention provides prodrugs of indoximod, in their free base or salt form, as represented by compounds of Formula 2, Formula 2

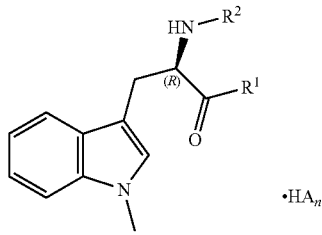

wherein
R¹ is —OH, —OC$_{2-3}$alkyl, —OCH$_2$CH(OH)CH$_2$OH, —O(CH$_2$)$_2$N(CH$_3$)$_2$, or —OC$_{1-3}$alkyl-R³,
R² is H, or —C(O)C$^{(S)}$H(NH$_2$)R⁴,
R³ is tetrahydropyran, or

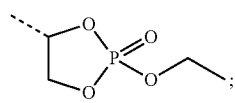

wherein R⁴ is H, —C$_{1-5}$alkyl, —CH$_2$—R⁶, —(CH$_2$)$_{1-2}$C(O)NH$_2$, —(CH$_2$)$_2$SCH$_3$, —(CH$_2$)$_{1-3}$C(O)OH, or —(CH$_2$)$_{1-4}$NH$_2$
wherein C$^{(S)}$ represents a carbon with the S stereochemistry, when R⁴ is not —H;
wherein R⁶ is —H, aryl, alkylaryl, or heteroaryl, wherein such aryl, alkylaryl or heteroaryl is optionally substituted with one R⁷ group;
wherein R⁷ is selected from halogen, cyano, nitro, —OR, —N(R)$_2$, —SR, —C(O)OR, C$_{1-6}$alkyl, C$_{1-6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;
wherein R is —H or C$_{1-4}$alkyl;
with the proviso that R¹ cannot be —OH when R² is H;
HA$_n$ is an acid selected from the group of PO$_4$H$_3$ (phosphoric acid), SO$_4$H$_2$ (sulfuric acid), HCl (hydrochloric acid), HSO$_3$CH$_3$ (methyl sulfonic acid), or C$_6$H$_5$SO$_3$H (benzyl sulfonic acid); and n is the stoichiometric ratio of 0, 0.5, 1 or 2 that ensure charge neutrality of the resulting salt.

In another preferred embodiment, the invention provides prodrugs of indoximod, in their free base or salt form, as represented by compounds of Formula 2, Formula 2

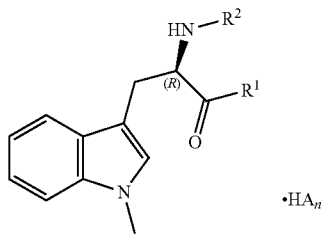

wherein
R¹ is —OH, —OC$_{2-3}$alkyl, —OCH$_2$CH(OH)CH$_2$OH, —O(CH$_2$)$_2$N(CH$_3$)$_2$, or —OC$_{1-3}$alkyl-R³,
R² is H, or —C(O)C$^{(S)}$H(NH$_2$)R⁴,
R³ is tetrahydropyran, or

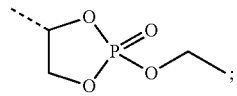

wherein R⁴ is —CH$_2$CH(CH$_3$)$_2$, —C$^{(S)}$H(CH$_3$)CH$_2$CH$_3$, —(CH$_2$)$_2$SCH$_3$, —CH$_2$—R⁶, —(CH$_2$)$_2$C(O)NH$_2$, —(CH$_2$)$_3$C(O)OH, or —(CH$_2$)$_4$NH$_2$;
wherein C$^{(S)}$ represents a carbon with the S stereochemistry;
wherein R⁶ is phenyl;
with the proviso that R¹ cannot be —OH when R² is H;
HA$_n$ is an acid selected from the group consisting of PO$_4$H$_3$ (phosphoric acid), SO$_4$H$_2$ (sulfuric acid), HCl (hydrochloric acid) HSO$_3$CH$_3$ (methyl sulfonic acid), and C$_6$H$_5$SO$_3$H (benzyl sulfonic acid), and n is the stoichiometric ratio of 0, 0.5, 1 or 2 that ensure charge neutrality of the resulting salt.

In a most preferred embodiment, the invention provides prodrugs of indoximod, in their free base or salt form, as represented by compounds of Formula 2, Formula 2

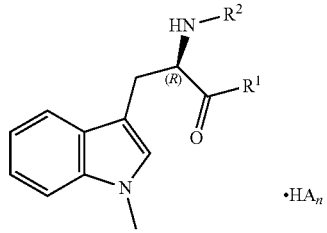

wherein
R¹ is —OC$_{2-3}$alkyl, or —OCH$_2$CH(OH)CH$_2$OH,
R² is H or —C(O)C$^{(S)}$H(NH$_2$)R⁴,
wherein R⁴ is —CH$_2$CH(CH$_3$)$_2$, —(CH$_2$)$_2$SCH$_3$, or —(CH$_2$)$_2$C(O)NH$_2$;
wherein C$^{(S)}$ represents a carbon with the S stereochemistry
with the proviso that R¹ cannot be OH when R² is H,
HA is an acid selected from the group of PO$_4$H$_3$ (phosphoric acid), SO$_4$H$_2$ (sulfuric acid), HCl (hydrochloric acid) HSO$_3$CH$_3$ (methyl sulfonic acid) or C$_6$H$_5$SO$_3$H (benzyl sulfonic acid); and n is the stoichiometric ratio of 0, 0.5, 1 or 2 that ensure charge neutrality of the resulting salt.

In a preferred embodiment, the invention provides prodrugs of indoximod, in their free base or as a pharmaceutically appropriate salt form, as represented by compounds of Formula 2 represented in Table 1.

In one embodiment, the prodrug substantially includes at least one of the following compounds: (i) ethyl N$^\alpha$-(L-leucyl)-1-methyl-D-tryptophanate; (ii) 2,3-dihydroxypropyl 1-methyl-D-tryptophanate; (iii) N$^\alpha$-(L-leucyl)-1-methyl-D-tryptophan; (iv) ethyl N$^\alpha$-(L-isoleucyl)-1-methyl-D-tryptophanate; (v) N$^\alpha$-(L-glycyl)-1-methyl-D-tryptophan; (vi) (S)-5-amino-6-(((R)-1-carboxy-2-(1-methyl-1H-indol-3-yl)ethyl)amino)-6-oxohexanoic acid; (vii) N$^\alpha$-(L-lysyl)-1-methyl-D-tryptophan; (viii) N$^\alpha$-(L-phenylalanyl)-1-methyl-D-tryptophan; (ix) ethyl N$^\alpha$-(L-glutaminyl)-1-methyl-D-tryptophanate; (x) 2-(dimethylamino)ethyl 1-methyl-D-tryptophanate; (xi) (2-ethoxy-2-oxido-1,3,2-dioxaphospholan-4-yl)methyl 1-methyl-D-tryptophanate;

(xii) 2-(tetrahydro-2H-pyran-4-yl)ethyl 1-methyl-D-tryptophanate; (xiii) ethyl 1-methyl-D-tryptophanate; (xiv) isopropyl 1-methyl-D-tryptophanate; (xv) N$^\alpha$-(L-methionyl)-1-methyl-D-tryptophan; or (xvi) ethyl N$^\alpha$-(L-methionyl)-1-methyl-D-tryptophanate.

Pharmaceutical Compositions of Indoximod Salts and Prodrugs

In one aspect, the invention provides a pharmaceutical composition comprising salts of indoximod, as represented by compounds of Formula 1a and 1b,

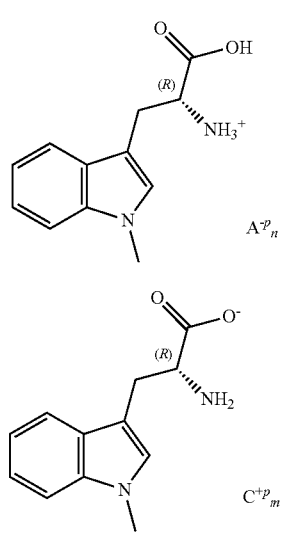

Formula 1a

Formula 1b wherein $A^{-p}{}_n$ is an inorganic or organic anion and $C^{+p}{}_m$ is an inorganic cation in an ionization state and at a stoichiometric ratio that ensures molecular charge neutrality.

In a second embodiment of the first aspect, the invention provides a pharmaceutical composition comprising salts of indoximod, as represented by compounds of Formula 1a, wherein $A^{-p}{}_n$ is an anion selected from the group consisting of chloride, phosphate, sulfate, mesylate, besylate, acetate, ascorbate, aspartate, glutamate, glutarate, lactate, maleate, malonate, oxalate, succinate, fumarate, tartrate and citrate, wherein negative charge p is −1, −2 or −3 at stoichiometric ratio n of 1, ½ or ⅓, respectively, so that it satisfies stoichiometric conditions of charge neutrality.

In a third embodiment of the first aspect, the invention provides a pharmaceutical composition comprising salts of indoximod, as represented by compounds of Formula 1b, wherein $C^{+p}{}_m$ is an cation selected from the group of Li$^+$, Na$^+$, K$^+$, Mg$^{+2}$ or Ca$^{+2}$, wherein positive charge p is +1 or +2 at stoichiometric ratio m of 1 or ½, respectively, so that it satisfies stoichiometric conditions of charge neutrality.

In a fourth embodiment of the first aspect, the invention provides a pharmaceutical composition comprising salts of indoximod, as represented by compounds of Formula 1a, wherein $A^{-p}{}_n$ is an anion selected from the group consisting of $HPO_4^{-2}$ (phosphate), $SO_4^{-2}$ (sulfate), $H_2PO_4^-$ (phosphate), $Cl^-$, and $CH_3SO_3^-$ (mesylate), at stoichiometric ratio n of 0.5, 0.5, 1 or 1, respectively.

In a preferred fifth embodiment of the first aspect, the invention provides a pharmaceutical composition comprising salts of indoximod, as represented by compounds of Formula 1a, wherein $A^{-p}{}_n$ is Cl$^-$ at a stoichiometric ratio n of 1.

In a most preferred fifth embodiment of the first aspect, the invention provides a pharmaceutical composition comprising salts of indoximod, as represented by compounds of Formula 1a, wherein $A^{-p}{}_n$ is Cl$^-$ at a stoichiometric ratio n of 1 and the crystalline form is an anhydrous isoform of Form 1 In a second aspect, the invention provides a pharmaceutical composition comprising prodrugs of indoximod, in their free base or salt form. In one embodiment, the prodrugs of indoximod are represented by compounds of Formula 2,

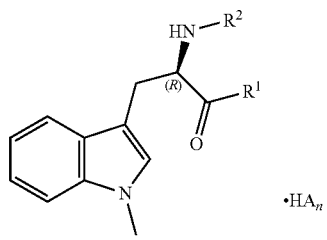

Formula 2 wherein
R$^1$ is —OH, —OC$_{2-3}$alkyl, —OCH$_2$CH(OH)CH$_2$OH, —O(CH$_2$)$_2$N(CH$_3$)$_2$, —OC$_{1-3}$alkyl-R$^3$, —NHC$^{(S)}$HR$^4$(COOH), —NHC$^{(R)}$HR$^4$(COOH), —OC$_{1-6}$ alkylR$^6$, —OC$_{1-2}$ alkyl, —C$^{(S)}$H(NH$_2$)(COOH), or —OC$_{1-2}$alkyl-C$^{(R)}$H(NH2)(COOH);
R$^2$ is —H, —C(O)C$^{(S)}$H(NH$_2$)R$^4$, —C(O)C$^{(R)}$H(NH$_2$)R$^4$, —C(O)CH$_2$C$^{(S)}$H(NH$_2$)—C(O)OCH$_3$, —C(O)OR$^5$, or —C(O)NHR$^5$,
R$^3$ is tetrahydropyran, or

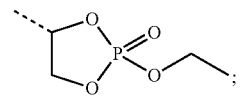

wherein R$^4$ is H, —C$_{1-5}$alkyl, —(CH$_2$)$_{1-2}$SH, C$_{1-5}$alkylSC$_{1-5}$alkyl, —C$_{1-5}$alkylOC$_{1-5}$alkyl, —CH$_2$—R$^6$, —CH$_2$OH, —CH(OH)CH$_3$, —(CH$_2$)$_{1-2}$C(O)NH$_2$, —(CH$_2$)$_{1-3}$C(O)OH, —(CH$_2$)$_{1-4}$NH$_2$, or —(CH$_2$)$_{1-3}$NC(NH$_2$)NH$_2$;
wherein C$^{(S)}$ and C$^{(R)}$ represents a carbon with the S or R stereochemistry, respectively,
when R$^4$ is not —H; wherein R$^5$ is —H, C$_{1-6}$alkylR$^6$; or R$^6$
wherein R$^6$ is H, aryl, alkylaryl, heteroaryl, cycloalkyl, or heterocycloalkyl, wherein such aryl, alkylaryl, heteroaryl, cycloalkyl or heterocycloalkyl is optionally substituted with one two or three R$^7$ groups;
wherein each R$^7$ is independently selected from halogen, cyano, nitro, —OR, —N(R)$_2$, —SR, —C(O)OR, C$_{1-6}$alkyl, C$_{1-6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;
wherein R is —H or C$_{1-4}$alkyl;
with the proviso that R$^1$ cannot be —OH when R$^2$ is —H, and the compound cannot be
N$^\alpha$-tert-butoxy carbonyl-1-methyl-D-tryptophan
ethyl N$^\alpha$-benzyl-1-methyl-D-tryptophanate
benzyl N$^\alpha$-(tert-butoxycarbonyl)-1-methyl-D-tryptophanate HA$_n$ is an acid selected from the group consisting of PO$_4$H$_3$ (phosphoric acid), SO$_4$H$_2$ (sulfuric acid), HCl (hydrochloric acid), HSO$_3$CH$_3$ (methyl sulfonic acid), C$_6$H$_5$SO$_3$H (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid; and n is the stoichiometric ratio of 0, 0.5, 1 or 2 that ensure charge neutrality of the resulting salt.

In a another embodiment of the second aspect, the invention provides a pharmaceutical composition comprising prodrugs of indoximod, in their free base or salt form, as represented by compounds of Formula 2,

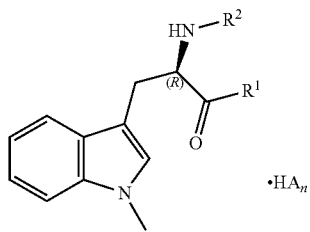

Formula 2 wherein R$^1$ is —OH, —OC$_{2\text{-}3}$alkyl, —OCH$_2$CH(OH)CH$_2$OH, —O(CH$_2$)$_2$N(CH$_3$)$_2$, or —OC$_{1\text{-}3}$alkyl-R$^3$, —

R$^2$ is H, or —C(O)C$^{(S)}$H(NH$_2$)R$^4$,

R$^3$ is tetrahydropyran, or

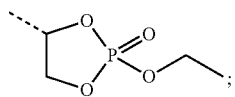

wherein R$^4$ is H, —C$_{1\text{-}5}$alkyl, —(CH$_2$)$_{1\text{-}2}$SH, —(CH$_2$)$_{1\text{-}3}$SCH$_3$, —(CH$_2$)$_{1\text{-}3}$OCH$_3$, —CH$_2$—R$^6$, —CH$_2$OH, —CH(OH)CH$_3$, —(CH$_2$)$_{1\text{-}2}$C(O)NH$_2$, —(CH$_2$)$_{1\text{-}3}$C(O)OH, —(CH$_2$)$_{1\text{-}4}$NH$_2$, or —(CH$_2$)$_{1\text{-}3}$NC(=NH$_2$)NH$_2$;

wherein C$^{(S)}$ represents a carbon with the S stereochemistry, when R$^4$ is not H;

wherein R$^6$ is H, aryl, alkylaryl, heteroaryl, cycloalkyl, heterocycloalkyl, wherein such aryl, alkylaryl, heteroaryl, cycloalkyl or heterocycloalkyl is optionally substituted with one two or three R$^7$ groups;

wherein each R$^7$ is independently halogen, cyano, nitro, —OR, —N(R)$_2$, —SR, —C(O)OR, C$_{1\text{-}6}$alkyl, C$_{1\text{-}6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

wherein R is H or C$_{1\text{-}4}$alkyl;

with the proviso that R$^1$ cannot be —OH when R$^2$ is H;

HA$_n$ is an acid selected from the group consisting of PO$_4$H$_3$ (phosphoric acid), SO$_4$H$_2$ (sulfuric acid), HCl (hydrochloric acid), HSO$_3$CH$_3$ (methyl sulfonic acid), C$_6$H$_5$SO$_3$H (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid; and n is the stoichiometric ratio of 0, 0.5, 1 or 2 that ensure charge neutrality of the resulting salt.

In a preferred embodiment of the second aspect, the invention provides a pharmaceutical composition comprising prodrugs of indoximod, in their free base or salt form, as represented by compounds of Formula 2,

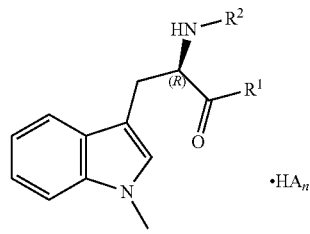

Formula 2 wherein

R$^1$ is —OH, —OC$_{2\text{-}3}$alkyl, —OCH$_2$CH(OH)CH$_2$OH, —O(CH$_2$)$_2$N(CH$_3$)$_2$, or —OC$_{1\text{-}3}$alkyl-R$^3$, R$^2$ is H, or —C(O)C$^{(S)}$H(NH$_2$)R$^4$, R$^3$ is tetrahydropyran, or

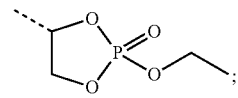

wherein R$^4$ is H, —C$_{1\text{-}5}$alkyl, —CH$_2$—R$^6$, —(CH$_2$)$_{1\text{-}2}$C(O)NH$_2$, —(CH$_2$)$_2$SCH$_3$, —(CH$_2$)$_{1\text{-}3}$C(O)OH, or —(CH$_2$)$_{1\text{-}4}$NH$_2$ wherein C$^{(S)}$ represents a carbon with the S stereochemistry, when R$^4$ is not —H;

wherein R$^6$ is —H, aryl, alkylaryl, or heteroaryl, wherein such aryl, alkylaryl or heteroaryl is optionally substituted with one R$^7$ group;

wherein R$^7$ is selected from halogen, cyano, nitro, —OR, —N(R)$_2$, —SR, —C(O)OR, C$_{1\text{-}6}$alkyl, C$_{1\text{-}6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$;

wherein R is —H or C$_{1\text{-}4}$alkyl;

with the proviso that R$^1$ cannot be —OH when R$^2$ is H;

HA$_n$ is an acid selected from the group of PO$_4$H$_3$ (phosphoric acid), SO$_4$H$_2$ (sulfuric acid), HCl (hydrochloric acid), HSO$_3$CH$_3$ (methyl sulfonic acid), or C$_6$H$_5$SO$_3$H (benzyl sulfonic acid); and n is the stoichiometric ratio of 0, 0.5, 1 or 2 that ensure charge neutrality of the resulting salt.

In a most preferred embodiment of the second aspect, the invention provides a pharmaceutical composition comprising prodrugs of indoximod, in their free base or salt form, as represented by compounds of Formula 2,

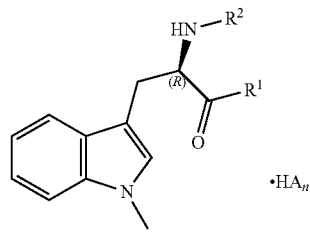

Formula 2 wherein
R¹ is —OH, —OC$_{2-3}$alkyl, —OCH$_2$CH(OH)CH$_2$OH, —O(CH$_2$)$_2$N(CH$_3$)$_2$, or —OC$_{1-3}$alkyl-R³,
R² is H, or —C(O)C$^{(S)}$H(NH$_2$)R⁴,
R³ is tetrahydropyran, or

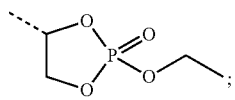

wherein R⁴ is —CH$_2$CH(CH$_3$)$_2$, —C$^{(S)}$H(CH)$_3$CH$_2$CH$_3$, —(CH$_2$)$_2$SCH$_3$, —CH$_2$—R⁶, —(CH$_2$)$_2$C(O)NH$_2$, —(CH$_2$)$_3$C(O)OH, or —(CH$_2$)$_4$NH$_2$;
wherein C$^{(S)}$ represents a carbon with the S stereochemistry;
wherein R⁶ is phenyl;
with the proviso that R¹ cannot be —OH when R² is H;
HA$_n$ is an acid selected from the group consisting of PO$_4$H$_3$ (phosphoric acid), SO$_4$H$_2$ (sulfuric acid), HCl (hydrochloric acid) HSO$_3$CH$_3$ (methyl sulfonic acid), and C$_6$H$_5$SO$_3$H (benzyl sulfonic acid), and n is the stoichiometric ratio of 0, 0.5, 1 or 2 that ensure charge neutrality of the resulting salt.

In a most preferred embodiment of the second aspect, the invention provides a pharmaceutical composition comprising prodrugs of indoximod, in their free base or salt form, as represented by compounds of Formula 2,

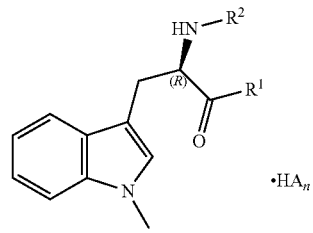

Formula 2 wherein
R¹ is —OC$_{2-3}$alkyl, or —OCH$_2$CH(OH)CH$_2$OH,
R² is H or —C(O)C$^{(S)}$H(NH$_2$)R⁴,
wherein R⁴ is —CH$_2$CH(CH$_3$)$_2$, —(CH$_2$)$_2$SCH$_3$, or —(CH$_2$)$_2$C(O)NH$_2$;
wherein C$^{(S)}$ represents a carbon with the S stereochemistry
with the proviso that R¹ cannot be OH when R² is H,
HA is an acid selected from the group of PO$_4$H$_3$ (phosphoric acid), SO$_4$H$_2$ (sulfuric acid), HCl (hydrochloric acid) HSO$_3$CH$_3$ (methyl sulfonic acid) or C$_6$H$_5$SO$_3$H (benzyl sulfonic acid); and n is the stoichiometric ratio of 0, 0.5, 1 or 2 that ensure charge neutrality of the resulting salt.

In a preferred embodiment, the invention provides a pharmaceutical composition comprising prodrugs of indoximod, in their free base or as a pharmaceutically appropriate salt form, as represented by compounds of Formula 2 represented in Table 1.

TABLE 1

| | Prodrugs of indoximod | |
|---|---|---|
| Cpd Number | Structure | Name |
| 01 | | ethyl N$^\alpha$-(L-leucyl)-1-methyl-D-tryptophanate |
| 02 | | 2,3-dihydroxypropyl 1-methyl-D-tryptophanate |

TABLE 1-continued

Prodrugs of indoximod

| Cpd Number | Structure | Name |
|---|---|---|
| 03 | 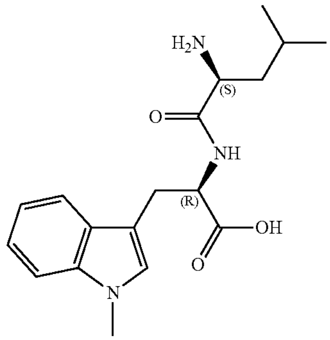 | N$^\alpha$-(L-leucyl)-1-methyl-D-tryptophan |
| 04 | 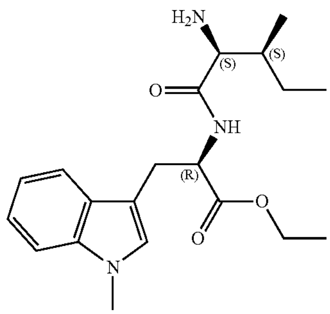 | ethyl N$^\alpha$-(L-isoleucyl)-1-methyl-D-tryptophanate |
| 05 | 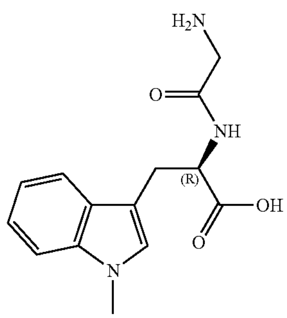 | N$^\alpha$-(L-glycyl)-1-methyl-D-tryptophan |
| 06 | 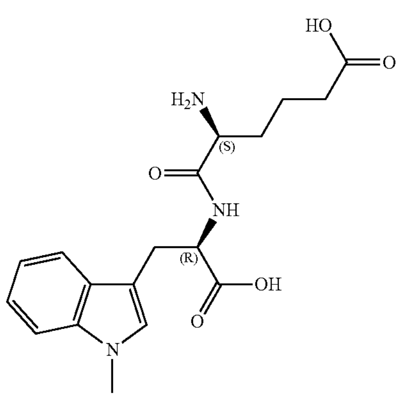 | (S)-5-amino-6-(((R)-1-carboxy-2-(1-methyl-1H-indol-3-yl)ethyl)amino)-6-oxohexanoic acid |

TABLE 1-continued
Prodrugs of indoximod
| Cpd Number | Structure | Name |
|---|---|---|
| 07 | 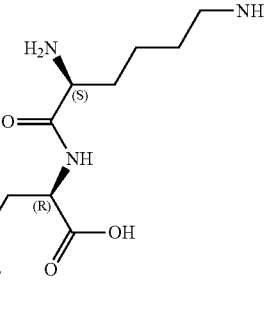 | N$^\alpha$-(L-lysyl)-1-methyl-D-tryptophan |
| 08 | 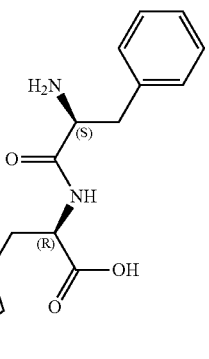 | N$^\alpha$-(L-phenylalanyl)-1-methyl-D-tryptophan |
| 09 | 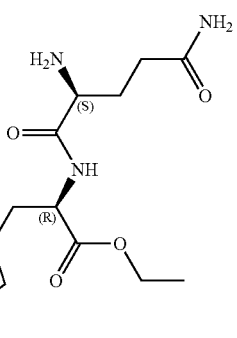 | ethyl N$^\alpha$-(L-glutaminyl)-1-methyl-D-tryptophanate |
| 10 | 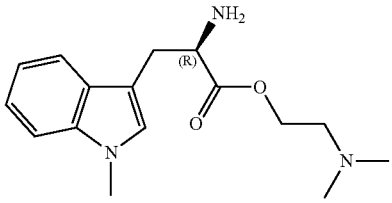 | 2-(dimethylamino)ethyl 1-methyl-D-tryptophanate |
| 11 | 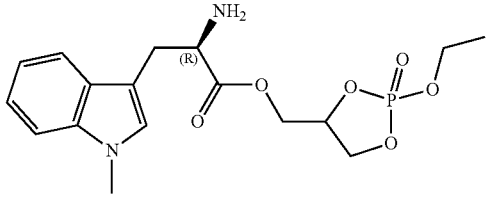 | (2-ethoxy-2-oxido-1,3,2-dioxaphospholan-4-yl)methyl 1-methyl-D-tryptophanate |

TABLE 1-continued

Prodrugs of indoximod

| Cpd Number | Structure | Name |
|---|---|---|
| 12 | 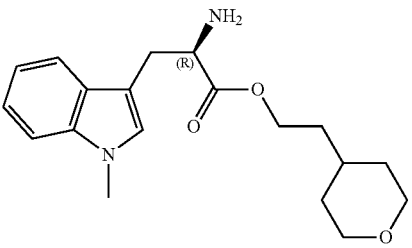 | 2-(tetrahydro-2H-pyran-4-yl)ethyl 1-methyl-D-tryptophanate |
| 13 | 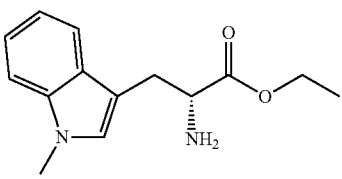 [SMILES: CCOC(=O)[C@H](N)Cc1cn(C)c2ccccc12] | ethyl 1-methyl-D-tryptophanate |
| 14 | 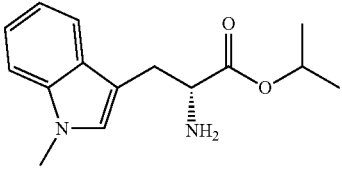 [SMILES: CC(C)OC(=O)[C@H](N)Cc1cn(C)c2ccccc12] | isopropyl 1-methyl-D-tryptophanate |
| 15 | 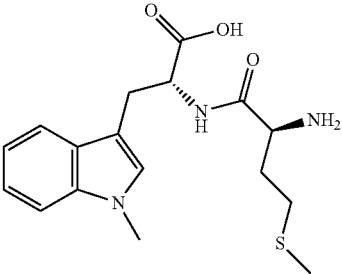 [SMILES: CSCC[C@H](N)C(=O)N[C@H](Cc1cn(C)c2ccccc12)C(=O)O] | $N^\alpha$-(L-methionyl)-1-methyl-D-tryptophan |
| 16 | 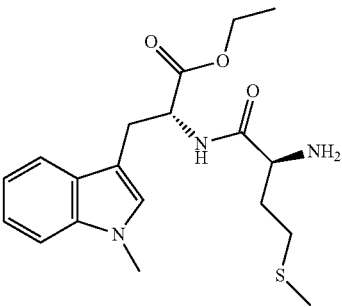 [SMILES: CCOC(=O)[C@@H](Cc1cn(C)c2ccccc12)NC(=O)[C@@H](N)CCSC] | ethyl $N^\alpha$-(L-methionyl)-1-methyl-D-tryptophanate |

In another aspect, the invention provides methods of use of compositions of formulas 1 and 2, to modulate the activity of indoleamine-2,3-dioxygenase pathway in a subject in need thereof, comprising the oral administration of therapeutically effective amounts such compositions to such subject in an appropriate pharmaceutical form or vehicle.

In another aspect, the invention provides methods of use of compositions of formulas 1a, 1b and 2, for the treatment of cancer in a subject in need thereof, comprising the oral administration of therapeutically effective amounts of such compositions to such subject in an appropriate pharmaceutical form or vehicle.

In another aspect, the invention provides methods of use of compositions of formulas 1a, 1b and 2, for the treatment of tumor-specific immunosuppression associated with cancer, in a subject in need thereof, comprising the oral administration of sufficient amounts such compositions to such subject in an appropriate pharmaceutical form or vehicle.

In another aspect, the invention provides methods of use of compositions of formulas 1a, 1b and 2, to treat immunosuppression associated with infectious diseases (e.g HIV-1 infection, influenza), in a subject in need thereof, comprising the oral administration of sufficient amounts such compositions to such subject in an appropriate pharmaceutical form or vehicle.

In one embodiment, a salt and/or a prodrug of indoximod is included in a pharmaceutical composition, and the composition is included in a solid capsule, gelatin capsule, tablet or pill. In one embodiment, the salt and/or the prodrug is included in a dissolvable capsule.

In specific embodiments, the compositions of the present invention may additionally contain other adjunct components conventionally found in pharmaceutical compositions, at their art-established usage levels. Thus, for example, the compositions may contain additional materials useful in physically formulating various dosage forms of the compositions of the present invention, such as dyes, flavoring agents, preservatives, antioxidants, opacifiers, thickening agents and stabilizers. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more excipients. In certain such embodiments, excipients are selected from water, salt solutions, alcohol, polyethylene glycols, gelatin, lactose, lactose monohydrate, amylase, magnesium stearate, talc, silicic acid, viscous paraffin, hydroxymethylcellulose, microcrystalline cellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tableting processes.

Additional embodiments relate to the pharmaceutical formulations wherein the formulation is selected from the group consisting of a solid, powder, liquid and a gel. In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more ingredients known in the art, including, but not limited to, starches, sugars, diluents, granulating agents, lubricants, binders, and disintegrating agents.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, lactose monohydrate, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, microcrystalline cellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked carboxymethyl cellulose, such as croscarmellose sodium, cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition of the present invention may be an effervescent tablet or granulate. Effervescent tablets most commonly consist of a soluble acid source and a carbonate source to produce carbon dioxide gas, the latter serving as disintegrant. The acidity needed for the effervescent reaction can be derived from food acids, acid anhydrides and acid salts. The food acid can for example be citric acid, tartaric acid, malic acid, fumaric acid, adipic acid or succinic acid. The acid anhydride may be succinic anhydride or citric anhydride or the like. The acid salts may be e.g. sodium dihydrogen phosphate (monosodium phosphate), disodium dihydrogen pyrophosphate (sodium acid pyrophosphate), acid citric salts (sodium dihydrogen citrate and disodium hydrogen citrate), sodium acid sulfite (sodium bisulfite). Suitable carbonate sources are for example sodium bicarbonate, sodium carbonate, potassium bicarbonate, potassium carbonate, sodium sesquicarbonate (mixture of equal molar amounts of sodium carbonate and sodium bicarbonate), glycine carbonate, L-lysine carbonate, arginine carbonate, calcium carbonate.

Effervescence may also be induced by the formation of other gases such as oxygen, e.g. released from sodium perborate or from a combination of e.g. a peroxygen compound that yields active oxygen on mixture with water (e.g. sodium perborate monohydrate or sodium percarbonate) and a chlorine compound that liberates hypochlorite on contact with water (e.g. sodium dichloroisocyanurate or calcium hypochlorite).

The pharmaceutical composition of the present invention can be manufactured according to standard methods known in the art. Granulates and effervescent tablets according to the invention can be obtained by dry compaction or wet granulation. These granulates can subsequently be mixed with e.g. suitable disintegrating agents, glidants and lubricants and be compressed into tablets or filled into e.g. sachets of suitable size. Effervescent tablets can also be obtained by direct compression of a suitable powder mixture, i.e. without any preceding granulation of the excipients.

Suitable powder or granulate mixtures according to the invention are also obtainable by spray drying (e.g., by hot process spray drying or by basic spray drying), lyophilization, melt extrusion, pellet layering, coating of the active pharmaceutical ingredient or any other suitable method. Preferably, the conditions are chosen such as to prevent amorphization of the active pharmaceutical ingredient. The so obtained powders or granulates can be mixed with one or more suitable ingredients and the resulting mixtures can either be compressed to form effervescent tablets or filled into sachets.

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

DEFINITIONS

Terms used herein may be preceded and/or followed by a single dash, "-", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_{1-6}$alkoxycarbonyloxy and —OC(O)$C_{1-6}$alkyl indicate the same functionality; similarly arylalkyl, arylalkyl-, and alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkenyl" as used herein, means a straight or branched chain hydrocarbon containing from 2 to 10 carbons, unless otherwise specified, and containing at least one carbon carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta 2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term $C_{1-5}$alkyl refers to a linear or branched alkyl of 1 to 5 carbon atoms.

The term $C_{1-6}$alkyl refers to a linear or branched alkyl of 1 to 6 carbon atoms.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxin-5-yl, 2,3-dihydrobenzo[b][1,4]dioxin-6-yl, 2H-benzo[b][1,4]oxazin3 (4H)-on-5-yl, 2Hbenzo[b][1,4]oxazin3 (4H)-on-6-yl, 2H benzo[b][1,4]oxazin3(4H)-on-7-yl, 2Hbenzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl," "alkylaryl," and "arylalkyl-" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic cycloalkenyls include, but are not limited to, norbornenyl and bicyclo [2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "halo" or "halogen" as used herein, means Cl, Br, I or F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, indolyl, 1-methyl-indolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridine-4-yl)ethyl, pyridine-3-ylmethyl, pyridine-4-ylmethyl, pyrimidin-5-ylmethyl, 2-(pyrimidin-2-yl)propyl, thien-2-ylmethyl, and thien-3-ylmethyl.

The terms "heterocyclyl" or "heterocycloalkyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The term "nitro" as used herein, means a —NO$_2$ group.

The term "oxo" as used herein means a =O group.

The term "thia" as used herein means a —S— group.

The term "saturated" as used herein means the referenced chemical structure does not contain any multiple carbon-carbon bonds. For example, a saturated cycloalkyl group as defined herein includes cyclohexyl, cyclopropyl, and the like.

The term "unsaturated" as used herein means the referenced chemical structure contains at least one multiple carbon carbon bond, but is not aromatic. For example, a unsaturated cycloalkyl group as defined herein includes cyclohexenyl, cyclopentenyl, cyclohexadienyl, and the like.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., IDO modulation or tryptophan degradation inhibition).

Manifestation of amelioration of a disease condition with underlying IDO-mediated immunosuppression may require the concomitant or sequential administration of additional therapeutic agents, such as antineoplastic agents in the case of cancer, or antiretroviral agents in the case of viral diseases. For example, administration of IDO inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

As used herein, the term "indoximod" refers to 1-methyl-D-tryptophan, also referred to as D-1MT or D1mT.

As used herein, the term "prodrug of indoximod" refers to any substance that after in vivo administration is metabolized to produce indoximod as one of the main metabolites.

EXAMPLES

Example 1: Reagents and Methods of Synthesis

All reagents and solvents were purchased from commercial sources. All commercial reagents and solvents were used as received without further purification. The reactions were monitored using analytical thin layer chromatography (TLC) with 0.25 mm EM Science silica gel plates (60E-254). The developed TLC plates were visualized by short wave UV light (254 nm) or immersion in potassium permanganate solution followed by heating on a hot plate. Flash chromatography was performed with Selecto Scientific silica gel, 32-63 µm particle sizes. All reactions were performed in flame or oven-dried glassware under a nitrogen atmosphere. All reactions were stirred magnetically at ambient temperature unless otherwise indicated. $^1$H NMR spectra were obtained with a Bruker DRX400, Varian VXR400 or VXR300. $^1$H NMR spectra were reported in parts per million (δ) relative to TMS (0.0), DMSO-d$_6$ (2.50) or CD$_3$OD (4.80) as an internal reference. All $^1$H NMR spectra were taken in CDCl$_3$ unless otherwise indicated.

Synthesis of ethyl 1-methyl-D-tryptophanate hydrochloride (NLG-1283)

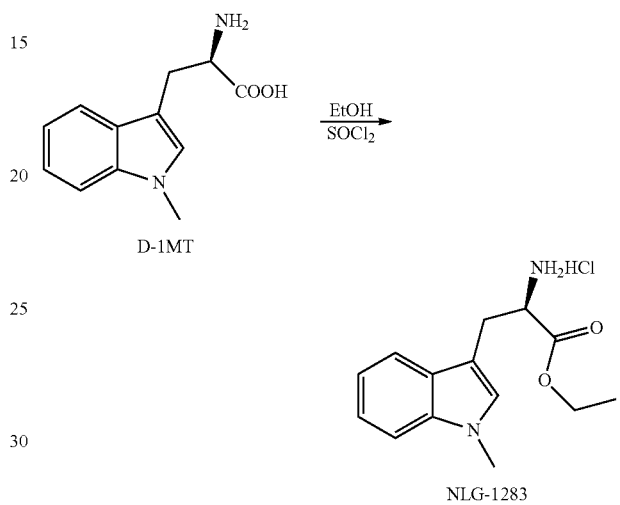

To a suspension of D-1MT (4.00 g, 18.3 mmol) in ethanol (50 mL) at 0° C. was added SOCl$_2$ (1.34 mL, 18.3 mmol) and the mixture was stirred at 80° C. overnight. After cooling to rt, the solvent was distilled-off and the crude was diluted with diethyl ether (100 mL), the white solid was filtered-off and washed with dry ether to afford the desired product (5.1 g, 98%).

Synthesis of isopropyl 1-methyl-D-tryptophanate hydrochloride (NLG-1284)

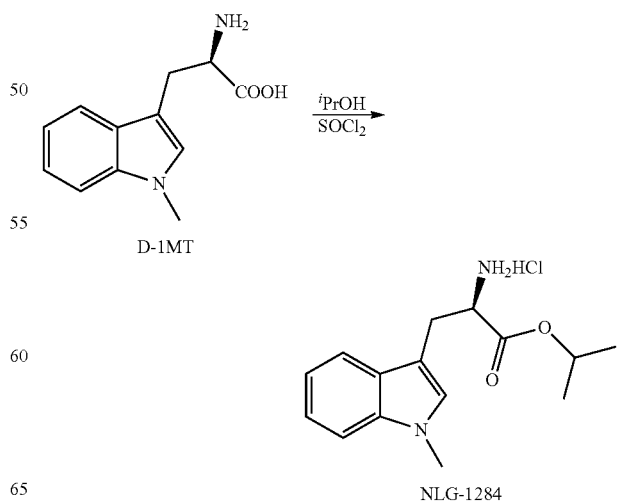

To a suspension of D-1MT (0.500 g, 2.29 mmol) in isopropanol (15 mL) at 0° C. rt, was added SOCl$_2$ (0.167 mL, 2.29 mmol) and the mixture was stirred at 80° C. overnight. After cooling to rt, the solvent was distilled-off and the crude was basified with 25% aq NaHCO$_3$ (20 mL), the product was extracted with CH$_2$Cl$_2$, the combined organic extract was dried over Na$_2$SO$_4$ and the solvent was distilled-off under reduced pressure. The free base was converted to its HCl salt by adding dry HCl in dioxane, the solvent was removed under reduced pressure to afford the desired product as white solid (0.252 g, 37%).

General Method for the Synthesis of Carbamate Esters

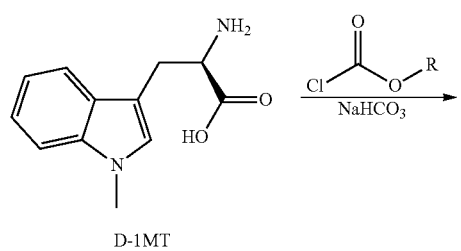

D-1MT

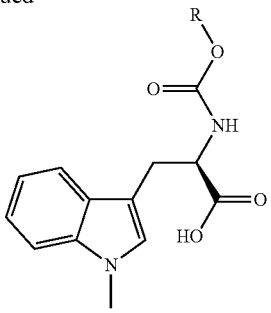

To a stirred solution of D-1MT (0.150 g, 0.687 mmol) in 1:1 THF/1M NaHCO$_3$ (2.75 mL, 2.75 mmol) was added the appropriate chloroformate dropwise. The mixture was allowed to stir for 30 min. and the solution was diluted with water and extracted with ether 2×. The aqueous layer was cooled to 0° C. and conc HCl solution was added to adjust the pH to ~1. The cold aqueous layer was immediately extracted with ethyl acetate and the combined organic layers were washed with water, brine and dried. The solvent was removed under reduced pressure to afford crude the carbamate. The crude was purified by column chromatography and treated with activated charcoal to afford the pure carbamate.

| # | Compound | Name | Yield (%) |
|---|---|---|---|
| NLG-1277 | 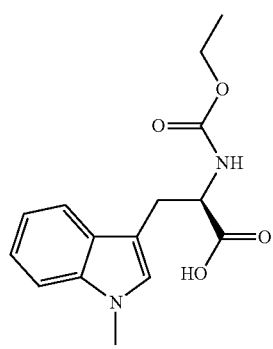 [SMILES: CCOC(=O)N[C@H](Cc1cn(C)c2ccccc12)C(=O)O] | N$^\alpha$-(ethoxycarbonyl)-1-methyl-D-tryptophan | 81 |

1.23 (t, 3H, J = 6.8 Hz), 3.63-3.71 (m, 1H), 3.74 (s, 3H), 4.07-4.12 (m, 2H), 4.69 (dd, 1H, J = 6.7, 11.6 Hz), 5.20 (dd, 1H, J = 6.9, 11.5 Hz), 6.9 (s, 1H), 7.07 (t, 1H, 6.9 Hz), 7.21-7.48 (m, 2H), 7.57 (d, 1H, J = 7.1 Hz), 9.07 (br s, 1H)

| NLG-1278 | 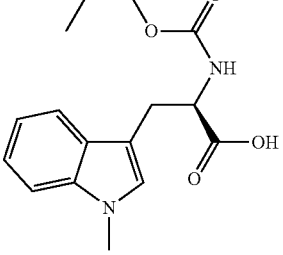 | 1-methyl-N$^\alpha$-((neopentyloxy)carbonyl)-D-tryptophan | 72 |

0.90 (s, 9H), 3.34 (s, 2H), 3.64 (s 3H), 3.73 (t, 1H, J = 6.8 Hz), 4.75 (d, 1H, J = 7.8 Hz), 5.23 (d, 1H, J = 7.9 Hz), 6.89 (s, 1H), 7.07 (t, 1H, J = 8.2 Hz), 7.25-7.59 (m overlapped with CHCl3, 2H), 7.58 (d, 1H, 7.8 Hz), 8.4 (br s, 2H)

Synthesis of N^α-(tert-butoxycarbonyl)-1-methyl-D-tryptophan

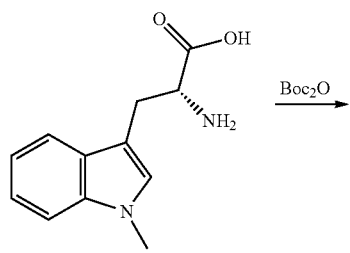

To a mixture of D-1MT (3.0 g, 13.75 mmol) in dioxane (70 mL) at 0° C. was added NaOH (550 mg dissolved in 30 mL DI water), followed by the addition of Boc$_2$O. The reaction was stirred at 0° C. for 4 h and stirred overnight at rt. The solution was concentrated under reduced pressure to approx. one third the original volume. The reaction was acidified with 1N HCl at 0° C. and the product was extracted with EtOAc. The organic extract was washed with brine and dried over Na$_2$SO$_4$, the solvent was evaporated under reduced pressure to afford the product that was used directly in the next step without further purification (4.3 g, 98%).

Synthesis of benzyl N^α-(tert-butoxycarbonyl)-1-methyl-D-tryptophanate

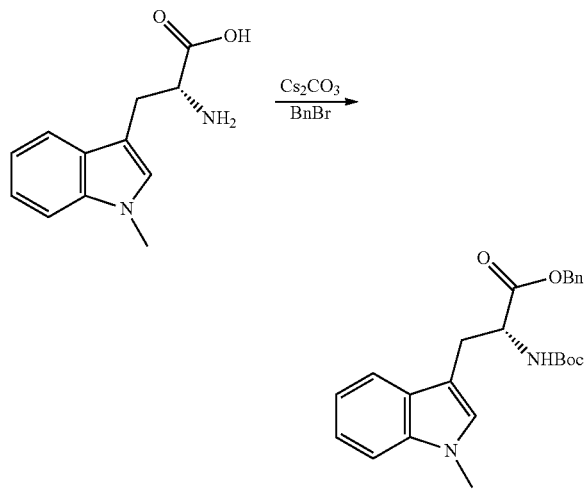

In 60 ml of DMF was dissolved N^α-(tert-butoxycarbonyl)-1-methyl-D-tryptophan (3.00 g, 9.42 mmol) to which Cs$_2$CO$_3$ (1.78 g, 5.47 mmol) and benzyl bromide (1.61 mL, 9.42 mmol) was added. The resulting suspension was allowed to stir at room temperature for 2 hours. After the end of reaction (TLC), the DMF was removed under reduced pressure followed by suspending the residue in toluene/ethyl acetate before washing with distilled water (3×50 mL) and brine. The organic layer was dried over anhydrous sodium sulfate and concentrated under vacuum. The residue was purified by column chromatography on silica gel (3.5 g, 91%).

Synthesis of benzyl 1-methyl-D-tryptophanate hydrochloride (NLG-1338)

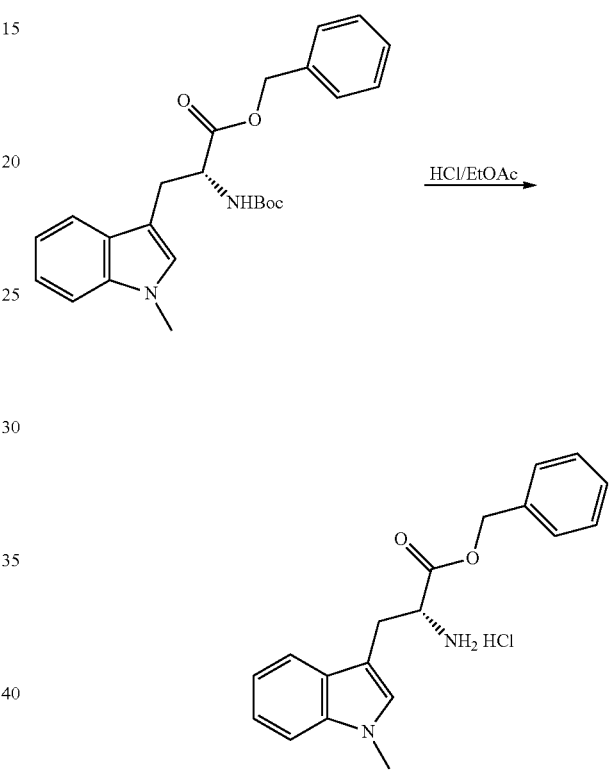

Ethyl acetate (26.9 mL) and MeOH (8.9 mL) in a RB flask equipped with a septum and a needle vent were cooled in an ice bath with stirring. Acetyl chloride (14.22 mL) was added slowly. The resulting solution was stirred at 0° C. for 20 minutes and MeOH (0.5 mL) was added. A flask containing benzyl N^α-(tert-butoxycarbonyl)-1-methyl-D-tryptophanate (3.5 g, 8.6 mmol) was placed in an ice bath and the cold, freshly prepared HCl (4M in EtOAc) was poured into the flask containing benzyl N^α-(tert-butoxycarbonyl)-1-methyl-D-tryptophanate slowly. The solution was stirred vigorously at 0° C. for 15 min where the formation of a white suspension was observed and the flask was removed from the ice bath. The suspension was allowed to stir vigorously for 2.5 h. The solution was cooled in an ice bath diluted with ether (50 mL) and the suspension was filtered and the solid cake washed with cold ether. The solid was allowed to dry under high vacuum and the desired product was isolated as a colorless solid (6.45 g, 88%). 1H NMR (d$_6$-dmdso); 3.28 (dd, 2H, J=5.6, 15.2 Hz), 3.70 (s, 3H), 4.26-4.29 (m, 1H), 5.08 (d, 1H, J=12.4 Hz), 5.13 (d, 1H, J=12.4 Hz), 7.04 (t, 1H, J=7.6 Hz), 7.06 (s, 1H), 7.10-7.18 (m, 3H), 7.30-7.35 (m, 3H), 7.42 (d, 1H, J=8 Hz), 7.53 (d, 1H, J=8 Hz).

General Scheme for the Derivatization of —COOH Group of D-1MT

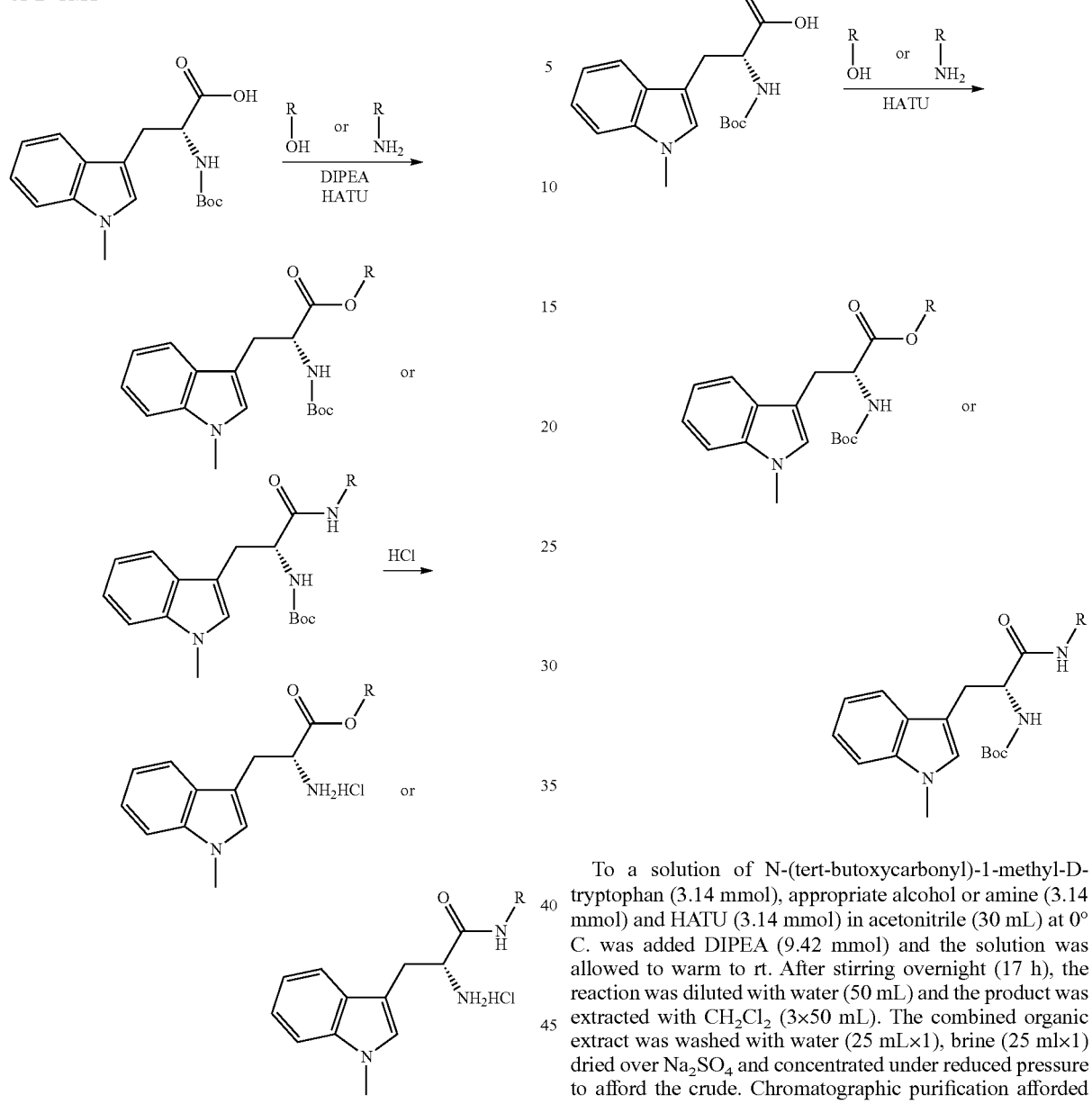

To a solution of N-(tert-butoxycarbonyl)-1-methyl-D-tryptophan (3.14 mmol), appropriate alcohol or amine (3.14 mmol) and HATU (3.14 mmol) in acetonitrile (30 mL) at 0° C. was added DIPEA (9.42 mmol) and the solution was allowed to warm to rt. After stirring overnight (17 h), the reaction was diluted with water (50 mL) and the product was extracted with $CH_2Cl_2$ (3×50 mL). The combined organic extract was washed with water (25 mL×1), brine (25 ml×1) dried over $Na_2SO_4$ and concentrated under reduced pressure to afford the crude. Chromatographic purification afforded the desired product.

| # | Compound | Name | Yield (%) |
|---|---|---|---|
| NLG-1551-B.1-E15 | | (S)-3-(tert-butoxy)-2-((tert-butoxycarbonyl)amino)-3-oxopropyl Na-(tert-butoxycarbonyl)-1-methyl-D-tryptophanate | 40 |

1.41 (s, 9H), 1.44 (s, 9H), 1.45 (s, 9H), 3.16 (dd, 1H, J = 15.3, 4.8 Hz), 3.29 (dd, 1H, J = 15.3, 4.8 Hz), 3.75 (s, 3H), 4.35-4.52 (m, 3H), 4.61 (d, 1H, J = 6.3 Hz), 4.99 (d, 1H, J = 8.6 Hz), 5.28

| # | Compound | Name | Yield (%) |
|---|---|---|---|
| | (d, 1H, J = 8.7 Hz), 6.87 (s, 1H), 7.11 (t, 1H, J = 7.3 Hz), 7.22 (t, 1H, J = 7.3 Hz), 7.29 (d, 1H, J = 8.2 Hz), 7.52 (d, 1H, J = 7.8 Hz). | | |
| NLG-1558-A-E23 | | (2,2-dimethyl-1,3-dioxolan-4-yl)methyl N-(tert-butoxycarbonyl)-1-methyl-D-tryptophanate | 78 |
| | 1.27 (s, 3H), 1.33 (s, 3H), 1.35 (s, 9 H), 3.21 (d, 2H, J = 5.6 Hz), 3.44-3.50 (m, 1H), 3.67 (s, 3H), 3.80-3.86 (m, 1H), 3.99-4.03 (m, 2H), 4.07-4.12 (m, 1H), 4.58 (q, 1H, J = 6.5 Hz), 4.99 (d, 1H, J = 8.2 Hz), 6.82 (s, 1H), 7.03 (t, 1H, J = 7.4 Hz), 7.14 (t, 1H, J = 7.4 Hz), 7.21 (d, 1H, J = 8.1 Hz), 7.47 (d, 1H, J = 8.0 Hz). | | |
| NLG-1557-B-E14 | | 2-(dimethylamino)ethyl N$^\alpha$-(tert-butoxycarbonyl)-1-methyl-D-tryptophanate | 38 |
| | 1.33 (s, 1H), 1.43 (s, 8H), 2.23 (s, 5H), 2.29 (s, 1H), 2.43-2.60 (m, 4H), 3.27 (d, J = 5.6 Hz, 2H), 3.74 (s, 3H), 4.1-4.23 (m, 2H), 4.63 (m, 1H), 5.10 (m, 1H), 6.91 (s, 1H), 7.10 (ddd, J = 8.0, 6.8, 1.2 Hz, 1H), 7.21 (ddd, J = 8.0, 6.8, 1.2 Hz, 1H), 7.28 (d, J = 8.0, 1H), 7.54 (d, J = 8.0 Hz, 1H). | | |
| NLG-1572-A-E39 | | 2-(tetrahydro-2H-pyran-4-yl)ethyl N$^\alpha$-(tert-butoxycarbonyl)-1-methyl-D-tryptophanate | 60 |
| | 1.29-1.35 (m, 2H), 1.42 (s, 9H), 1.60-1.67 (m, 5H), 3.17-3.35 (m, 4H), 3.74 (s, 3H), 3.84-3.93 (m, 2H), 4.10 (dq, 2H, J = 10.4, 6.4 Hz), 4.55-4.65 (m, 1H), 5.06 (d, 1H, J = 8.2 Hz), 6.86 (s, 1H), 7.09 (ddd, 1H, J = 8.0, 7.0, 1.1 Hz), 7.21 (ddd, 1H, J = 8.2, 6.9, 1.1 Hz), 7.28 (d, 1H, J = 7.4 Hz), 7.48-7.59 (m, 1H) | | |
| NLG-1556-A-E22 | | tert-butyl N$^\alpha$-(tert-butoxycarbonyl)-1-methyl-D-tryptophyl-L-valinate | 91 |

| # | Compound | Name | Yield (%) |
|---|---|---|---|
| | 0.69 (d, 3H, J = 6.8 Hz), 0.75 (d, 3H, J = 6.8 Hz), 1.42 (s, 18H), 1.98-2.03 (m, 1H), 3.18 (dd, 1H, J = 14.4, 7.2 Hz), 3.27-3.35 (m, 1H), 3.73 (s, 3H), 4.35-4.39 (m, 1H), 4.50 ( br s, 1H), 5.07 (br s, 1H), 6.31 (d, 1H, J = 8.8 Hz), 6.92 (s, 1H), 7.12 (t, 1H, J = 7.2 Hz), 7.22 (t, 1H, J = 7.2 Hz), 7.28 (d, 1H, J = 8.0 Hz), 7.64 (d, 1H, J = 8.0 Hz) | | |
| NLG-1561-A-E29 | | tert-butyl 4-(2-((N$^\alpha$-(tert-butoxycarbonyl)-1-methyl-D-tryptophyl)oxy)ethyl)piperidine-1-carboxylate | 92 |
| | 0.95-1.05 (m, 2H), 1.47 (s, 18H), 1.32-1.40 (m, 3H), 1.55 (d, 2H, J = 2.4 Hz), 2.59 (dt, 2H, J = 2.7, 12.8 Hz), 3.25 (d, 2H, J = 5.6 Hz), 3.74 (s, 3H), 3.99-4.05 (m, 2H), 4.94-5.00 (m, 2H), 5.08 (d, 1H, J = 8.0 Hz), 6.52 (br s, 1H), 6.86 (s, 1H), 7.09 (t, 1H, J = 7.4 Hz), 7.21 (t, 1H, J = 7.6 Hz), 7.28 (d, 1H, J = 8.0 Hz), 7.53 (d, 1H, J = 8.0 Hz). | | |
| NLG-1563-A-E30 | | tert-butyl 4-(((N$^\alpha$-(tert-butoxycarbonyl)-1-methyl-D-tryptophyl)oxy)methyl)piperidine-1-carboxylate | 83 |
| | 0.93-1.10 (m, 2H), 1.29-1.32 (m, 1H), 1.45 (s, 18H), 1.63-1.69 (m, 2H), 2.59 (tt, 2H, J = 2.4, 13.2 Hz), 3.25 (t, 2H, J = 5.4 Hz), 3.75 (s, 3H), 3.84-3.92 (m, 2H), 4.01-4.06 (m, 2H), 5.06 (d, 1H, J = 8.0 Hz), 6.35 (br s, 1H), 6.86 (s, 1H), 7.10 (dt, 1H, J = 1.2, 6.8 Hz), 7.24 (dt, 1H, J = 1.2, 6.8 Hz), 7.28 (d, 1H, J = 8.4 Hz), 7.53 (d, 1H, J = 8.0 Hz) | | |
| NLG-1578-A-E43 | | methyl N$^\alpha$-(tert-butoxycarbonyl)-1-methyl-D-tryptophylglycinate | 91 |
| | 1.25 (s, 9H), 3.15-3.25 (m, 2H), 3.67 and 3.69 (two s, 3H), 3.70 and 3.71 (two s, 3H), 3.90-3.92 (m, 2H), 5.21 and 4.48 (s, 1H), 6.54-6.52 (m, 1H), 6.93 (s, 1H), 7.13-07.03 (m, 1H), 7.14-7.30 (m, 2H), 7.59 (d, 1H, J = 8.0 Hz). | | |

Synthesis of N$^\alpha$-(tert-butoxycarbonyl)-1-methyl-D-tryptophylglycine (NLG-1579-A-E44)

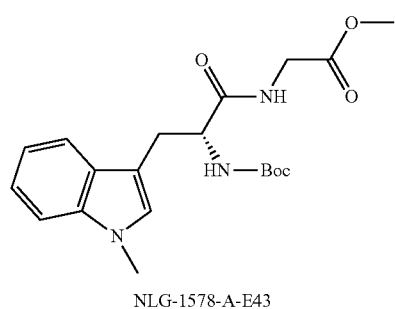

NLG-1578-A-E43

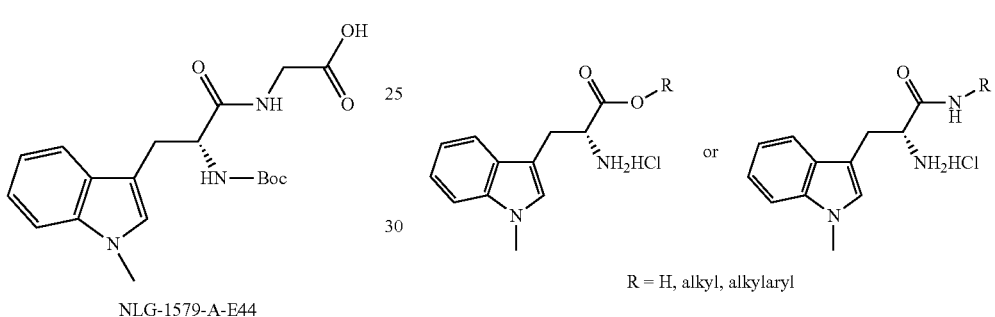

NLG-1579-A-E44

To a solution of NLG-1578-A-E43 (300 mg, 0.770 mmol) in THF (10 mL) was added water (2 mL) and lithium monohydrate (49 mg, 1.16 mmol) and the mixture stirred under ambient temperature for 2.0 h. The mixture was neutralized with 1M HCl (at 0° C.) and poured into ice cold water (20 mL). The aqueous layer was extracted with EtOAc (3×35 mL). The combined organic layers were dried over Na$_2$SO$_4$ and concentrated. The crude product was purified by flash column chromatography to afford the desired product as white solid (260 mg, 90%). $^1$H NMR: 1.25 and 1.39 (twos, 9H). 3.18-3.24 (m, 2H), 3.70 (s, 3H), 3.81-4.05 (m, 2H), 4.55 (s, 1H), 5.20-5.33 (m, 1H), 6.63 (s, 1H), 6.92 (s, 1H), 7.10 (t, 1H, J=7.2 Hz), 7.15-7.25 (m, 2H), 7.59 (dt, 1H, J=7.9 Hz)

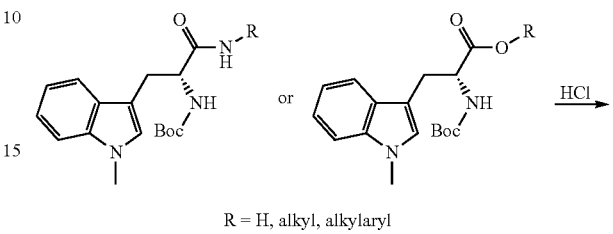

R = H, alkyl, alkylaryl

R = H, alkyl, alkylaryl

To a mixture of tBoc protected amine (1.57 mmol) in dioxane (15 mL) at rt was added HCl (4 mL, 4.0 M solution in dioxane). After stirring for 2.5 h, the solvent was distilled-off under reduced pressure. The residue was stirred with methyl tert-butyl ether (10 mL), the solid was filtered and dried under reduced pressure to afford the desired product.

The following compounds were synthesized following procedures described in the above sections.

| # | Compound | Name | Yield (%) |
|---|---|---|---|
| NLG-1557 | | 2-(dimethylamino)ethyl 1-methyl-D-tryptophanate dihydrochloride | 42 |

$^1$H NMR (400 MHz, Methanol-d$_4$): 2.69 (s, 3H), 2.77 (s, 3H), 3.46 (dd, J = 6.7, 2.1 Hz, 2H), 3.81 (s, 3H), 4.35 (m, 1H), 4.46 (t, J = 6.6 Hz, 1H), 4.54 (m, Hz, 1H), 7.11 (dd, J = 8.0 1.2 Hz, 1H), 7.18-7.25 (m, 2H), 7.40 (d, J = 8.0), 7.58 (d, J = 8.0, 1H).

| # | Compound | Name | Yield (%) |
|---|---|---|---|
| NLG-1561 | | 2-(piperidin-4-yl)ethyl 1-methyl-D-tryptophanate dihydrochloride | 64 |

(DMSO-d6) 1.24-1.45 (m, 5H), 1.60 (d, 2H, J = 13.2 Hz), 2.64-2.72 (m, 2H), 3.11-3.14 (m, 2H), 3.25 (dd, 1H, J = 14.4, 7.6 Hz), 3.33-3.83 (m, 1H, merged with H$_2$O from DMSO), 3.75 (s, 3H), 3.99-4.08 (m, 2H), 4.15 (t, 1H, J = 6.6 Hz), 7.04 (t, 1H, J = 7.4 Hz), 7.16 (t, 1H, J = 7.6 Hz), 7.24 (s, 1H), 7.42 (d, 1H, J = 8.0 Hz), 7.53 (d, 1H, J = 8.0 Hz), 8.75 (br s, 3H), 8.95 (br s, 1H), 9.16 (br s, 1H)

| # | Compound | Name | Yield (%) |
|---|---|---|---|
| NLG-1563 | | piperidin-4-ylmethyl 1-methyl-D-tryptophanate dihydrochloride | 50 |

(DMSO-d6) 1.16-1.34 (m, 2H), 1.41 (d, 1H, J = 13.6 Hz), 1.53 (d, 1H, J = 13.6 Hz), 1.61-1.66 (m, 1H), 2.66-2.70 (m, 2H), 3.08-3.16 (m, 2H), 3.22-3.28 (m, 1H), 3.36-3.44 (m, 1H), 3.74 (s, 3H), 3.78-3.88 (m, 2H), 4.12-4.17 (m, 1H), 7.05 (t, 1H, J = 7.4 Hz), 7.15 (t, 1H, J = 7.4 Hz), 7.24 (s, 1H), 7.40 (d, 1H, J = 8.0 Hz), 7.55 (d, 1H, J = 7.6 Hz), 8.83 (br s 3H), 9.06 (br s, 1H), 9.34 (br s, 1H)

| # | Compound | Name | Yield (%) |
|---|---|---|---|
| NLG-1572 | | 2-(tetrahydro-2H-pyran-4-yl)ethyl 1-methyl-D-tryptophanate hydrochloride | 94 |

$^1$H NMR (DMSO-d$_6$, 400 MHz): δ = 0.93-1.11 (m, 2H), 1.18 (d, 1H, J = 6.2 Hz), 1.26-1.43 (m, 4H), 3.14 (d, 2H, J = 11.2 Hz), 3.23 (dd, 1H, J = 14.7, 7.7 Hz), 3.29-3.39 (m, 2H), 3.69-3.78 (m, 4H), 4.04 (d, 2H, J = 6.2 Hz), 4.17 (t, 1H, J = 6.6 Hz), 7.04 (ddd, 1H, J = 8.0, 7.1, 1.0 Hz), 7.16 (ddd, 1H, J = 8.3, 7.0, 1.2 Hz), 7.23 (s, 1H), 7.42 (d, 1H, J = 8.2 Hz), 7.53 (dd, 1H, J = 8.1, 1.4 Hz), 8.69 (br s, 3H).

| # | Compound | Name | Yield (%) |
|---|---|---|---|
| NLG-1578 | | methyl 1-methyl-D-tryptophylglycinate hydrochloride | 93 |

3.12 (dd, 1H, J = 14.7, 7.8 Hz,), 3.25 (dd, 1H, J = 14.7, 5.7 Hz), 3.64 (s, 3H), 3.72 (s, 3H), 3.93 (t, 2H, J = 6.0 Hz), 3.97-4.06 (m, 1H), 7.03 (t, 1H, J = 7.5 Hz), 7.14 (t, 1H, J = 7.20 Hz), 7.19 (s, 1H), 7.39 (d, 1H, J = 8.2 Hz), 7.71 (d, 1H, J = 8.0 Hz), 8.21 (s, 2H), 9.15 (m, 1H).

Synthesis of O-(1-methyl-D-tryptophyl)-L-serine dihydrochloride (NL-G1551)

Synthesis of 1-methyl-D-tryptophyl-L-valine hydrochloride (NLG-1556)

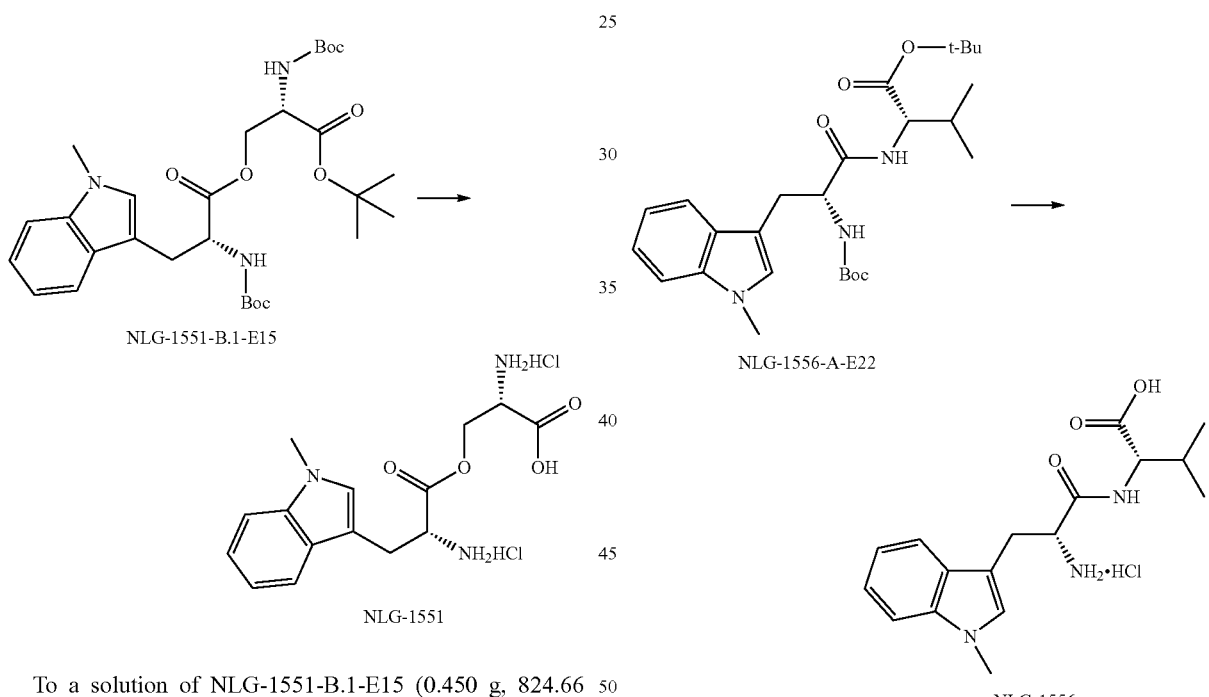

To a solution of NLG-1551-B.1-E15 (0.450 g, 824.66 mmol) in CH$_2$Cl$_2$ (10 mL) was added HCl (2 mL, 4 M solution in dioxane) at 0° C. and the solution was allowed to warm to rt. After stirring for 5 h, the solvent was evaporated and the reaction was diluted with trifluoroacetic acid (8 mL) and the solution was stirred for 7 h at rt. After evaporating trifluoroacetic acid the reaction was diluted with dry HCl solution (1 mL, 4 M solution in dioxane) and the mixture was stirred for 10 min. The solvent was evaporated under reduced pressure, the product was triturated with ethanol:ether (10:90, 15 mL) and the product was filtered and washed with dry ether (10 mL). The product was dried under reduced pressure (0.190 g, 61%). $^1$H NMR (400 MHz, CD$_3$OD): 3.22-3.28 (m, 1H), 3.43 (dd, 1H, J=15.4, 4.7 Hz), 3.70 (s, 3H), 4.23 (t, 1H, J=3.9 Hz), 4.35 (dd, 1H, J=8.0, 4.9 Hz), 4.60 (d, 2H, J=3.8 Hz), 6.99-7.04 (m, 1H), 7.05 (s, 1H), 7.09-7.16 (m, 1H), 7.29 (d, 1H, J=8.3 Hz), 7.50 (d, 1H, J=7.9 Hz).

Dioxane (7 mL) and MeOH (1.20 mL, 28.6 mmol) in a RB flask equipped with a septum and a needle vent were cooled in an ice bath with stirring. Acetyl chloride (2.00 mL, 28.6 mmol) was added slowly. The resulting solution was stirred at 0° C. for 20 minutes and MeOH (0.1 mL) was added. A flask containing NLG-1556-A-E22 (678 mg, 1.43 mmol) was placed in an ice bath and the cold, freshly prepared HCl (4M in dioxane) was poured into the flask containing NLG-1556-A-E22 slowly. The solution was allowed to warm to RT and stirred vigorously for 18 h. The solvent was removed using rotary evaporator to afford pure white solid (205 mg, 40%). (DMSO-d6) 0.71-0.77 (m, 6H), 1.91-2.00 (m, 1H), 3.08 (dd, 1H, J=14.4, 8.4 Hz), 3.23 (dd, 1H, J=14.4, 8.4 Hz), 3.73 (s, 3H), 4.12-4.17 (m, 2H), 7.06

(t, 1H, J=7.4 Hz), 7.17 (t, 1H, J=7.8 Hz), 7.20 (s, 1H), 7.40 (d, 1H, J=8.4 Hz), 7.74 (d, 1H, J=8.0 Hz), 8.2 (br s, 3H), 8.74 (d, 1H, J=8.4 Hz)

Synthesis of 2,3-Dihydroxypropyl 1-Methyl-D-Tryptophanate Hydrochloride (NLG-1558)

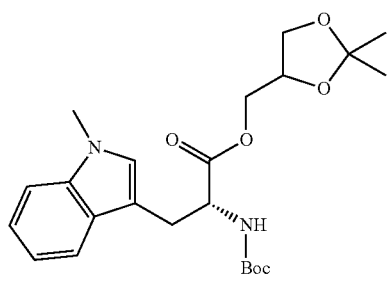 [SMILES: Cn1cc(C[C@@H](NC(=O)OC(C)(C)C)C(=O)OCC2COC(C)(C)O2)c2ccccc21]
NLG1558-A-E23

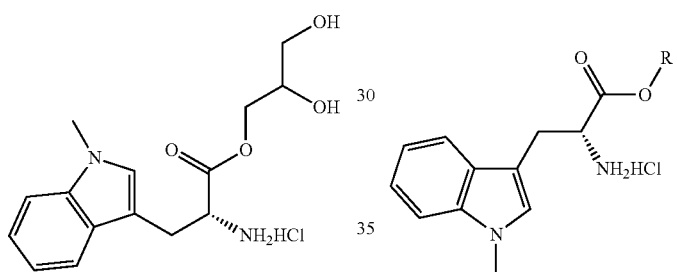
NLG-1558

A solution of NLG1558-A-E23 (11.5 g, 26.59 mmol) in THF (100 mL) at 0° C. was added TFA (16.3 mL, 212.7 mmol) and water (0.958 g, 53.18 mmol) and the cooling bath was removed, the mixture was stirred at rt for 2 h. HCl (13.3 mL, 53.18 mmol; 4.0 M solution in dioxane) was added and continued stirring for 1 h. The reaction was stirred at 40° C. for 45 minutes. The precipitated white solid was filtered and washed with MTBE to afford the hydrochloride salt (4.5 g, 51%). $^1$H NMR (400 MHz, DMSO-$d_6$): 3.32-3.40 (m, 1H), 3.44-3.52 (m, 3H), 3.76-3.86 (m, 4H), 4.16-4.37 (m, 3H), 7.10 (t, 1H, J=7.4 Hz), 7.14 (s, 1H), 7.19 (t, 1H, J=7.6 Hz), 7.38 (d, 1H, J=8.2 Hz), 7.58 (d, 1H, J=7.9 Hz).

General Scheme for the Derivatization of the —NH$_2$ and —COOH Group of D-1MT

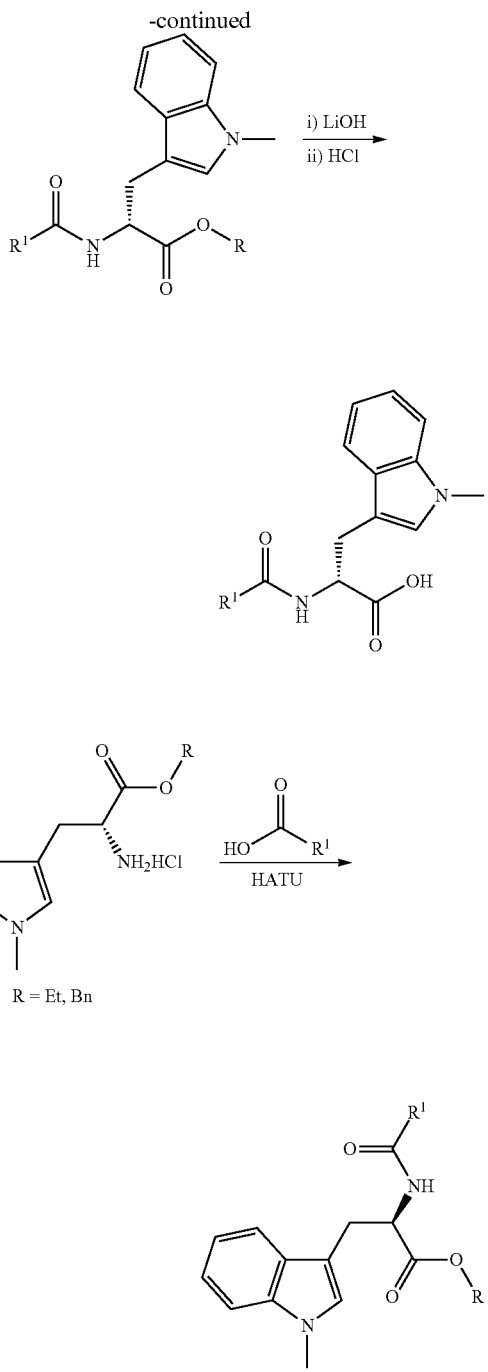

Appropriate D-tryptophanate hydrochloride ester (1.0 g, 3.54 mmol) and appropriate acid (3.54 mmol) were stirred in acetonitrile (50 mL) at 0° C. HATU (1.48 g, 3.89 mmol) and iPr$_2$NEt (2.46 mL, 14.15 mmol) were added and the reaction stirred overnight at room temperature. The solvent was removed under reduced pressure and the crude was diluted with water (50 mL) and dichloromethane (50 mL). The organic layer was separated and the aqueous layer was extracted with dichloromethane (3×50 mL). The combined organic layer was washed with brine (50 mL), dried over Na$_2$SO$_4$, and concentrated under reduced pressure. The crude product was purified by flash column chromatography to afford the desired product.

| # | Compound | Name | Yield (%) |
|---|---|---|---|
| NLG-1564-B-E31 | | ethyl N^α-((tert-butoxycarbonyl)-L-leucyl)-1-methyl-D-tryptophanate | 92 |

0.86 (dd, 6H, J = 6.2, 2.1 Hz), 1.20 (t, 3H, J = 7.1 Hz), 1.39 (s, 9H), 1.55-1.58 (m, 2H) 3.29 (d, 2H, J = 5.7 Hz), 3.74 (s, 3H), 4.03-4.18 (m, 3H), 4.79-4.86 (m, 2H), 6.60 (d, 1H, J = 7.8 Hz), 6.87 (s, 1H), 7.09 (t, 1H, J = 7.4 Hz), 7.20 (t, 1H, J = 7.5 Hz), 7.26 (s, 1H), 7.52 (d, 1H, J = 7.9 Hz)

| # | Compound | Name | Yield (%) |
|---|---|---|---|
| NLG-1565-A-E32 | | ethyl N^α-((tert-butoxycarbonyl)-L-leucyl)-1-methyl-D-tryptophanate | 93 |

0.80-0.84 (m, 6H), 1.02-0.91 (m, 2H), 1.19 (t, 3H, J = 7.1 Hz), 1.40 (s, 9H), 1.87 (m, 1H), 3.28 (t, 2H, J = 5.4 Hz), 3.72 (s, 3H), 4.00-4.04 (m, 1H), 4.05- 4.16 (m, 2H), 4.85 (q, 1H, J = 6.4 Hz), 4.95 (d, 1H, J = 9.0 Hz), 6.46 (d, 1H, J = 7.7 Hz), 6.87 (s, 1H), 7.10 (ddd, 1H, J = 8.0, 6.8, 1.1 Hz), 7.20 (ddd, 1H, J = 8.2, 6.9, 1.2 Hz), 7.26 (d, 1H, J = 8.0 Hz), 7.53 (dt, 1H, J = 7.9, 1.0 Hz).

| # | Compound | Name | Yield (%) |
|---|---|---|---|
| NLG-1566-A-E37 | | ethyl N^α-((tert-butoxycarbonyl)-L-glutaminyl)-1-methyl-D-tryptophanate | 90 |

1.16 (t, 3H, J = 7.1 H), 1.33 (s, 9H), 1.79-1.99 (m, 2H), 2.05 (ddd, 1H, J = 15.2, 6.9, 5.7 Hz), 2.18 (ddd, 1H, J = 14.8, 8.6, 5.9 Hz), 3.21 (d, 2H, J = 5.9 Hz), 3.68 (s, 3H), 4.00-4.14 (m, 3H), 4.75 (dt, 1H, J = 7.7, 5.9 Hz), 5.22 (s, 1H), 5.55 (d, 1H, J = 7.0 Hz), 5.90 (s, 1H), 6.85 (s, 1H), 6.87-6.93 (m, 1H), 7.04 (ddd, 1H, J = 8.0, 6.9, 1.1 Hz), 7.14 (ddd, 1H, J = 8.2, 6.9, 1.1 Hz), 7.17-7.21 (m, 1H), 7.45 (d, 1H, J = 7.9 Hz).

| # | Compound | Name | Yield (%) |
|---|---|---|---|
| NLG-1574-A-E40 | | ethyl N$^\alpha$-((tert-butoxycarbonyl)-L-phenylalanyl)-1-methyl-D-tryptophanate | 80 |

1.14 (t, 3H, J = 7.1 H), 1.29 (s, 9H), 2.82 (s, 2H), 2.91-3.02 (m, 1H), 3.03-3.10 (m, 2H), 3.25 (dd, 1H, J = 14.78, 5.2 Hz), 3.67 (s, 3H), 3.99-4.07 (m, 2H), 4.33 (br s, 1H), 4.79 (q, 1H, J = 6.2 Hz), 6.37 (d, 1H, J = 7.8 Hz), 6.57 (s, 1H), 7.06 (ddd, 1H, J = 8.0, 6.8, 1.2 Hz), 7.14-7.25 (m, 6H), 7.41 (d, 1H, J = 7.9 Hz).

| # | Compound | Name | Yield (%) |
|---|---|---|---|
| NLG-1585-A-E45 | | methyl N$^2$-(tert-butoxycarbonyl)-N$^4$-((R)-1-ethoxy-3-(1-methyl-1H-indol-3-yl)-1-oxopropan-2-yl)-L-asparaginate | 71 |

1.18 (t, 3H, J = 7.2 Hz), 1.39 (s, 9H), 2.63 (dd, 1H, J = 17.1, 6.1 Hz), 2.95 (dd, 1H, J = 17.2, 4.4 Hz), 3.29 (d, 2H, J = 5.8 Hz), 3.62 (s, 3H), 3.74 (s, 3H), 4.03-4.13 (m, 2H), 4.53 (br s, 1H), 4.79-4.83 (m, 1H), 5.61 (d, 1H, J = 9.0 Hz), 6.88 (s, 1H), 7.01-7.10 (m, 2H), 7.19 (ddd, 1H, J = 8.2, 6.9, 1.2 Hz), 7.24-7.27 (m, 1H), 7.51 (m, 1H).

| # | Compound | Name | Yield (%) |
|---|---|---|---|
| NLG-1546-B-E20 | | ethyl Nα-((tert-butoxycarbonyl)-D-tryptophyl)-1-methyl-D-tryptophanate | 97 |

1.18 (t, 3H, J = 7.1 Hz), 1.38 (s, 9H), 1.73 (br s, 1H), 3.13 (dd, 2H, J = 5.4, 2.5 Hz), 3.32 (s, 1H), 3.57 (s, 3H), 4.05 (dd, 2H, J = 17.2, 7.2 Hz), 4.43 (s, 1H), 4.72-4.80 (m, 1H), 5.07 (s, 1H), 6.22 (s, 1H), 6.42 (s, 1H), 6.90 (s, 1H), 6.97 (s, 1H), 7.04-7.25 (m, 5H), 7.33 (d, J = 8.2 Hz, 1H), 7.66 (d, J = 7.8 Hz, 1H), 7.87 (s, 1H)

-continued

| # | Compound | Name | Yield (%) |
|---|----------|------|-----------|
| NLG-1549-A-E26 | | ethyl Nα-(Nα-(tert-butoxycarbonyl)-1-methyl-D-tryptophyl)-1-methyl-D-tryptophanate | 95 |

1.16 (t, 3H, J = 7.1 Hz), 1.37 (s, 9H), 3.02-3.20 (m, 3H), 3.35 (d, 1H, J = 15.0 Hz), 3.57 (s, 3H), 3.68 (s, 3H), 3.94-4.10 (m, 2H), 4.42 (br s, 1H), 4.75 (d, 1H, J = 6.8 Hz), 5.04 (s, 1H), 6.24 (br s, 1H), 6.37 (s, 1H), 6.84 (br s, 1H), 6.94 (s, 1H), 7.08-7.18 (m, 3H), 7.17-7.25 (m, 2H), 7.27-7.33 (m, 1H), 7.65 (d, 1H, J = 7.9 Hz)

| NLG-1560-B-E28 | | ethyl Nα-((tert-butoxycarbonyl)-L-tryptophyl)-1-methyl-D-tryptophanate | 97 |

1.12 (t, 3H, J = 7.1 Hz), 1.39 (s, 9H), 2.90 (d, 1H, J = 15.2 Hz), 3.05-3.32 (m, 3H), 356 (s, 3H), 3.91-04.10 (m, 2H), 4.44 (br s, 1H), 4.75 (br s, 1H), 5.15 (br s, 1H), 6.18 (d, 1H, J = 7.8 Hz), 6.27 (s, 1H), 6.86 (d, 1H, J = 2.3 Hz), 7.04 (ddd, 1H, J = 8.0, 6.8, 1.2 Hz), 7.14 (ddd, 1H, J = 8.0, 7.1, 1.2 Hz), 7.16-7.27 (m, 3H), 7.30 (dt, 1H, J = 8.1, 1.0 Hz), 7.37 (d, 1H, J = 8.2 Hz), 7.68 (d, 1H, J = 7.7 Hz), 7.80 (s, 1H)

| NLG-1553-B-E21 | | ethyl Nα-((tert-butoxycarbonyl)-L-valyl)-1-methyl-D-tryptophanate | 95 |

0.80 (d, 3H, J = 6.8 Hz), 0.87 (d, 3H, J = 6.8 Hz), 1.19 (t, 3H, J = 7.2 Hz), 1.40 (s, 9H) 2.09-2.17 (m, 1H), 3.25-3.32 (m, 2H), 3.74 (s, 3H), 3.94-3.97 (m, 1H), 4.09-4.15 (m, 2H), 4.84-4.89 (m, 1H), 4.93-4.95 (m, 1H), 6.45 (d, 1H, J = 7.6 Hz), 6.87 (s, 1H), 7.10 (t, 1H, J = 7.4 Hz), 7.21 (t, 1H, J = 7.6 Hz), 7.27 (d, 1H, J = 7.6 Hz), 7.53 (dd, 1H, J = 8.0, 1.2 Hz)

| NLG-1554-A-E25 | | ethyl Nα-((tert-butoxycarbonyl)glycyl)-1-methyl-D-tryptophanate | 94 |

1.22 (t, 3H, J = 7.2 Hz), 1.42 (s, 9H), 3.31 (d, 2H, J = 5.2 Hz), 3.72-3.77 (m, 2H), 3.74 (s, 3H), 4.07-4.17 (m, 2H), 4.86-4.91 (m, 1H), 5.04 (br s, 1H), 6.50 (d, 1H, J = 7.6 Hz), 6.86 (s, 1H), 7.10 (t, 1H, J = 7.4 Hz), 7.21 (t, 1H, J = 7.4 Hz), 7.28 (d, 1H, J = 8.0 Hz), 7.50 (d, 1H, J = 7.6 Hz)

-continued

| # | Compound | Name | Yield (%) |
|---|----------|------|-----------|
| NLG-1555-A-E27 | | ethyl N^α-((tert-butoxycarbonyl)-L-alanyl)-1-methyl-D-tryptophanate | 95 |

1.20 (t, 3H, J = 7.0 Hz), 1.29 (d, 3H, J = 7.2 Hz), 1.40 (s, 9H), 3.30 (d, 1H, J = 5.6 Hz) 3.75 (s, 3H), 4.09-4.16 (m, 3H), 4.81-4.86 (m, 1H), 4.93 (br s, 1H), 6.61 (br s, 1H), 6.87 (s, 1H), 7.09 (t, 1H, J = 7.4 Hz), 7.21 (t, 1H, J = 7.6 Hz), 7.27 (d, 1H, J = 8.4 Hz, merged with chloroform), 7.52 (d, 1H, J = 8.0 Hz)

| # | Compound | Name | Yield (%) |
|---|----------|------|-----------|
| NLG-1548-A-E18 | | benzyl N$^2$-(N$^2$,N$^6$-bis(tert-butoxycarbonyl)-L-lysyl)-1-methyl-D-tryptophanate | 91 |

$^1$H NMR (400 MHz, Chloroform-d) δ 1.25 (q, J = 7.7 Hz, 2H), 1.39 (s, 9H), 1.44 (s, 9H), 1.47-1.55 (m, 1H), 1.67-1.80 (m, 2H), 3.02 (t, J = 6.7 Hz, 2H), 3.29 (d, J = 5.5 Hz, 2H), 3.66 (s, 3H), 4.04 (s, 1H), 4.53 (s, 1H), 4.90 (q, J = 6.1 Hz, 1H), 4.97 (s, 1H), 5.09 (q, J = 12.2 Hz, 2H), 6.57 (d, J = 7.8 Hz, 1H), 6.64 (s, 1H), 7.08 (t, J = 7.4 Hz, 1H), 7.20 (t, J = 7.6 Hz, 1H), 7.23-7.29 (m, 4H overlapped with CHCl$_3$), 7.30-7.39 (m, 3H), 7.49 (d, J = 7.9 Hz, 1H).

| # | Compound | Name | Yield (%) |
|---|----------|------|-----------|
| NLG-1547-D-E17 | | tert-butyl (S)-5-(((R)-1-(benzyloxy)-3-(1-methyl-1H-indol-3-yl)-1-oxopropan-2-yl)amino)-4-((tert-butoxycarbonyl)amino)-5-oxopentanoate | 93 |

δ 1.38 (s, 9H), 1.43 (s, 9H), 1.76-1.91 (m, 1H), 1.94-2.09 (m, 1H), 2.20 (dt, J = 16.6, 7.0 Hz, 1H), 2.31 (dt, J = 16.6, 7.3 Hz, 1H), 3.19-3.36 (m, 2H), 3.67 (s, 3H), 4.90 (dt, J = 8.1, 5.6 Hz, 1H), 5.00-5.14 (m, 2H), 5.19 (s, 1H), 6.70 (s overlapping m, 2H), 7.08 (ddd, J = 8.0, 6.9, 1.2 Hz, 1H), 7.18-7.28 (m, 4H), 7.29-7.37 (m, 2H), 7.50 (dt, J = 8.0, 1.0 Hz, 1H).

| # | Compound | Name | Yield (%) |
|---|---|---|---|
| DD-00508-B-E078 | | ethyl N$^\alpha$-((tert-butoxycarbonyl)-L-methionyl)-1-methyl-D-tryptophanate | 84 |

δ 1.21 (t, J = 7.2 Hz, 3H), 1.40 (s, 9H), 1.79-1.89 (m, 1H), 1.94-2.00 (m, 1H) 2.01 (s, 3H), 2.31-2.36 (m, 1H), 2.36-2.46 (m, 1H), 3.30 (dd, J = 5.7, 3.6 Hz, 2H), 3.75 (s, 3H), 4.12 (q, J = 7.2 Hz, 2H), 4.26 (d, J = 7.5 Hz, 1H), 4.84 (q, J = 6.4 Hz, 1H), 5.17 (d, J = 8.3 Hz, 1H), 6.67 (d, J = 7.2 Hz, 1H), 6.89 (s, 1H), 7.10 (t, J = 7.4 Hz, 1H), 7.21 (t, J = 7.2 Hz, 1H), 7.28 (d, J = 7.5 Hz, 1H), 7.53 (d, J = 7.9 Hz, 1H).

Synthesis of N$^\alpha$—((S)-5-(tert-butoxy)-2-((tert-butoxycarbonyl)amino)-5-oxopentanoyl)-1-methyl-D-tryptophan (NLG-1547-E.2-E17)

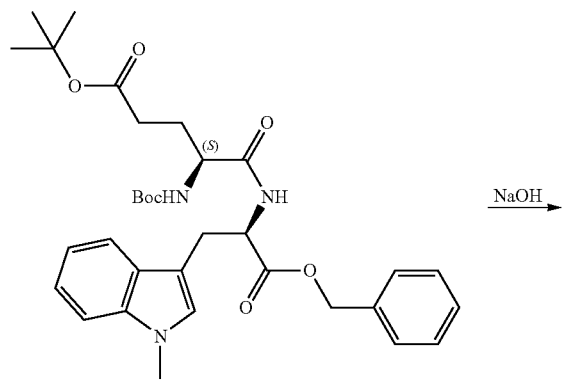

NLG-1547-D-E17 tert-Butyl(S)-5-(((R)-1-(benzyloxy)-3-(1-methyl-1H-indol-3-yl)-1-oxopropan-2-yl)amino)-4-((tert-butoxycarbonyl)amino)-5-oxopentanoate (800 mg, 1.38 mmol) was suspended in MeOH (8 mL) and THF (8 mL). After cooling to 0° C., NaOH sol'n (2.4 mL, 2M) was added and the reaction stirred for 1 h. The solution was acidified with 1M HCl to pH=4 and the solvents were concentrated under reduced pressure (40° C.). The solution was partitioned between water and DCM in a separatory funnel and the organic layer was collected. The aqueous layer was extracted with DCM (2×15 mL) and the combined organic layer was washed with water and brine. Chromatographic purification afforded the desired product (0.502 g, 72%). $^1$H NMR (Chloroform-d, 400 MHz): δ=1.38 (s, 9H), 1.44 (s, 9H), 1.68-1.81 (m, 1H), 1.84-1.99 (m, 1H), 2.12-2.33 (m, 3H), 3.23-3.42 (m, 2H), 4.23 (s, 3H), 4.86 (d, 1H, J=6.9 Hz), 5.41 (d, 1H, J=8.6 Hz), 6.83 (d, 1H, J=7.5 Hz), 6.93 (s, 1H), 7.09 (dt, 1H, J=8.0, 1.2 Hz), 7.18 (t, 1H, J=7.8 Hz), 7.23 (apparent d overlapped with CDCl$_3$, 1H), 7.60 (d, 1H, J=7.9 Hz).

Synthesis of (S)-4-amino-5-(((R)-1-carboxy-2-(1-methyl-1H-indol-3-yl)ethyl)amino)-5-oxopentanoic acid hydrochloride (NLG-1547)

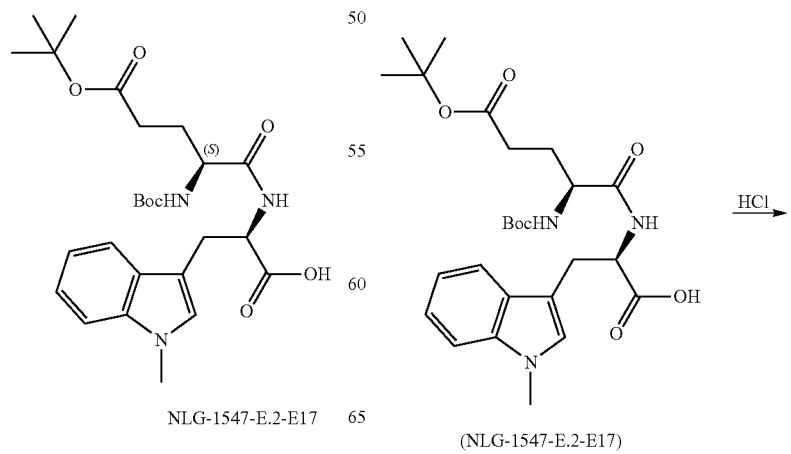

-continued

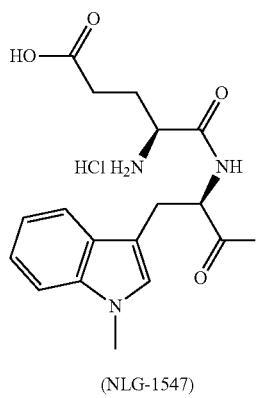

(NLG-1547)

To Nα—((S)-5-(tert-butoxy)-2-((tert-butoxycarbonyl)amino)-5-oxopentanoyl)-1-methyl-D-tryptophan (470 mg, 0.93 mmol) was added HCl (4M in dioxane) (4.7 mL). The resulting solution was allowed to stir at room temperature for 5 hours. The solution was concentrated and the solid was dissolved in MeOH and treated with activated charcoal and heated to 60° C. for 1 h. The solution was filtered through celite and the filtrate concentrated to afford the desired product as a beige solid (0.304, 85%). $^1$HNMR (DMSO-$d_6$, 400 MHz): (mixture of rotamers) 1.73-2.21 (m, 4H), 2.93-3.12 (m, 1H), 3.14-3.27 (m, 1H), 3.70 (s, 3H), 3.83 (q, 1H, J=5.8 Hz), 4.53-4.72 (m, 1H), 7.01 (tt, 1H, J=7.3, 3.7 Hz), 7.07-7.19 (m, 2H), 7.35 (dt, 1H, J=7.5, 3.5 Hz), 7.44-7.61 (m, 1H), 8.42 (br s, 3H), 8.83-9.10 (m, 1H).

General Method for the Hydrolysis of Substituted D-1MT Ethyl Esters

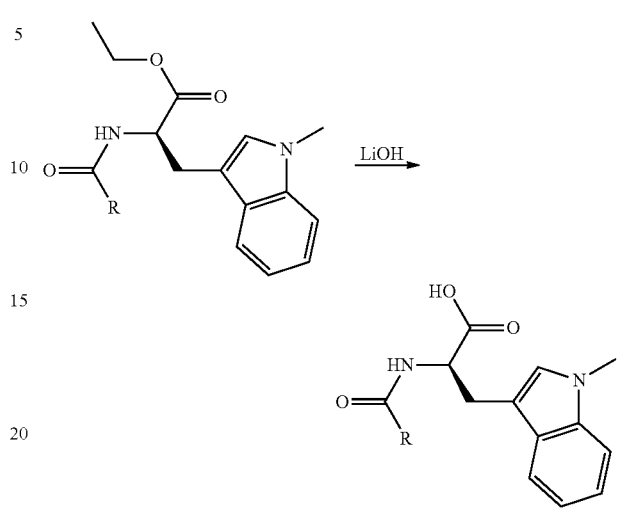

To a solution of appropriate amide (0.991 mmol) in THF (10 mL) was added water (3 mL) and lithium monohydrate (67 mg, 1.59 mmol) and the mixture stirred under ambient temperature for 2 h. The mixture was neutralized with 1M HCl (at 0° C.) and poured into ice cold water (20 mL). The aqueous layer was extracted with EtOAc (3×35 mL). The combined organic layers were dried over $Na_2SO_4$ and concentrated. The crude product was purified by flash column chromatography to afford the desired product.

| # | Compound | Name | Yield (%) |
|---|----------|------|-----------|
| NLG-1570-A-E33 | ![structure] 0.76-0.96 (m, 6H), 1.39 (s, 9H), 1.40-1.54 (m, 3H), 3.29 (dd, 1H, J = 15.1, 5.3 Hz), 3.40 (dd, 1H, J = 14.9, 5.7 Hz), 3.70 (s, 3H), 4.41 (td, 1H, J = 9.3, 5.4 Hz), 4.86 (q, 1H, J = 6.7, 5.8 Hz), 5.26 (d, 1H, J = 9.1 Hz), 6.88 (br s, 1H), 7.05-7.11 (m, 1H), 7.14-7.28 (m, 3H), 7.59 (d, 1H, J = 7.9 Hz) | Nα-((tert-butoxycarbonyl)-L-leucyl)-1-methyl-D-tryptophan | 87 |
| NLG-1548-B-E18 | ![structure] | Nα-($N^2,N^6$-bis(tert-butoxycarbonyl)-L-lysyl)-1-methyl-D-tryptophan | 91 |

| # | Compound | Name | Yield (%) |
|---|---|---|---|
| | 1.05-1.20 (m, 2H), 1.37 (s, 9H), 1.44 (s, 9H), 1.65-1.80 (m, 2H), 2.98 (br d, 2H), 3.15-3.51 (m, 2H), 3.69 (s, 3H), 3.84-4.04 (m, 1H), 4.15 (d, 1H, J = 7.6 Hz), 4.69 (s, 1H), 4.85 (d, 1H, J = 6.6 Hz), 5.43 (s, 1H), 5.73-6.18 (m, 2H), 6.91 (s, 1H), 7.06 (t, 1H, J = 7.4 Hz), 7.18 (t, 1H, J = 7.5 Hz), 7.24 (d, 1H, J = 8.3 Hz), 7.60 (d, 1H, J = 7.9 Hz). | | |
| NLG1571-A-E34 | | $N^\alpha$-((tert-butoxycarbonyl)-L-isoleucyl)-1-methyl-D-tryptophan | 88 |
| | 0.75-0.88 (m, 8 H), 1.37 (s, 9H), 1.62-1.70 (m, 1H), 3.13-3.17 and 3.30-3.32 (two m, 2H), 3.65 and 3.70 (two s, 3H), 4.89-4.92 (m, 1H), 5.33 (d, 1H, J = 9.2 Hz), 6.79 (t, 1H, J = 7.1 Hz), 6.92 (s, 1H), 7.08 (t, 1H, J = 7.4 H), 7.19 (t, 1H, J = 7.7 Hz), 7.25 (d, 1H, J = 6.8 Hz), 7.56 and 7.62 (two d, 1H, J = 8.0 Hz). | | |
| NLG1569-A-E38 | | $N^\alpha$-((tert-butoxycarbonyl)-L-glutaminyl)-1-methyl-D-tryptophan | 83 |
| | 1.34 (s, 9H), 1.59 (dd, 1H, J = 14.1, 7.9 Hz), 1.73-1.77(m, 1H), 1.94-2.04 (m, 2H), 3.02 (dd, 1H, J = 14.6, 7.9 Hz), 3.13 (dd, 1H, J = 14.5, 5.2 Hz,), 3.69 (s, 3H), 3.90-3.96 (m, 1H), 4.40-4.45 (m, 1H), 6.72 (s, 1H), 6.80 (d, 1H, J = 8.3 Hz), 6.96-7.02 (m, 1H), 7.05 (s, 1H), 7.10 (ddd, 1H, J = 8.2, 7.0, 1.1 Hz), 7.18 (s, 1H), 7.34 (d, 1H, J = 8.2 Hz), 7.51 (d, 1H, J = 7.9 Hz), 7.98 (d, 1H, J = 7.9 Hz), 12.70 (br s, 1H). | | |
| NLG1575-A-E41 | | $N^\alpha$-((tert-butoxycarbonyl)-L-phenylalanyl)-1-methyl-D-tryptophan | 75 |
| | 1.30 (s, 9H), 2.81-2.88 (m, 1H), 2.94-3.00 (m, 1H), 3.08 (dd, 1H, J = 14.8, 5.8 Hz), 3.21-3.25 (m, 1H), 3.66 (s, 3H), 4.41 (d, 1H, J = 6.7 Hz), 4.79-4.86 (m, 1H), 5.13 (d, 1H, J = 8.3 Hz), 6.56 (d, 1H, J = 6.5 Hz), 6.63 (s, 1H), 6.95-7.25 (m, 8H), 7.46 (d, 1H, J = 7.9 Hz). | | |

| # | Compound | Name | Yield (%) |
|---|---|---|---|
| NLG-1546-C-E20 | | N$^\alpha$-((tert-butoxycarbonyl)-D-tryptophyl)-1-methyl-D-tryptophan | 84 |

1.31 (s, 9H), 3.05-3.13 (m, 3H), 3.29 (s, 1H), 3.55 (s, 3H), 4.44 (s, 1H), 4.75 (q, J = 6.1 Hz, 1H), 5.10 (s, 1H), 6.26 (s, 1H), 6.58 (s, 1H), 6.89 (s, 2H), 7.07-7.24 (m, 5H), 7.31 (d, 1H, J = 8.0 Hz), 7.64 (d, 1H, J = 6.6 Hz), 8.09-8.35 (m, 1H)

| NLG-1549-B-E26 | | N$^\alpha$-(N$^\alpha$-(tert-butoxycarbonyl)-1-methyl-D-tryptophyl)-1-methyl-D-tryptophan | 40 |

1.27 (s, 9H), 2.99 (dd, 1H, J = 14.7, 5.4 Hz), 3.09 (dd, 1H, J = 14.3, 6.7 Hz), 3.16 (dd, 1H, J = 14.8, 5.2 Hz), 3.25-3.44 (m, 1H), 3.57 (s, 3H), 3.69 (s, 3H), 4.39 (br s, 1H), 4.76 (dt, 1H, J = 8.1, 5.5 Hz), 5.01 (br s, 1H), 6.29 (br s, 1H), 6.53 (s, 1H), 6.79 (br s, 1H), 6.91 (s, 1H), 6.97 (br s, 2H), 7.07-7.18 (m, 2H), 7.20 (d, 1H, J = 8.2 Hz), 7.21-7.34 (m overlapped with CDCl$_3$, 2H), 7.62 (d, 1H, J = 7.9 Hz)

| NLG-1560-C.1-E28 | | N$^\alpha$-((tert-butoxycarbonyl)-L-tryptophyl)-1-methyl-D-tryptophan | 91 |

1.35 (s, 9H), 3.08 (2.79-3.25, 4H), 3.50 (s, 3H), 3.71-3.79 (m, 1H), 4.31-4.55 (m, 1H), 4.62-4.96 (m, 1H), 6.45 (s, 1H), 6.70-6.91 (m, 1H), 6.98-7.06 (m, 1H), 7.08 (t, 1H, J = 7.5 Hz), 7.12-7.25 (m, 4H), 7.44 (q, 2H, J = 8.8 Hz), 7.56 (d, 1H, J = 7.9 Hz), 8.02 (br s, 1H).

| NLG-1553-C-E21 | | N$^\alpha$-((tert-butoxycarbonyl)-L-valyl)-1-methyl-D-tryptophan | 100 |

0.77 (d, 3H, J = 6.8 Hz), 0.81 (d, 3H, J = 6.4 Hz), 1.38 (s, 9H), 1.84-1.92 (m, 1H), 3.30-3.32 (m, 1H), 3.66-3.77 (m, 4H), 4.08-4.12 (m, 1H), 4.88-4.92 (m, 1H), 5.23 (d, 1H, J = 9.2 Hz), 6.66 (d, 1H, J = 7.2 Hz), 6.92 (s, 1H), 7.09 (t, 1H, J = 7.4 Hz), 7.20 (t, 1H, J = 7.6 Hz), 7.26 (d, 1H, J = 8.4 Hz, merged with chloroform), 7.62 (d, 1H, J = 8.0 Hz)

| # | Compound | Name | Yield (%) |
|---|---|---|---|
| NLG-1554-B-E25 | | $N^\alpha$-((tert-butoxycarbonyl)glycyl)-1-methyl-D-tryptophan | 83 |

1.39 (s, 9H), 3.25-3.35 (m, 2H) 3.2-3.74 (m, 5H), 4.85-4.90 (m, 1H), 5.21 (br s, 1H), 6.63 (br s, 1H), 6.90 (s, 1H), 7.08 (t, 1H, J = 7.4 Hz), 7.17-7.27 (m, 2H, merged with chloroform), 7.55 (d, 1H, J = 7.6 Hz)

| # | Compound | Name | Yield (%) |
|---|---|---|---|
| NLG-1555-B-E27 | | $N^\alpha$-((tert-butoxycarbonyl)-L-alanyl)-1-methyl-D-tryptophan | 86 |

1.21 (d, 3H, J = 7.2 Hz), 1.38 (s, 9H), 3.19-3.38 (m, 3H), 3.73 (s, 3H), 4.22-4.27 (m, 1H), 4.84 (br s, 1H), 6.77 (br s, 1H), 6.87 (s, 1H), 7.08 (t, 1H, J = 7.4 Hz), 7.19 (t, 1H, J = 7.4 Hz), 7.24 (d, 1H, J = 8.8 Hz, merged with chloroform), 7.57 (d, 1H, J = 7.6 Hz)

| # | Compound | Name | Yield (%) |
|---|---|---|---|
| DD00510-A-E079 | | $N^\alpha$-((tert-butoxycarbonyl)-L-methionyl)-1-methyl-D-tryptophan | 92 |

1.36 (s, 9H), 1.68-1.87 (m, 2H), 1.94 and 2.01 (s, 3H), 2.25-2.43 (two m, 2H), 3.23 (dd, J = 14.9, 6.5 Hz, 1H), 3.36 (dd, J = 14.6, 4.8 Hz, 1H), 3.71 (s, 3H), 4.23-4.34 (two m, 1H), 4.82-4.94 (two m, 1H), 5.52 (d, J = 6.7 Hz, 1H), 6.79-6.99 (m, 2H), 7.09 (t, J = 7.4 Hz, 1H), 7.19 (t, J = 7.4 Hz, 1H), 7.25 (d, J = 6.1 Hz, 1H), 7.58 (d, J = 8.0 Hz 1H)

General Method for ′Boc Deprotection.

To a solution of appropriate ′Boc protected amine (0.707 mmol) in dioxane (2 mL) was added HCl solution (1.77 mL, 4.0 M solution in dioxane) at 0° C. The solution was allowed to warm to rt and stirred vigorously for 2.5-18 h. The solvent was removed using rotary evaporator. The solid was diluted with dry ether (15 mL) and the product was filtered to afford the crude product. The crude was dried under high vacuum to afford the desired product.

| # | Compound | Name | Yield (%) |
|---|---|---|---|
| NLG-1546 | | N$^\alpha$-(D-tryptophyl)-1-methyl-D-tryptophan hydrochloride | 95 |

$^1$H NMR (400 MHz, Methanol-d$_4$) δ 3.15 (d, J = 8.5 Hz, 1H), 3.19 (d, J = 8.5 Hz, 1H), 3.36 (d, 1H, J = 4.9 Hz), 3.37-3.41 (m, 1H), 3.71 (s, 3H), 4.06 (t, 1H, J = 3.6 Hz), 4.74 (s, 1H), 6.93 (s, 1H), 7.02 (t, 1H, J = 6.2 Hz), 7.04-7.07 (m, 1H), 7.14 (td, 2H, J = 7.9, 1.7 Hz), 7.20 (s, 1H), 7.22 (d, J = 8.1 Hz, 1H), 7.30 (d, 1H, J = 8.2 Hz), 7.38 (d, 1H, J = 8.1 Hz), 7.56 (d, 1H, J = 8.0 Hz), 7.65 (d, 1H, J = 7.9 Hz), 7.70 (d, 1H, J = 8.2 Hz)

| # | Compound | Name | Yield (%) |
|---|---|---|---|
| NLG-1548 | | N$^\alpha$-(L-lysyl)-1-methyl-D-tryptophan dihydrochloride | 87 |

$^1$H NMR (400 MHz, DMSO-d$_6$): 0.88-1.13 (m, 2H), 1.33-1.56 (m, 4H), 2.54 (t, 2H, J = 7.1 Hz), 2.95-3.10 (m, 1H), 3.15-3.24 (m, 1H), 3.42 (apparent q overlapping with H$_2$O, 1H, J = 7.0 Hz), 3.73 (s, 3H), 4.50-4.67 (m, 1H), 7.01 (t, 1H, J = 7.5 Hz), 7.06-7.18 (m, 2H), 7.38 (d, 1H, J = 8.3 Hz), 7.55 (d, 1H, J = 7.9 Hz), 8.02 (br s, 3H), 8.20 (br s, 3H), 8.83 (d, 1H, J = 8.1 Hz), 12.93 (br s, 1H)

| # | Compound | Name | Yield (%) |
|---|---|---|---|
| NLG-1549 | | 1-methyl-N$^\alpha$-(1-methyl-D-tryptophyl)-D-tryptophan hydrochloride | 92 |

$^1$H NMR (400 MHz, DMSO-d$_6$): 3.10 (td, 2H, J = 15.5, 7.9 Hz), 3.24 (ddd, 2H, J = 17.5, 15.1, 5.9 Hz), 3.72 (s, 2H), 3.73 (s, 4H), 4.02 (dd, 1H, J = 8.3, 5.1 Hz), 4.58 (q, 1H, J = 7.0 Hz), 7.04 (td, 2H, J = 7.4, 4.2 Hz), 7.09-7.23 (m, 4H), 7.40 (t, 2H, J = 8.1 Hz), 7.58 (d, 1H, J = 7.9 Hz), 7.74 (d, 1H, J = 7.9 Hz), 8.11 (s, 1H), 8.97 (d, 1H, J = 7.7 Hz), 12.82 (br s, 1H)

| # | Compound | Name | Yield (%) |
|---|---|---|---|
| NLG-1553 | | N$^\alpha$-(L-valyl)-1-methyl-D-tryptophan hydrochloride | 92 |

$^1$H NMR (400 MHz, DMSO-d$_6$): 0.54 (d, 3H, J = 7.2 Hz), 0.72 (d, 3H, J = 6.8 Hz), 1.89-1.94 (m, 1H), 3.01 (dd, 1H, J = 14.8, 9.6 Hz), 3.22 (dd, 1H, J = 14.6, 5.0 Hz), 3.56-3.65 (m, 1H), 3.70 (s,

| # | Compound | Name | Yield (%) |
|---|---|---|---|
| | 3H), 4.61-4.66 (m, 1H), 7.01 (t, 1H, J = 7.6 Hz), 7.12 (s, 1H), 7.12 (t, 1H, J = 7.6 Hz), 7.36 (t, 1H, J = 8.0 Hz), 7.56 (d, 1H, J = 8.0 Hz), 8.09 (br s, 3H), 8.78 (d, 1H, J = 8.4 Hz), 12.8 (br s, 1H) | | |
| NLG-1554 | | N$^\alpha$-glycyl-1-methyl-D-tryptophan hydrochloride | 87 |
| | $^1$H NMR (400 MHz, DMSO-d$_6$): 3.02-3.08 (m, 1H), 3.17-3.22 (m, 1H), 3.48-3.60 (m, 2H), 3.74 (s, 3H), 4.55-4.58 (m, 1H), 7.03 (t, 1H, J = 7.8 Hz), 7.12-7.18 (m, 2H), 7.38 (d, 1H, J = 8.0 Hz), 7.55 (d, 1H, J = 8.0 Hz), 8.13 (br s, 3H), 8.76 (d, 1H, J = 8.0 Hz), 12.87 (br s, 1H) | | |
| NLG-1555 | | N$^\alpha$-(L-alanyl)-1-methyl-D-tryptophan hydrochloride | 44 |
| | $^1$H NMR (400 MHz, DMSO-d$_6$): 1.18 (d, 3H), 3.02-3.06 (m, 1H), 3.17-3.23 (m, 1H), 3.72 (s, 3H), 4.05-4.09 (m, 1H), 4.57-4.62 (m, 1H), 7.02 (t, 1H, J = 7.6 Hz), 7.12-7.15 (m, 2H), 7.38 (d, 1H, J = 8.0 Hz), 7.52 (d, 1H, J = 7.6 Hz), 8.16 (br s, 3H), 8.88-8.92 (m, 1H) | | |
| NLG-1560 | | N$^\alpha$-(L-tryptophyl)-1-methyl-D-tryptophan hydrochloride | 90 |
| | $^1$H NMR (400 MHz, DMSO-d$_6$): δ = 2.88 (dd, 1H, J = 14.7, 8.2 Hz), 2.98 (dd, 1H, J = 14.5, 7.9 Hz), 3.08 (dt, 2H, J = 14.7, 5.0 Hz), 3.63 (s, 3H), 4.06 (br s, 1H), 4.55 (q, 1H, J = 7.9), 6.87 (dd, 1H, J = 8.0, 7.0 Hz), 6.97 (s, 1H), 7.01 (t, 1H, J = 7.4 Hz), 7.06 (t, 1H, J = 7.4 Hz), 7.08-7.15 (m, 2H), 7.34 (d, 2H, J = 8.2 Hz), 7.56 (dd, 2H, J = 8.0, 5.1 Hz), 8.09 (s, 3H), 8.95 (d, 1H, J = 8.1 Hz), 11.02 (s, 1H) | | |
| NLG-1564 | | ethyl N$^\alpha$-(L-leucyl)-1-methyl-D-tryptophanate hydrochloride | 93 |
| | $^1$H NMR (400 MHz, DMSO-d$_6$): 0.70 (t, 6H, J = 5.7 Hz). 1.13 (t, 3H, J = 7.1 Hz), 1.38-1.23 (m, 3H), 3.01 (dd, 1H, J = 14.5, 9.4 Hz), 3.18 (dd, 1H, J = 14.5, 5.2 Hz), 3.70 (s, 3H), 4.08 (q, 2H, J = 7.1 Hz), 4.62-4.53 (m, 1H), 7.00 (ddd, 1H, J = 7.8, 7.0, 1.0 Hz), 7.09-7.13 (m, 2H), 7.36 (d, 1H, J = 8.2 Hz), 7.50 (dd, 1H, J = 7.6, 1.1 Hz), 8.18 (br s, 3H), 8.99 (d, 1H, J = 8.1 Hz). | | |

| # | Compound | Name | Yield (%) |
|---|---|---|---|
| NLG-1565 | | ethyl N$^\alpha$-(L-isoleucyl)-1-methyl-D-tryptophanate hydrochloride | 93 |

$^1$H NMR (400 MHz, DMSO-d$_6$): 0.60-0.66 (m, 6H), 0.75-0.82 (m, 2H), 1.12 (t, 3H, J = 7.1 Hz, 4H), 1.63 (br s, 1H), 3.02 (dd, 1H, J = 14.6, 9.4 Hz), 3.17 (dd, 1H, J = 14.6, 5.2 Hz), 3.61 (br s, 1H), 3.69 (s, 3H), 4.07 (q, 2H, J = 7.1 Hz), 4.62 (br s, 1H), 7.01 (t, 1H, J = 7.5 Hz), 7.10-7.14 (m, 2H), 7.36 (d, 1H, J = 8.2 Hz), 7.49 (d, 1H, J = 7.9 Hz), 8.00 (br s, 2H), 8.85 (br s, 1H).

| # | Compound | Name | Yield (%) |
|---|---|---|---|
| NLG-1566 | | ethyl N$^\alpha$-(L-glutaminyl)-1-methyl-D-tryptophanate hydrochloride | 59 |

$^1$H NMR (400 MHz, DMSO-d$_6$): 1.08 (t, 3H, J = 7.1 Hz), 1.81-1.97 (m, 2H), 2.01-2.12 (m, 2H), 3.07 (dd, 1H, J = 14.4, 8.4 Hz), 3.16 (dd, 1H, J = 14.4, 6.0 Hz), 3.70 (s, 3H), 3.82 (t, 1H, J = 6.0 Hz), 4.03 (q, 2H, J = 7.1 Hz), 4.53 (q, 1H, J = 7.0 Hz), 6.93 (s, 1H), 7.02 (ddd, 1H, J = 7.9, 7.0, 1.0 Hz), 7.09-7.14 (m, 2H), 7.35 (d, 1H, J = 8.2 Hz), 7.40 (s, 1H), 8.24 (br s, 3H), 9.01 (d, 1H, J = 7.2 Hz).

| # | Compound | Name | Yield (%) |
|---|---|---|---|
| NLG-1567 | | ethyl N$^\alpha$-(D-tryptophyl)-1-methyl-D-tryptophanate hydrochloride | 97 |

$^1$H NMR (400 MHz, DMSO-d$_6$): 1.19 (t, 3H, J = 7.1 Hz), 1.91 (br s, 2H), 2.87 (m, 1H), 3.25 (d, 2H, J = 5.6 Hz), 3.33 (dd, 1H, J = 14.5, 4.4 Hz), 3.66 (s, 3H), 3.70 (dd, 1H, J = 9.0, 4.7 Hz), 4.10 (m, 1H), 4.87 (dt, 1H, J = 8.5, 5.5 Hz), 6.71 (d, 1H, J = 8.5 Hz), 6.95 (d, 1H, J = 2.6 Hz), 7.00-7.10 (m, 2H), 7.12-7.22 (m, 2H), 7.24 (d, 2H, J = 6.1 Hz), 7.32 (d, 1H, J = 8.1 Hz), 7.51 (d, 1H, J = 7.7 Hz), 7.60 (d, 1H, J = 8.0 Hz), 7.66 (d, 1H, J = 8.3 Hz), 8.15 (s, 1H).

| # | Compound | Name | Yield (%) |
|---|---|---|---|
| NLG-1569 | | N$^\alpha$-(L-glutaminyl)-1-methyl-D-tryptophan hydrochloride | 97 |

$^1$H NMR (400 MHz, DMSO-d$_6$): 1.79-1.84 (m, 2H), 1.95-2.06 (m, 2H), 3.04 (dd, 1H, J = 14.6, 8.5 Hz), 3.19 (dd, 1H, J = 14.6, 5.2 Hz), 3.49-3.35 (m, 2H), 3.70 (s, 3H), 3.78-3.88 (m, 1H), 4.53 (td, 1H, J = 8.3, 5.2 Hz), 6.93 (s, 1H), 7.00 (ddd, 1H, J = 8.0, 7.0, 1.0 Hz), 7.16-7.07 (m, 2H), 7.35 (dt, 1H, J = 8.3, 0.9 Hz), 7.38 (s, 1H), 7.54 (dt, 1H, J = 7.9, 1.0 Hz), 8.28 (d, 2H, J = 4.2 Hz), 8.87 (d, 1H, J = 8.1 Hz).

| NLG-1570 | | N$^\alpha$-(L-leucyl)-1-methyl-D-tryptophan hydrochloride | 95 |

$^1$H NMR (400 MHz, DMSO-d$_6$): 0.68 (t, 6H, J = 5.5 Hz). 1.34-1.17 (m, 3H), 2.99 (dd, 1H, J = 14.5, 9.6 Hz), 3.20 (dd, 1H, J = 14.6, 4.7 Hz), 3.34-3.40 (m, 3H), 3.68 (s, 3H), 4.52-4.62 (m, 1H), 6.99 (t, 1H, J = 7.4 Hz), 7.16-7.08 (m, 2H), 7.35 (d, 1H, J = 8.2 Hz), 7.54 (d, 1H, J = 7.9 Hz), 8.17 (br s, 2H), 8.85 (d, 1H, J = 8.3 Hz).

| NLG-1571 | | N$^\alpha$-(L-isoleucyl)-1-methyl-D-tryptophan hydrochloride | 94 |

$^1$H NMR (400 MHz, DMSO-d$_6$): 0.55-0.65 (m, δ H), 0.71-0.75 (m, 1H), 1.03-1.12 (m, 1H), 1.57-1.63 (m, 1H), 2.99 (dd, 1H, J = 14.6, 9.8 Hz), 3.19 (dd, 1H, J = 14.6, 4.7 Hz), 3.61-3.63 (m, 1H), 3.69 (s, 3H), 4.58-4.64 (m, 1H), 7.0 (t, 1H, J = 7.6 Hz), 7.08-7.13 (m, 2H), 7.35 (d, 1H, J = 8.2 Hz), 7.53 (d, 1H, J = 7.9 Hz), 8.10 (br s, 3H), 8.72 (d, 1H, J = 8.1 Hz).

| NLG-1574 | | ethyl N$^\alpha$-(L-phenylalanyl)-1-methyl-D-tryptophanate hydrochloride | 60 |

| # | Compound | Name | Yield (%) |
|---|---|---|---|

¹H NMR (400 MHz, DMSO-d₆): 1.15 (t, 3H, J = 7.1 Hz), 2.52 (dd, 1H, J = 13.7, 9.9 Hz), 3.17-3.23 (m, 3H), 3.46 (dd, 1H, J = 9.9, 4.1 Hz), 3.64 (s, 3H), 4.03-4.11 (m, 2H), 4.83 (dt, 1H, J = 8.4, 5.6 Hz), 6.72 (s, 1H), 6.99 (ddd, 1H, J = 8.0, 6.9, 1.1 Hz), 7.31-7.05 (m, 7H), 7.45 (d, 1H, J = 7.9 Hz), 7.61 (d, 1H, J = 8.4 Hz)

| NLG-1575 | | N^α-(L-phenylalanyl)-1-methyl-D-tryptophan hydrochloride | 91 |

¹H NMR (400 MHz, DMSO-d₆): 2.78 (dd, 1H, J = 13.9, 7.1 Hz), 2.89-2.97 (m, 2H), 3.10 (dd, 1H, J = 14.5, 5.3 Hz), 3.35 (br s, 3H), 3.47 (s, 3H), 4.05 (dd, 1H, J = 7.1, 5.6 Hz), 4.51 (td, 1H, J = 8.2, 5.3 Hz), 6.92-6.94 (m, 2H), 6.99-7.18 (m, 6H), 7.36 (dt, J = 8.3, 0.9 Hz, 1H), 7.56 (dt, J = 8.0, 0.9 Hz, 1H), 8.89 (d, J = 8.1 Hz, 1H).

| NLG-1579 | | 1-Methyl-D-tryptophylglycine hydrochloride | 90 |

¹H NMR (400 MHz, Methanol-d₄): 3.25 (dd, 2H, J = 14.8, 7.9 Hz), 3.43 (dd, 1H, J = 14.8, 6.1 Hz), 3.77 (s, 3H), 3.92 (d, 2H, J = 5.5 Hz), 4.14-4.19(m, 1H), 7.09 (t, 1H, J = 7.5 Hz), 7.16-7.24 (m, 2H), 7.36 (d, 1H, J = 8.1 Hz), 7.67 (d, 1H, J = 7.9 Hz).

| NLG-1585 | | methyl N⁴-((R)-1-ethoxy-3-(1-methyl-1H-indol-3-yl)-1-oxopropan-2-yl)-L-asparaginate hydrochloride | 92 |

¹H NMR (400 MHz, DMSO-d₆): 1.12 (t, 3H, J = 7.1 Hz), 2.64-2.76 (m, 2H), 3.06 (dd, 1H, J = 14.5, 8.2 Hz), 3.17 (dd, 1H, J = 14.6, 5.9 Hz), 3.58 (s, 3H), 3.73 (s, 3H), 4.04-4.13 (m, 3H), 4.57 (td, 1H, J = 8.0, 5.9 Hz), 7.02 (ddd, 1H, J = 8.0, 7.0, 1.0 Hz), 7.12-7.16 (m, 2H), 7.39 (dt, 1H, J = 8.3, 0.9 Hz), 7.51 (dt, 1H, J = 8.0, 1.0 Hz), 8.27 (s, 3H), 9.00 (d, 1H, J = 7.8 Hz)

| # | Compound | Name | Yield (%) |
|---|---|---|---|
| NLG-3272-01 | | ethyl N$^\alpha$-(L-methionyl)-1-methyl-D-tryptophanate hydrochloride | 90 |

$^1$H NMR(DMSO-d$_6$, 400 MHz): δ (ppm) 1.69 (t, J = 7.1 Hz, 3H), 2.44 (s, 3H), 2.61-2.82 (m 2H), 3.59 (dd, J = 14.5, 9.5 Hz, 1H), 3.74 (dd, J = 14.6, 5.0 Hz, 1H), 4.27 (s, 3H), 4.37 (s, 1H), 4.63 (q, J = 7.1 Hz, 2H), 5.05-5.22 (m, 1H), 7.56 (t, J = 7.4 Hz, 1H), 7.62-7.75 (m, 2H), 7.91 (d, J = 8.2 Hz, 1H), 8.05 (d, J = 7.8 Hz, 1H), 8.86 (s, 2H), 9.60 (d, J = 7.8 Hz, 1H).

| # | Compound | Name | Yield (%) |
|---|---|---|---|
| NLG-3380-01 | | N$^\alpha$-(L-methionyl)-1-methyl-D-tryptophan hydrochloride | 76 |

$^1$H NMR(DMSO-d$_6$, 400 MHz): δ (ppm) 1.73-1.77 (m, 2H), 1.88 (s, 3H), 2.11-2.17 (m, 2H), 3.03 (dd, J = 14.6, 9.3 Hz, 1H), 3.24 (dd, J = 14.6, 4.7 Hz, 1H), 3.73 (s, 3H), 3.78 (t, J = 5.7 Hz, 1H), 4.51-4.67 (m, 1H), 7.02 (t, J = 7.4 Hz, 1H), 7.11-7.15 (m, 2H), 7.37 (d, J = 8.1 Hz, 1H), 7.56 (d, J = 8.1 Hz, 1H), 8.78 (br s, 1H)

Synthesis of (2-ethoxy-2-oxido-1,3,2-dioxaphospholan-4-yl)methyl 1-methyl-D-tryptophanate hydrochloride (NLG-1559)

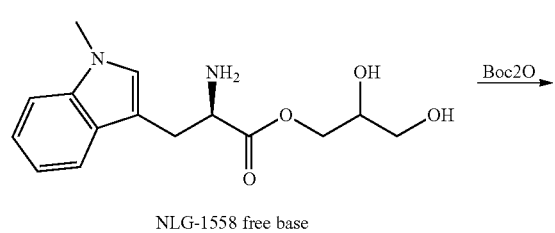

NLG-1558 free base

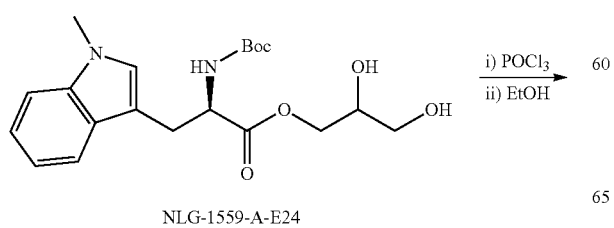

NLG-1559-A-E24

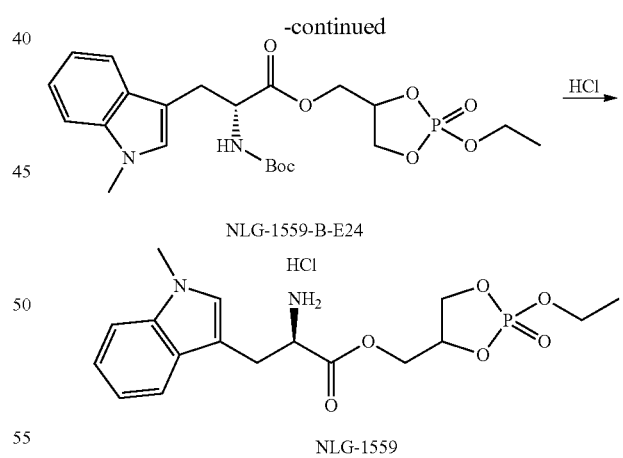

NLG-1559-B-E24

NLG-1559

2,3-dihydroxypropyl N$^\alpha$-(tert-butoxycarbonyl)-1-methyl-D-tryptophanate (NLG-1559-A-E24)

To a solution NLG-1558 free base (0.750 mg, 2.57 mmol) in acetonitrile (10 mL) at 0° C. was added Boc$_2$O (560 mg, 2.57 mmol) and the reaction was allowed to warm to RT and stirred for 4 h. The solvent was removed under reduced pressure and the crude was purified by column chromatography to afford the desired product (760 mg, 75%). $^1$H NMR: 1.34 (s, 9H), 3.13-3.23 (m, 2H, 3.35-3.38 (m, 1H), 3.42-3.45 (m, 1H), 3.67-3.72 (m, 4H), 4.01-4.08 (m, 2H), 5.01-5.04 (m, 1H), 6.83 (s, 1H), 7.05 (t, 1H, J=7.4 Hz), 7.16 (t, 1H, J=7.3 Hz), 7.23 (d, 1H, J=8.2 Hz), 7.49 (d, 1H, J=7.9 Hz).

(2-ethoxy-2-oxido-1,3,2-dioxaphospholan-4-yl) methyl Na-(tert-butoxycarbonyl)-1-methyl-D-tryptophanate (NLG-1559-B-E24)

To a solution of NLG-1559-A-E24 (650 mg, 1.66 mmol) in dry pyridine (2 mL) at 0° C. was added POCl$_3$ and the solution was allowed to warm to rt. After stirring overnight (18 h), ethanol (1.5 mL) was added and the reaction continued for 4 h. The solvent was removed under reduced pressure and the crude was purified by column chromatography (460 mg, 57%). $^1$H NMR: 1.13 (t, 3H, J=7.0 Hz), 1.30 (s, 9H), 3.10-3.20 (m, 2H), 3.47-3.55 (m, 1H), 3.60 (s, 3H), 41.9-4.44 (m, 3H), 4.55-4.57 (m, 1H), 5.23-5.27 (m, 1H), 6.79 and 6.83 (two s, 1H), 7.01 (t, 1H, J=7.4 Hz), 7.12 (t, 1H, J=7.2 Hz), 7.18 (d, 1H, J=9.2 Hz), 7.46 (d, 1H, J=7.7 Hz).

(2-Ethoxy-2-oxido-1,3,2-dioxaphospholan-4-yl) methyl 1-methyl-D-tryptophanate hydrochloride (NLG-1559)

To a solution NLG-1559-B-E24 (550 mg, 1.14 mmol) in dry CH$_2$Cl$_2$ (10 mL) at 0° C. was added anhydrous HCl (1.4 mL, 4 M solution in dioxane) and the mixture was allowed to warm to rt. After stirring for 2 h, the solvent was removed under reduced pressure and the crude was washed with dry ether (3×15 mL). The white solid was filtered and the product was dried under reduced pressure (0.241 g, 61%). (CD30D-d$_4$) 1.20 (td, 3H, J=7.1, 4.3 Hz), 3.26-3.42 (m, 2H), 3.44 (dd, 1H, J=5.1, 3.0 Hz), 3.48-3.56 (m, 1H), 3.71 (s, 3H), 3.95 (h, 2H, J=7.1 Hz), 4.21-4.36 (m, 3H), 4.37-4.53 (m, 1H), 7.02 (t, 1H, J=7.4 Hz), 7.07 (d, 1H, J=4.0 Hz), 7.10-7.17 (m, 1H), 7.30 (d, 1H, J=8.2 Hz), 7.49 (d, 1H, J=7.4 Hz).

Pharmaceutically Acceptable Salt Composition(s)

Synthesis of (R)-1-carboxy-2-(1-methyl-1H-indol-3-yl)ethan-1-aminium chloride (NLG-1607)

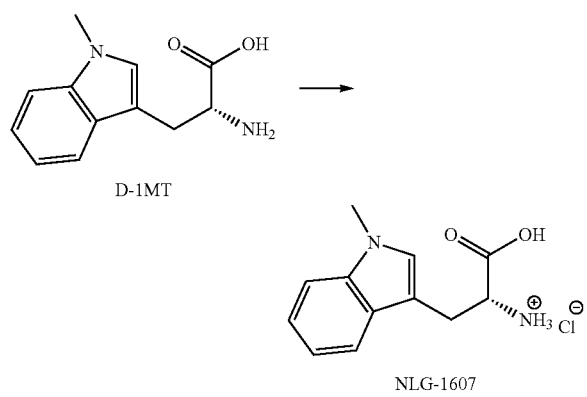

NLG-1607

To an ice cold aqueous HCl (15.5 mL, 30.9 mmol; 2M) solution was added D1MT (4.5 g, 20.6 mmol). After stirring for 30 minutes, the clear solution was evaporated under reduced pressure and the crude was evaporated thrice with Ethanol (40 mL). The crude was stirred in Ethanol and tert-butylmethylether and filtered to afford the desired product (4.25 g, 81%).

An alternative method was developed where ~10 g of D-1MT was suspended in 250 mL glass bottle with 100 mL of acetonitrile. 10 mL HCl solution pre-dissolved in acetonitrile (511.2 mg/mL) was added into the D-1MT free form solution according to 1:1 molar ratio to free base:acid, and then kept shaking at room temperature overnight to form salt. The filtered solid was dried under vacuum at 30° C. overnight. A white powder (11.1 g) was obtained by the above process, and characterized by)(RFD, DSC and TGA (FIGS. 1-2). The purity was 99.7% area based on the HPLC analysis, and the stoichiometry was analyzed by ELSD, the calculated molar ratio (API:HCl acid) were 1:1.0. The powder was crystalline as assessed by polarized light microscopy (PLM) and by X-ray powder dispersion spectrometry (XRPD, FIG. 1). The salt was anhydrous as assessed by thermogravimetric analysis (TGA) and differential scanning calorimetry (DSC) (FIG. 2).

Synthesis of (R)-1-carboxy-2-(1-methyl-1H-indol-3-yl)ethan-1-aminium methanesulfonate (NLG-1619)

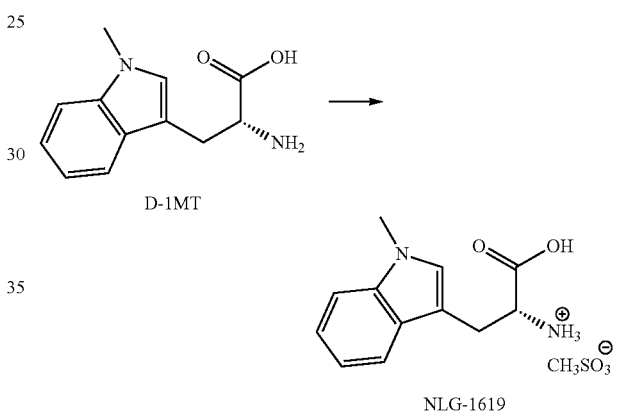

NLG-1619

To a stirred solution methane sulfonic acid (1.50 mL, 22.9 mmol) in DI water (50 mL) was added D-1MT (1.0 g, 4.48 mmol) in 100 mg portions. The solution was stirred vigorously for 3 h at 75° C. until the solution was homogeneous. The solution was concentrated under reduced pressure and the solid collected (1.38 g, 96%). $^1$H NMR (Methanol-d$_4$, 400 MHz): δ=2.69 (s, 3H), 3.32-3.39 (m, 1H), 3.49 (dd, 1H, J=15.3, 4.9 Hz), 3.80 (s, 3H), 4.25 (dd, 1H, J=7.8, 4.9 Hz), 7.10 (ddd, 1H, J=8.0, 7.0, 1.0 Hz), 7.14 (s, 1H), 7.21 (ddd, 1H, J=8.2, 7.0, 1.1 Hz), 7.38 (dd, 1H, J=8.3, 1.1 Hz), 7.62 (dt, 1H, J=8.0, 0.9 Hz)

Synthesis of (R)-1-carboxy-2-(1-methyl-1H-indol-3-yl)ethan-1-aminium dihydrogen phosphate (NLG-1660)

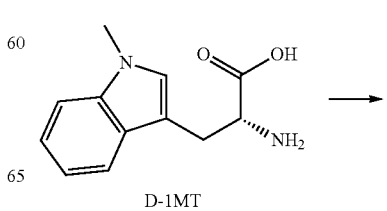

D-1MT

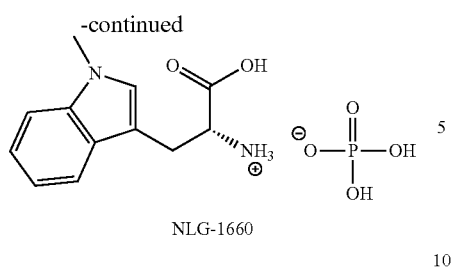

NLG-1660

To the solution of phosphoric acid (0.673 g, 6.87 mmol) in deionized water (30 mL) at 50° C., was added D-1MT (0.5 g, 2.29) portion wise and the mixture was stirred at 50° C. overnight. Solution was then concentrated to half of its original volume and allowed to stand at room temperature overnight. Resulting precipitate was filtered, washed with cold ethanol, and dried to yield NLG-1660 as white solid (0.250, 34%). $^1$H NMR (400 MHz, DMSO-d$_6$) δ 2.95 (dd, 1H, J=15.1, 8.6 Hz), 3.22-3.29 (m, 1H), 3.46 (dd, 1H, J=8.6, 4.2 Hz), 3.71 (s, 3H), 7.00 (ddd, 1H, J=8.0, 7.1, 1.0 Hz), 7.09-7.15 (m, 2H), 7.37 (d, 1H, J=8.4 Hz), 7.55 (d, 1H, J=7.9 Hz).

An alternative method was developed where ~10 g of D-1MT was suspended in 500 mL glass bottle with 100 mL of THF. 20 mL of H$_3$PO$_4$ solution pre-dissolved in THF (792.3 mg/mL) was added into the D-1MT free form solution according to 1:3 molar ratio to free base:acid, and then kept shaking at room temperature overnight to form salt. The filtered solid was dried under vacuum at 30° C. overnight, checked by XRPD, DSC, TGA and ELSD. A white powder (11.1 g) was obtained, which showed to be crystalline by PLM and XRPD pattern (FIG. 3). The salt was anhydrous based on DSC and TGA data (FIG. 4). The purity was 99.8%, and the stoichiometry was analyzed by ELSD, the calculated molar ratio (free base:phosphoric acid) were 1:0.57.

Synthesis of (R)-1-carboxy-2-(1-methyl-1H-indol-3-yl)ethan-1-aminium hydrogen sulfate (NLG-1667)

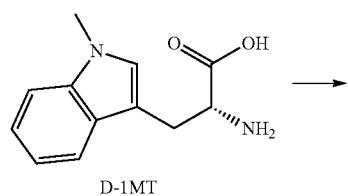

D-1MT

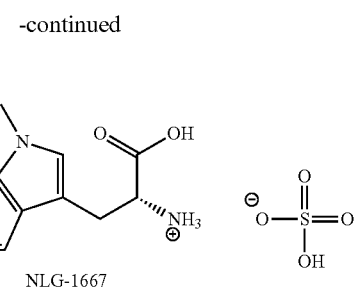

NLG-1667

To a suspension of D-1MT (1.00 g, 4.58 mmol) in water/THF (4:1, 100 mL) at rt, was added 0.5M H$_2$SO$_4$ (9.16 mL, 4.58 mmol) and the mixture was stirred at rt overnight. The white solid was filtered-off and washed with cold THF to afford the sulfate salt of D-1MT (0.429 g, 34%). (DMSO-d$_6$) 3.17 (dd, 1H, J=15.1, 7.2 Hz), 3.27 (dd, 1H, J=15.0, 5.3 Hz), 3.74 (s, 3H), 3.96 (t, 1H, J=6.2 Hz), 7.04 (t, 1H, J=7.4 Hz), 7.12-7.21 (m, 2H), 7.41 (d, 1H, J=8.2 Hz), 7.58 (d, 1H, J=8.0 Hz), 8.52 (br s, 4H).

General Method for the Generation of Mono and Di Phosphate Salts of Indoximod Prodrugs.

To a solution of free base (0.747 mmol) in EtOH (5 ml) at 0° C. was added phosphoric acid (0.747 mmol; a solution in EtOH 1 mL) or (1.494 mmol in case of diamine) and the mixture was allowed to warm to RT and stirred for 5-18 h. The solvent was removed under reduced pressure and the residue was diluted with methyl tert-butylether (10 mL), after stirring for 1-5 h the solid was filtered and dried under reduced pressure to afford the desired product. For NLG-03380-02, the free base was generated from NLG-03380-01 using ion-exchange resin.

| # | Compound | Name | Yield (%) |
|---|---|---|---|
| NLG-1626 | ![structure] | (2R)-1-(2,3-dihydroxypropoxy)-3-(1-methyl-1H-indol-3-yl)-1-oxopropan-2-aminium dihydrogen phosphate | 44 |

$^1$H NMR (DMSO-d$_6$, 400 MHz): 3.07-3.15 (m, 2H), 3.27-3.38 and 3.43-3.50 (m, 2H), $^1$H NMR (400 MHz, DMSO-d$_6$): 3.60-3.68 (m, 1H), 3.73 (s, 3H), 3.84 (br s, 1H), 3.90-3.96 (m, 1H), 4.02-4.12 (m, 1H), 6.95 (br s, 3H), 7.02 (ddd, 1H, J = 8.0. 70. 1.0 Hz), 7.11-7.19 (m, 2H), 7.38 (dt, 1H, J = 8.3, 0.9 Hz), 7.49-7.56 (m, 1H).

| # | Compound | Name | Yield (%) |
|---|---|---|---|
| NLG-1629 | 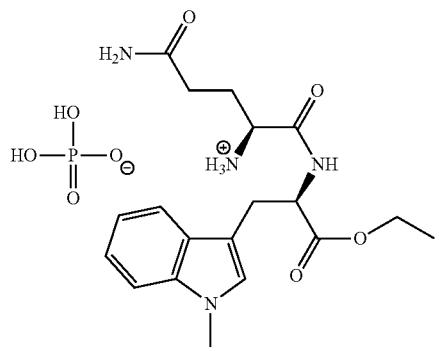 [SMILES: O=P([O-])(O)O ; CCOC(=O)[C@@H](Cc1cn(C)c2ccccc12)NC(=O)[C@@H]([NH3+])CCC(N)=O] | (S)-5-amino-1-(((R)-1-ethoxy-3-(1-methyl-1H-indol-3-yl)-1-oxopropan-2-yl)amino)-1,5-dioxopentan-2-aminium dihydrogen phosphate | 59 |

$^1$H NMR (400 MHz, DMSO-$d_6$): 1.10 (t, 3H, J = 7.0 Hz), 1.64-1.70 (m, 1H), 1.75-1.85 (m, 1H), 2.06 (t, 2H, J = 7.9 Hz), 3.06-3.18 (m, 2H), 3.44 (br s 1H), 3.72 (s, 3H), 4.04 (q, 2H, J = 7.1 Hz), 4.52 (q, 1H, J = 7.1 Hz), 6.80 (s, 1H), 7.02 (t, 1H, J = 7.5 Hz), 7.11-7.16 (m, 2H), 7.32-7.38 (m, 2H), 7.50 (d, 1H, J = 7.9 Hz), 7.82 (br s, 3H), 8.57 (s, 1H).

| # | Compound | Name | Yield (%) |
|---|---|---|---|
| NLG-1664 | 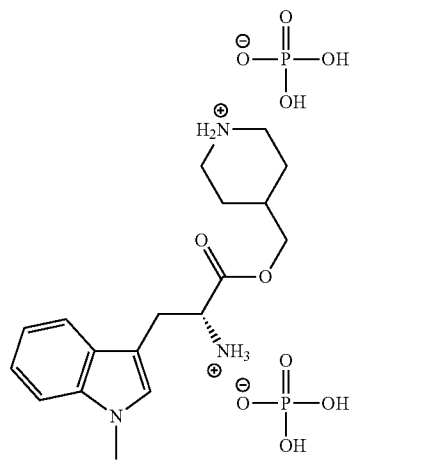 [SMILES: O=P([O-])(O)O ; Cn1cc(C[C@@H]([NH3+])C(=O)OCC2CC[NH2+]CC2)c2ccccc21 ; O=P([O-])(O)O] | (R)-4-(((2-ammonio-3-(1-methyl-1H-indol-3-yl)propanoyl)oxy)methyl)piperidin-1-ium dihydrogen phosphate | 31 |

(DMSO-$d_6$) 1.35-1.56 (m, 4H), 1.63-1.68 (m, 1H), 2.61-2.73 (m, 2H), 3.09-3.26 (m, 4H), 3.73 (s, 3H), 3.81 (dd, 1H, J = 5.1, 10.9 Hz), 3.88 (dd, 1H, J = 5.1, 11.1 Hz), 3.95 (t, 1H, J = 6.7 Hz), 7.02 (t, 1H, J = 7.4 Hz), 7.09-7.17 (m, 1H), 7.21 (s, 1H), 7.38 (d, 1H, J = 8.2 Hz), 7.49 (d, 1H, J = 7.9 Hz), 8.44 (br s, 10H)

| # | Compound | Name | Yield (%) |
|---|---|---|---|
| NLG-1665 | 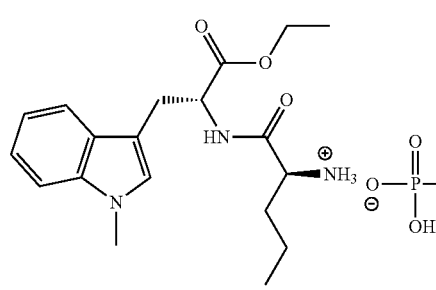 | (S)-1-(((R)-1-ethoxy-3-(1-methyl-1H-indol-3-yl)-1-oxopropan-2-yl)amino)-4-methyl-1-oxopentan-2-aminium dihydrogen phosphate | 59 |

$^1$H NMR (400 MHz, DMSO-$d_6$): 0.77 (dd, 6H, J = 6.5, 6H, 2.2 Hz), 1.1 (t, 3H, J = 7.1, 7.1 Hz), 1.18-1.32 (m, 1H), 1.39-1.50 (m, 1H), 1.39-1.49 (m, 1H), 3.06 (dd, 1H, J = 14.5, 8.4 Hz), 3.17 (dd, 1H, J = 14.4, 5.4 Hz), 3.40 (dd, 1H, J = 8.6, 5.7 Hz), 3.72 (s, 3H), 4.06 (q, 2H, J = 7.1, 7.1, 7.1 Hz), 4.55 (td, 1H, J = 8.1, 8.1, 5.5 Hz), 5.52 (bs, 8H), 7.02 (t, 1H, J = 7.2 Hz), 7.10-7.15 (m, 2H), 7.38 (d, 1H, J = 8.3 Hz), 7.51 (d, 1H, J = 7.9 Hz), 8.62 (d, 1H, J = 7.9 Hz).

| # | Compound | Name | Yield (%) |
|---|---|---|---|
| NLG-1670 | | (S)-6-(((R)-1-carboxy-2-(1-methyl-1H-indol-3-yl)ethyl)amino)-6-oxohexane-1,5-diaminium dihydrogen phosphate | 81 |

$^1$H NMR(Deuterium Oxide, 400 MHz): δ = 0.39-0.78 (m, 2H), 1.21 (ddd, 2H, J = 9.1, 6.8, 2.6 Hz), 1.28-1.49 (m, 2H), 2.39 (td, 2H, J = 7.4, 3.8 Hz), 3.08 (dd, 1H, J = 15.0, 10.9 Hz), 3.45 (ddd, 1H, J = 15.1, 4.5, 1.0 Hz), 3.74 (s, 3H), 3.79 (t, 1H, J = 6.7 Hz), 4.68-4.77 (m, 1H), 7.14 (d, 1H, J = 0.8 Hz), 7.14-7.20 (m, 1H), 7.28 (ddd, 1H, J = 8.3, 7.1, 1.1 Hz), 7.41-7.47 (m, 1H), 7.70 (dd, 1H, J = 7.9, 0.9 Hz) ppm

| # | Compound | Name | Yield (%) |
|---|---|---|---|
| NLG-1677 | | (R)-2-((1-carboxy-2-(1-methyl-1H-indol-3-yl)ethyl)amino)-2-oxoethan-1-aminium dihydrogen phosphate | 80 |

(DMSO-d6) 3.01-3.05 (m, 1H), 3.18-3.22 (m, 1H), 3.42-3.56 (m, 2H), 3.72 (s, 3H), 4.42-4.50 (m, 1H), 7.01-7.14 (m, 3H), 7.33-7.37 (m, 1H), 7.51-7.55 (m, 1H), 8.44 (br s, 9H), 8.65 (s, 1H)

| # | Compound | Name | Yield (%) |
|---|---|---|---|
| NLG-03272-02 | | (S)-1-(((R)-1-ethoxy-3-(1-methyl-1H-indol-3-yl)-1-oxopropan-2-yl)amino)-4-(methylthio)-1-oxobutan-2-aminium dihydrogen phosphate | 75 |

$^1$H NMR(DMSO-d$_6$, 400 MHz): δ (ppm) 1.13 (t, J = 7.1 Hz, 3H), 1.64-1.72 (m, 1H), 1.73-1.84 (m, 1H), 1.93 (s, 3H), 2.28 (t, J = 7.9 Hz, 2H), 3.08 (dd, J = 14.6, 8.5 Hz, 1H), 3.18 (dd, J = 14.5, 5.2 Hz, 1H), 3.54 (t, J = 6.0 Hz, 1H), 3.73 (s, 3H), 4.07 (q, J = 7.1 Hz, 2H), 4.56 (q, J = 6.8, 6.1 Hz, 1H), 7.02 (t, J = 7.4 Hz, 1H), 7.07-7.23 (m, 2H), 7.38 (d, J = 8.2 Hz, 1H), 7.51 (d, J = 7.9 Hz, 1H), 7.98 (br s, 5H), 8.68 (d, J = 7.7 Hz, 1H)

| # | Compound | Name | Yield (%) |
|---|---|---|---|
| NLG-03380-02 | | (S)-1-(((R)-1-carboxy-2-(1-methyl-1H-indol-3-yl)ethyl)amino)-4-(methylthio)-1-oxobutan-2-aminium dihydrogen phosphate | 78 |

| # | Compound | Name | Yield (%) |
|---|----------|------|-----------|

¹H NMR(DMSO-d₆, 400 MHz): δ (ppm) 1.63-1.79 (m, 2H), 1.85 (s, 3H), 2.13 (t, J = 8.1 Hz, 2H), 3.01 (dd, J = 14.6, 9.0 Hz, 1H), 3.23 (dd, J = 14.7, 4.6 Hz, 1H), 3.72 (s, 4H), 4.51 (s, 1H), 7.00 (t, J = 7.5 Hz, 1H), 7.06-7.20 (m, 2H), 7.36 (d, J = 8.2 Hz, 1H), 7.54 (d, J = 7.9 Hz, 1H), 8.63 (s, 6H).

General Method for the Generation of Mono and Di Methanesulfonate and Benzenesulfonate Salts of Indoximod Prodrugs.

To a solution of free base (0.25 g, 0.723 mmol) in ethanol (10 mL) at rt, was added methanesulfonic or benzenesulfonic acid (0.723 mmol or 1.446 mmol in case of diamines) and the mixture was stirred at rt overnight. Ethanol was evaporated and the crude product was stirred in methyl tert-butyl ether for 1-5 h. The precipitate was filtered and dried to yield the corresponding methanesulfonate or benzenesulfonate salt.

| # | Compound | Name | Yield (%) |
|---|----------|------|-----------|
| NLG-1627 | (structure) | (2R)-1-(2,3-dihydroxypropoxy)-3-(1-methyl-1H-indol-3-yl)-1-oxopropan-2-aminium methanesulfonate | 41 |

¹H NMR (400 MHz, DMSO-d₆): 2.31 (s, 3H), 3.24-3.29 (m, 2H), 3.29-3.41 (m, 2H), 3.65-3.68 (m, 1H), 3.75 (s, 3H), 4.04 (dd, 1H, J = 11.1, 6.3 Hz), 4.16 (dd, 1H, J = 11.0, 4.0 Hz), 4.28 (br s, 1H), 7.06 (ddd, 1H, J = 8.0, 7.1, 1.0 Hz), 7.17 (ddd, 1H, J = 8.2, 7.1, 1.1 Hz), 7.21 (s, 1H), 7.39-7.46 (m, 1H), 7.54 (dt, 1H, J = 8.1, 0.9 Hz), 8.29 (br s, 3H).

| # | Compound | Name | Yield (%) |
|---|----------|------|-----------|
| NLG-1631 | (structure) | ((S)-5-amino-1-(((R)-1-ethoxy-3-(1-methyl-1H-indol-3-yl)-1-oxopropan-2-yl)amino)-1,5-dioxopentan-2-aminium methanesulfonate | 78 |

¹H NMR (400 MHz, DMSO-d₆): 1.11 (t, 3H, J = 7.1 Hz), 1.80-1.86 (m, 2H), 1.97-2.13 (m, 2H), 2.31 (s, 3H), 3.08 (dd, 1H, J = 14.5, 8.2 Hz), 3.18 (dd, 1H, J = 14.5, 6.0 Hz), 3.72 (s, 3H), 3.85 (q, 1H, J = 5.6 Hz), 4.06 (q, 2H, J = 7.1 Hz), 4.59 (td, 1H, J = 8.0, 6.0 Hz), 6.98 (s, 1H), 7.03 (ddd, 1H, J = 8.0, 6.9, 1.0 Hz), 7.09-7.18 (m, 2H), 7.34-7.42 (m, 2H), 7.52 (dt, 1H, J = 7.9, 1.0 Hz), 8.12 (d, 3H, J = 5.6 Hz), 8.93 (d, 1H, J = 7.9 Hz).

| # | Compound | Name | Yield (%) |
|---|---|---|---|
| NLG-1662 | | (R)-4-(((2-ammonio-3-(1-methyl-1H-indol-3-yl)propanoyl)oxy)methyl)piperidin-1-ium methanesulfonate | 32 |

(DMSO-d$_6$) 1.25 (dt, 2H, J = 8.3, 34.3 Hz), 1.49 (ddd, 3H, J = 8.0, 12.1, 23.2 Hz), 2.50 (s, 6H), 2.54-2.69 (m, 2H), 3.01-3.15 (m, 2H), 3.58 (s, 3H), 3.70 (dd, 1H, J = 4.2, 11.0 Hz), 3.79 (dd, 1H, J = 4.1, 11.0 Hz), 3.96-4.07 (m, 1H), 6.88 (t, 1H, J = 7.5 Hz), 6.95-7.03 (m, 2H), 7.12 (d, 1H, J = 8.1 Hz), 7.31 (d, 1H, J = 7.9 Hz), 8.13-8.33 (m, 3H), 8.59 (t, 1H, J = 10.5 Hz)

| # | Compound | Name | Yield (%) |
|---|---|---|---|
| NLG-1666 | | (S)-1-(((R)-1-ethoxy-3-(1-methyl-1H-indol-3-yl)-1-oxopropan-2-yl)amino)-4-methyl-1-oxopentan-2-aminium methanesulfonate | 69 |

$^1$H NMR (400 MHz, DMSO-d$_6$): 0.73 (dd, 6H, J = 8.2, 6.3 Hz, 6H), 1.16 (t, 3H, J = 7.1, 7.1 Hz, 3H), 1.24 (t, 2H, J = 7.1, 7.1 Hz, 2H), 1.32 (dt, 1H, J = 13.0, 6.7, 6.7 Hz, 1H), 2.29 (s, 3H), 3.03 (dd, 1H, J = 14.5, 9.3 Hz, 1H), 3.20 (dd, 1H, J = 14.5, 5.3 Hz), 3.72 (s, 3H), 4.11 (q, 2H, J = 7.1, 7.1, 7.1 Hz), 4.64 (td, 1H, J = 8.8, 8.8, 5.5 Hz), 7.02 (t, 1H, J = 7.5, 7.5 Hz), 7.13 (d, 2H, J = 9.8 Hz), 7.38 (d, 1H, J = 8.2 Hz), 7.52 (d, 1H, J = 7.9 Hz), 8.01 (s, 3H), 8.92 (d, 1H, J = 8.2 Hz, 1H).

| # | Compound | Name | Yield (%) |
|---|---|---|---|
| NLG-1668 | | (S)-6-(((R)-1-carboxy-2-(1-methyl-1H-indol-3-yl)ethyl)amino)-6-oxohexane-1,5-diaminium methanesulfonate | 79 |

$^1$H NMR(Methanol-d$_4$, 400 MHz): δ = 0.82-0.98 (m, 2H), 1.26-1.40 (m, 2H), 1.42-1.56 (m, 2H), 1.73 (dt, 1H, J = 15.3, 7.5 Hz), 1.96 (dddd, 1H, J = 26.4, 16.4, 12.9, 6.1 Hz), 2.53 (ddd, 2H, J = 13.0, 6.6, 4.6 Hz), 2.71 (s, 6H), 3.14 (dd, 1H, J = 14.9, 10.0 Hz), 3.44 (ddd, 1H, J = 14.9, 4.6, 1.0 Hz), 3.78 (s, 3H), 3.81 (t, 1H, J = 6.5 Hz), 7.03-7.11 (m, 2H), 7.19 (ddd, 1H, J = 8.3, 7.1, 1.2 Hz), 7.36 (dt, 1H, J = 8.3, 0.9 Hz), 7.60 (dt, 1H, J = 8.0, 1.0 Hz) ppm

| # | Compound | Name | Yield (%) |
|---|---|---|---|
| NLG-1671 | | ethyl N$^\alpha$-((S)-2-($\lambda^4$-azanyl)-4-methylpentanoyl)-1-methyl-D-tryptophanate besylate | 68 |

$^1$H NMR (400 MHz, DMSO-d$_6$): 0.73 (dd, 6H, J = 8.2, 6.3 Hz), 1.16 (t, 3H, J = 7.1, 7.1 Hz), 1.24 (t, 2H, J = 7.3, 7.3 Hz), 1.32 (dt, 1H, J = 13.0, 6.5, 6.5 Hz), 2.98-3.09 (m, 1H), 3.20 (dd, 1H, J = 14.5, 5.2 Hz), 3.72 (s, 3H), 4.11 (q, 2H, J = 7.1, 7.1, 7.1 Hz), 4.64 (td, 1H, J = 8.9, 8.9, 5.4 Hz), 6.99-7.05 (m, 1H), 7.09-7.17 (m, 2H), 7.26-7.35 (m, 3H), 7.38 (d, 1H, J = 8.2 Hz), 7.52 (d, 1H, J = 8.0 Hz), 7.59 (dd, 2H, J = 7.7, 1.9 Hz), 8.00 (s, 3H), 8.92 (d, 1H, J = 8.2 Hz).

General Method for the Generation of Mono, Disulfate and Hydrogen Sulfate Salts of Indoximod and Indoximod Prodrugs.

To a solution of free base (1.22 mmol) in dry THF (10 mL) at 0° C. was added sulfuric acid (0.611 mmol or 1.22 mmol) as a solution in THF (2 mL) and the solution was allowed to warm to rt. After stirring for 2-6 h, the solvent was distilled-off and the crude was stirred with methyl tert-butyl ether, the solid was filtered and dried under vacuum to yield the desired product.

| # | Compound | Name | Yield (%) |
|---|---|---|---|
| NLG-1628 | | (2R)-1-(2,3-dihydroxypropoxy)-3-(1-methyl-1H-indol-3-yl)-1-oxopropan-2-aminium sulfate | 43 |

$^1$H NMR (400 MHz, DMSO-d$_6$): 3.05-3.19 (m, 2H), 3.29-3.40 and 3.44-3.55 (two m, 2H), 3.62-3.69 (m, 1H), 3.74 (s, 3H), 3.89-3.99 (m, 2H), 4.07-4.12 (m, 1H), 6.25 (br s, 2H), 7.03 (t, 1H, J = 7.7 Hz), 7.11-7.21 (m, 2H), 7.40 (d, 1H, J = 8.1 Hz), 7.51-7.57 (m, 1H).

| | | | |
|---|---|---|---|
| NLG-1630 | | (S)-5-amino-1-(((R)-1-ethoxy-3-(1-methyl-1H-indol-3-yl)-1-oxopropan-2-yl)amino)-1,5-dioxopentan-2-aminium sulfate | 83 |

| # | Compound | Name | Yield (%) |
|---|----------|------|-----------|

¹H NMR (400 MHz, DMSO-d₆): 1.10 (t, 3H, J = 7.1 Hz), 1.63-1.74 (m, 1H), 1.75-1.86 (m, 1H), 2.02-2.07 (m, 2H), 3.13 (qd, 2H, J = 14.5, 6.8 Hz), 3.52 (dd, 1H, J = 7.4, 5.0 Hz), 3.72 (s, 3H), 4.04 (q, 2H, J = 7.1 Hz), 4.55 (q, 1H, J = 1.6 Hz), 6.47 (br s, 2H), 6.85 (s, 1H), 7.03 (t, 1H, J = 7.5 Hz), 7.10-7.19 (m, 2H), 7.29 (s, 1H), 7.38 (d, 1H, J = 8.2 Hz), 7.51 (d, 1H, J = 7.9 Hz), 8.59 (d, 1H, J = 7.9 Hz).

NLG-1663 — (R)-4-(((2-ammonio-3-(1-methyl-1H-indol-3-yl)propanoyl)oxy)methyl)piperidin-1-ium hydrogen sulfate — 25

(DMSO-d₆) 1.08-1.30 (m, 2H), 1.42-1.59 (m, 2H), 1.64-.178 (m, 1H), 2.64-2.84 (m, 2H), 3.11-3.35 (m, 4H), 3.75 (s, 3H), 3.81-3.90 (m, 2H), 4.22-4.27 (m, 1H), 5.79 (br s, 7H), 7.06 (t, 1H, J = 7.4 Hz), 7.11-7.24 (m, 2H), 7.43 (d, 1H, J = 8.1 Hz), 7.51 (d, 1H, J = 7.7 Hz), 8.17 (s, 1H), 8.39 (s, 2H), 8.51 (s, 1H)

NLG-1667 — (R)-1-carboxy-2-(1-methyl-1H-indol-3-yl)ethan-1-aminium hydrogen sulfate — 30

(DMSO-d₆) 3.17 (dd, 1H, J = 15.1, 7.2 Hz), 3.27 (dd, 1H, J = 15.0, 5.3 Hz), 3.74 (s, 3H), 3.96 (t, 1H, J = 6.2 Hz), 7.04 (t, 1H, J = 7.4 Hz), 7.12-7.21 (m, 2H), 7.41 (d, 1H, J = 8.2 Hz), 7.58 (d, 1H, J = 8.0 Hz), 8.52 (br s, 4H)

NLG-1669 — (S)-6-(((R)-1-carboxy-2-(1-methyl-1H-indol-3-yl)ethyl)amino)-6-oxohexane-1,5-diaminium sulfate — 82

¹H NMR(DMSO-d₆, 400 MHz): δ = 1.08-1.58 (m, 7H), 2.55-2.71 (m, 2H), 3.03 (dd, 1H, J = 14.6, 8.8 Hz), 3.21 (dd, 1H, J = 14.6, 4.9 Hz), 3.63 (s, 1H), 3.72 (s, 3H), 4.53 (d, 1H, J = 7.9 Hz), 7.02 (t, 1H, J = 7.4 Hz), 7.09-7.18 (m, 2H), 7.37 (d, 1H, J = 8.2 Hz), 7.56 (d, 1H, J = 7.9 Hz), 8.25 (br s, 6H) ppm

| # | Compound | Name | Yield (%) |
|---|---|---|---|
| NLG-1691 | 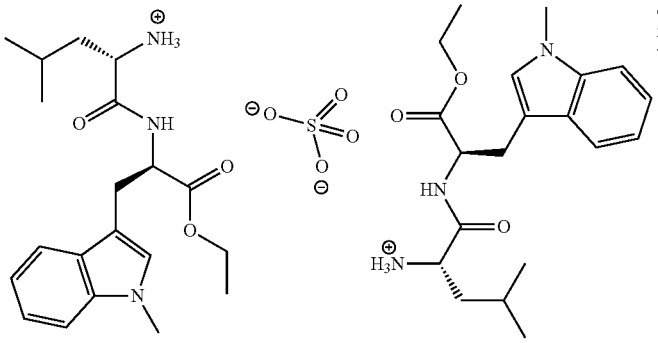 [SMILES: CCOC(=O)[C@@H](Cc1cn(C)c2ccccc12)NC(=O)[C@@H]([NH3+])CC(C)C ; O=S(=O)([O-])[O-] ; CCOC(=O)[C@@H](Cc1cn(C)c2ccccc12)NC(=O)[C@@H]([NH3+])CC(C)C] | ethyl $N^{\alpha}$-((S)-2-($\lambda^4$-azanyl)-4-methylpentanoyl)-1-methyl-D-tryptophanate sulfate | 29 |

$^1$H NMR (400 MHz, DMSO-d$_6$): 0.72-0.78 (m, 6H), 1.11 (t, 3H, J = 7.2, 7.2 Hz), 1.14-1.18 (m, 1H), 1.22-1.30 (m, 1H), 1.45 (dt, 1H, J = 13.5, 6.8, 6.8 Hz), 3.00-3.08 (m, 1H), 3.15 (dd, 1H, J = 14.5, 5.6 Hz), 3.70 (s, 3H), 4.05 (q, 2H, J = 7.1, 7.1, 7.1 Hz), 4.54 (q, 1H, J = 7.5, 7.5, 7.4 Hz), 7.00 (t, 1H, J = 7.5, 7.5 Hz), 7.11 (m, 2H), 7.36 (d, 1H, J = 8.2 Hz), 7.49 (d, 1H, J = 7.9 Hz), 8.48 (d, 1H, J = 7.9 Hz).

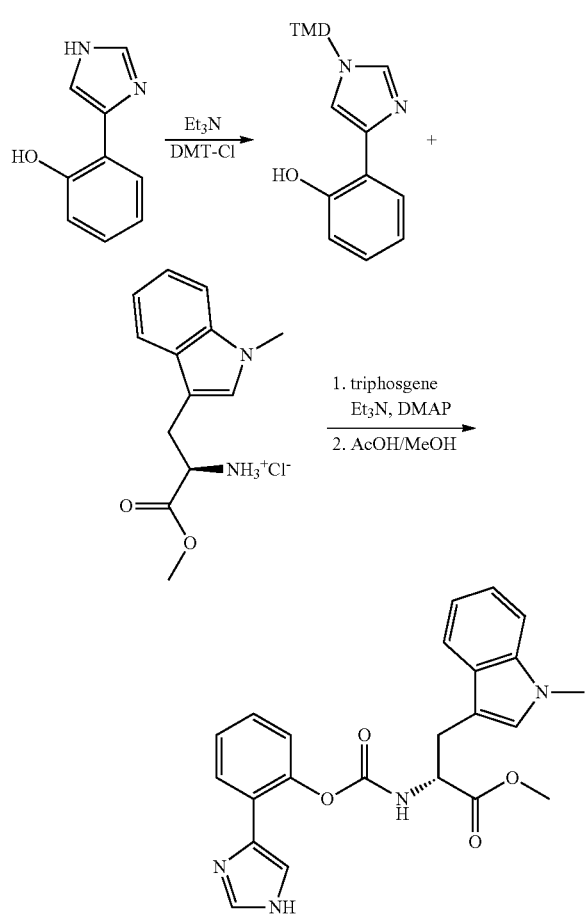

Synthesis of (R)-methyl 2-(((2-(1H-imidazol-4-yl)phenoxy)carbonyl)amino)-3-(1-methyl-1H-indol-3-yl)propanoate (NLG-1264)

To a solution of 2-(1H-imidazol-4-yl)phenol (1.0 mmol) (prepared according to J. Med. Chem., 2008, 51(16), pp 4968-4977) in DMF (3 mL) was added triethylamine (1.1 mmol). After stirred for 10 min, a solution of 4,4'-Dimethoxytrityl chloride (1.0 mmol) in DMF (2 mL) was added dropwise. After stirred overnight under a nitrogen atmosphere, the reaction mixture was poured into ice water (10 mL). The solid was filtered off, washed with cold water and dissolved in ethyl acetate. The organic layer was dried over Na2SO4 and concentrated the crude product was taken into next step without further purification. To a suspension of (R)-methyl 2-amino-3-(1-methyl-1H-indol-3-yl)propanoate (0.5 mmol) (prepared as described by Paul Cox, Donald Craig, Stephanos Ioannidis, Volker S. Rahn, Tetrahedron Letters 2005, 46, 4687) in DCM (3 mL) was added triphosgene (0.5 mmol) and Et3N (2.0 mmol) at 0° C. The solution was allowed to stir for 1 h and was concentrated to dryness. The crude residue was used immediately in the next step without purification. The crude residue was dissolved in DCM (5 mL), the phenyl imidazole derivative (0.5 mmol) and DMAP (1.5 mmol) were added. The resulting solution was allowed to stir at rt overnight. The solvent was removed under reduced pressure and the crude residue was filtered through a plug of silica gel and concentrated. To the residue was added MeOH (3 mL) and AcOH (2 mL) and the solution was stirred at rt for 30 min. The solution was diluted with water and made basic with solid K2CO3 (pH~8-9). The aqueous was extracted with EtOAc and the combined organic layers were washed with water, brine and dried (Na2SO4). The crude residue was purified by column chromatography on silica gel afforded the compound (21% yield). 1H NMR: 3.20-3.48 (m, 2H), 3.66 (s, 3H), 3.70 (s, 3H), 4.61-4.75 (m, 1H), 6.57 (d, 1H, J=7.2 Hz), 6.90-7.30 (m, 7H), 7.50-7.58 (m, 1H), 7.10-7.76 (m, 2H).

Example 2: Characterization of Solid Form of Indoximod Free Base

D-1MT (HPLC purity 99.6%) free base is a white powder and it displays birefringence, needle shape and crystalline appearance under the polarized light microscope (PLM) and by X-ray powder dispersion spectroscopy (XRPD) (FIG. 1). It only shows single melt endothermic peak with onset at 293.8° C. by thermogravimetric analysis (TGA) and differential scanning calorimetry (DSC) and ~0.01% weight loss from 30-200° C., indicating that is an anhydrate form. This crystalline form is non-hygroscopic (0.09% weight gain from 0-80% RH), and does not show changes after dynamic vapor sorption method (DVS). Furthermore, stability studies of the solid powder form indicate that D-1MT is chemically stable at the tested conditions (25° C./60% RH, 40° C., 40° C./75% RH, 60° C. and 70° C.) for 4 weeks. Additionally, it is also stable in solution in 0.1 N HCl, and 50 mM phosphate buffers pH 2-8 at 25° C. for 24 hours, while it shows minor degradation (0.45%-3.3%) in pH 2 and pH 8 buffers with 0.3% $H_2O_2$ (the most impurity was RRT=0.58).

Example 3: Characterization of Indoximod Free Base Solubility

The solubility of indoximod as free base in buffered or un-buffered solutions, as well as in simulated biological fluids (SGF, FaSSIF or FeSSIF) is shown in FIG. 5 (open symbols). Solubility of indoximod in aqueous solutions of pH 2-8 is 1.8-2.0 mg/mL, with higher solubility at pH<1.5 or >10. This low solubility at neutral pH range is likely due to the high molecular packing energy of indoximod in the crystal, which is reflected by the very high melting point of 293.8° C. This low solubility of indoximod in the pH range corresponding to intestinal pH may in part explain the limiting dose absorption at doses higher than 800 mg in humans. Therefore, we studied whether salts or sprayed dry dispersions of indoximod could increase solubility and exposure after oral dosing.

Example 4: Characterization of Indoximod Salts and their Solubility

Several salts of indoximod were manufactured and their physicochemical properties were evaluated (Table 2). The hydrochloride, sulfate, phosphate, hemi-phosphate, mesylate and hemi-mesylate salts were solid white powders that showed crystalline properties by PLM and XRPD and were anhydrous by TGA. These salts showed lower melting point than the free base, suggesting increased solubility in water in the range of pH between >1.5 and <10. Most of these salts showed increases of solubility to ~4.7-8.6 mg/mL in water and 5.5-10.6 mg/mL in SGF, with the hydrochloride salt showing a very significant increase to >200 mg/mL in water or SGF.

Another indoximod salt tested was the maleic acid salt, which showed low melting point of 194° C. and poor crystallinity by PLM and XRPD. This salt has the appearance of a sticky white powder of hydrate or solvate form (4.5% weight loss by TGA).

The tosylate salt shows the appearance of a brown oil, which may be advantageous as that could increase the intestinal absorption of the active ingredient.

Other salts had less favorable physico-chemical properties. For example, lactate and N-methyl glucamine did not form a salt with indoximod, and the crystal showed a mixture of indoximod free base crystals and N-methyl glucamine or lactate crystals.

The sodium salt did not show crystalline morphology, it was a hydrate or solvate with very low melting and multiple decomposition peaks by TGA or DSC and thus it was not further characterized.

TABLE 2

Physico-chemical properties of indoximod and its salts

| Salt | Appearance | DSC (Melting or decomposition point) | TGA (Weight loss) | Stoichiom. (API:acid) | Purity | PLM | Cristalinity XRPD | Hygro-scopicity (0-80% RH) | Solubility (25° C., mg/mL) Water (pH) | SGF (pH) |
|---|---|---|---|---|---|---|---|---|---|---|
| Free base | Anhydrate white powder | 293.80° C. | ~0.01% (30-200° C.) | — | 99.6 | Yes | Yes (Free Base) | 0.09 | 1.8 (6.03) | 3.6 (2.32) |
| HCl Salt | Anhydrate white powder | 230.59° C. | ~0.13% (30-120° C.) | 1:1.05 | 99.7 | Yes | HCl Salt Form 1 | 0.017 | >200 (1.06) | >200 (1.03) |
| Sulfate | Anhydrate white powder | 225.86° C. | ~1.89% (26-120° C.) | 1:0.51 | 99.6 | Yes | Sulfate Form 1 | 3.4 | 4.7 (2.03) | 5.5 (1.68) |
| Hemi-Phosphate | Anhydrate white powder | 216.1° C. | ~0.6% (30-150° C.) | 1:0.60 | 99.0 | Yes | Phosphate Form 1 | — | 8.6 (2.42) | 10.6 (2.05) |
| Phosphate | Anhydrate white powder | 225.09° C. | ~0.15% (30-150° C.) | 1:1.01 | 98.9 | Yes | Phosphate Form 1 | 1.7 | 8.32 (NA) | 9.83 (NA) |
| Hemi-Mesylate | Anhydrate white powder | 266.2° C. | ~0.3% (30-150° C.) | 1:0.56 | 99.7 | Yes | Poor crystaline | — | 5.5 (2.34) | 6.0 (1.84) |
| Mesylate | Anhydrate white powder | 209.71° C. | ~0.18% (30-150° C.) | 1:0.98 | 99.5 | Yes | Mesylate + Free Base | 0.12* | 5.1 (1.84) | 6.0 (1.43) |
| Maleate | Hydrate or solvate | 102.6° C. 194.3° C. | ~4.5% (25-150° C.) | 1:0.50 | 99.3 | Yes | Maleate Form 1 | — | — | — |
| Tosylate | Brown oil | — | — | — | 97.3 | No | NA | — | — | — |
| Lactate | White suspension | | | 1:01 | | | Lactic Acid + Free Base | | | |
| N-methyl glucamine | White suspension | | | 1:01 | | | Glucamine + Free Base | | | |
| Sodium Salt | Hydrate or solvate | 63.82° C. | ~16.9% (30-100° C.) | 1:1.03 | 98.8 | No | Na salt Form 1 | — | — | — |

Example 4: Sprayed Dry Dispersions of Indoximod

A list of indoximod sprayed dry dispersion (SDD) formulations were made in order to assess whether any SDD formulation was able to increase the molecular absorption by generating and maintaining a supersaturated state of indoximod in gastrointestinal fluid so that its absorption could be enhanced. In this study, SDD formulations were made by two methods: hot process spray dry—formulation solution heated up to 110° C. before spraying dry, and basic spray dry—formulation pH raised up to ~11.5 (room temperature) before spraying dry. The performance of each SDD formulation was investigated by in-vitro dissolution test in simulated gastric buffer (GB) and simulated intestinal fluid (SIF). As shown in Table 3, $C_{maxGB}$ represented the maximum concentration of indoximod in solution when enough of the SDD formulation was dissolved in GB for 30 min; $C_{max90}$ represents the maximum indoximod concentration when the SDD was dissolved in SIF for 90 min; UltraC$_{90}$ represents the concentration in SIF after 90 min of dissolution followed by ultracentrifugation to remove any particulates and UltraC$_{1200}$ represents the concentration in SIF after 1200 min of dissolution followed by ultracentrifugation to remove any particulates. It was expected that the enhanced concentrations of indoximod in GB and SIF increased the absorption of indoximod when the SDD formulation was dosed in animals as well as human beings. Another criterion to evaluate these SDD formulations was physical and chemical stability of indoximod in these formulations. It was found that SDD formulations made by hot process spray drug method were in general more stable than those made by basic process spray dry. In addition, higher drug load in the powder was preferred since it could decrease the dose amount of the final formulation. Based on all these criteria, two SDD formulations were selected for further in vivo PK studies in monkeys. The first one was 50% indoximod/50% PVPVA-64, which showed a 1.8-fold increased predicted intestinal concentration than indoximod (UltraC$_{90}$ 3293 ng/mL vs 1849 ng/mL); and the second was 50% indoximod/50% Affinisol 126, which showed a 2.3-fold higher predicted intestinal concentration than indoximod (UltraC$_{90}$ 4340 ng/mL vs 1849 ng/mL). These SDDs were prepared by the hot process dry spray which showed better stability properties.

TABLE 3

Dissolution tests for sprayed dry dispersion formulations of indoximod

| Composition | Process Method | $C_{maxGB}$ (µg/mL) | $C_{max90}$ (µg/mL) | UltraC$_{90}$ (µg/mL) | UltraC$_{1200}$ (µg/mL) |
|---|---|---|---|---|---|
| Indoximod API (control) | NA | 5,154 | 2,213 | 1,849 | 1,854 |
| 10% Indoximod/90% Affinisol 126 | hot process spray dry | 6,253 | 3,027 | 2,982 | 3,392 |
| 25% Indoximod/75% Affinisol 126 | basic spray dry | 7,466 | 4,064 | 3,023 | 3,096 |
| 25% Indoximod/75% HPMC-E3 | basic spray dry | 17,281 | 7,313 | 3,943 | 3,171 |
| 25% Indoximod/75% PVPVA-64 | basic spray dry | 20,116 | 9,349 | 2,531 | 2,908 |
| 25% Indoximod/75% Affinisol 126 | hot process spray dry | 6,831 | 3,932 | 3,892 | 3,976 |
| 25% Indoximod/75% | hot process | 4,015 | 2,487 | 2,494 | 2,598 |
| Eudragit L100 | spray dry | | | | |
| 25% Indoximod/75% PVPVA-64 | hot process spray dry | 8,488 | 3,623 | 3,372 | 2,840 |
| 50% Indoximod/50% PVPVA-64 | basic spray dry | 10,442 | 4,745 | 4,828 | 2635 |
| 50% Indoximod/50% HPMC E3 | basic spray dry | 9,967 | 4,630 | 4,802 | 3,067 |
| 50% Indoximod/50% Affinisol 126 | hot process spray dry | 6,078 | 3,455 | 3,690 | 3,471 |
| 50% Indoximod/50% Affinisol 912 | hot process spray dry | 5,931 | 3,352 | 3,599 | 3,228 |
| 50% Indoximod/50% PVPVA-64 | hot process spray dry | 8,481 | 3,695 | 3,293 | 3,018 |
| 50% Indoximod/50% Affinisol 126 | hot process spray dry | 8,995 | 4,187 | 4,340 | 4,194 |

Example 5: Pharmacokinetic Comparison of Indoximod Free Base, Indoximod Salts and Indoximod SDD in Cynomolgus Monkeys In order to determine whether salts or SDDs that show increase in solubility compared to indoximod free base result in an increase in the maximum concentration (Cmax) and total exposure (AUC$_{0 \to \infty}$) of indoximod, we carried out a comparative crossover pharmacokinetic study in cynomolgus monkeys, which is a common species used to predict human oral bioavailability. Two groups of 4 monkeys each (all males) were orally dosed at 275 µmol/kg (Group 1) or 825 µmol/kg (Group 2) with: 1) indoximod free base capsules; 2) indoximod hydrochloride capsules; 3) indoximod hemi phosphate capsules; 4) SDD1 suspension (indoximod 50%/50% PVPVA-64, (w/w)) and 5) SDD2 suspension (indoximod 50%/Affinisol 126 50% (w/w)). Each monkey was dosed with each of the 5 dose formulations once every 7 days, and blood samples were obtained at 0, 0.25 h, 0.5 h, 1 h, 2 h, 4 h, 6 h, 8 h, 12 h, 24 h, 36 h and 48 h. Concentration of indoximod was determined from plasma by a validated LC-MS/MS analytical method. $C_{max}$ and AUC$_{(0-48\ h)}$ was calculated by non-compartmental analysis using WinNonLin software (Certara). For indoximod in capsule formulation, animals in Group 1 were orally dosed with 3 capsules A and animals in Group 2 were dosed with 4 capsules B. Compositions of capsules A and B are shown in Table 4. For indoximod in SDD formulation, animals in Group 1 were dosed with 4 mL/kg of a 15 mg indoximod/mL suspension and animals in Group 2 were dosed with 4 mL/kg of a 45 mg indoximod/mL suspension. The SDD suspension formulations were prepared in 0.5% methylcellulose (Methocel).

TABLE 4

Composition of capsules containing indoximod in its free base or salt forms for oral dosing to cynomolgus monkeys

|  | Indoximod Free Base | | Indoximod HCl | | Indoximod 0.5 PO$_4$H$_3$ | |
|---|---|---|---|---|---|---|
|  | MW (g/mol) | | | | | |
|  | 218.26 | | 254.76 | | 267.3 | |
| Ingredients (mg) | Cap A | Cap B | Cap A | Cap B | Cap A | Cap B |
| Active Ingredient (mg) | 100 | 225 | 116.7 | 262.5 | 122.4 | 275.5 |
| Avicel PH101 (mg) | 17.9 | 40.2 | 20.8 | 46.9 | 21.9 | 49.2 |
| Mannitol (mg) | 17.9 | 40.2 | 20.8 | 46.9 | 21.9 | 49.2 |
| Croscarmellose Sodium (mg) | 7.1 | 16.1 | 8.3 | 18.8 | 8.7 | 19.7 |
| Total | 142.9 | 321.4 | 166.7 | 375 | 174.9 | 393.6 |

The average Cmax and AUC$_{(0-48\ h)}$ parameter values observed in each group obtained after dosing with each formulation of indoximod are shown in Table 5. The percentage of increase in these values as well as the P value obtained for the comparison of each formulation against that of indoximod free base is shown in Table 5. Dosing of indoximod HCl capsules results in a significant increase in Cmax (31-65%) and exposure (37-53%) at both dose levels tested compared to dosing of indoximod free base capsules. Similarly, indoximod hemi phosphate capsules produced a significant increase in Cmax (7-44%) and exposure (27-34%). On the contrary, indoximod in SDD1 or SDD2 formulation produced a significant increase in Cmax (15-94%) but failed to increase the overall exposure with respect to indoximod free base capsules. For these reasons, indoximod salts in their hydrocholoride, hemi-phosphate or phosphate salts are preferred over indoximod in its free base form, either in capsules or in spray dry dispersions.

Example 6: Pharmacokinetic Testing of Indoximod Salts in Capsule Formulation in Rats In order to determine whether salt formation increased the maximum concentration (Cmax) and total exposure (AUC$_{0\rightarrow\infty}$) of indoximod in rats, we tested the hydrochloride, phosphate, sulfate and mesylate salts of indoximod, and formulated these into capsules by mixing them with appropriate excipients. Three dose levels were investigated: 37, 185 or 500 μmol/kg.

Gelatin capsules (Torpac, 20 mg capacity) were prepared containing 11.4, 28.6 or 50 μmol/capsule of indoximod or its salts, with or without excipients consisting of microcrystalline cellulose, lactose monohydrate, croscarmellose sodium and magnesium stearate, in proportions shown in Table 6.1-6.3. Capsules were manually filled and the composition uniformity of a representative sample of capsules from each batch was verified by weight and by LC-MS/MS to determine the average indoximod content.

TABLE 5

Comparison of Cmax and total exposure (AUCO -> ∞) between indoximod free base vs its salts or sprayed dry dispersions in monkeys

|  | indoximod Free Base | indoximod HCl | indoximod 0.5.H$_3$PO$_4$ | indoximod PVPVA-64 | indoximod Affinisol 126 |
|---|---|---|---|---|---|
| Dose | 275 μmol/kg | | | | |
| Number of Animals | 4 | 4 | 4 | 4 | 4 |
| Cmax, average (μM) | 12.9 ± 3.3 | 21.3 ± 8.9 | 18.5 ± 4.8 | 25 ± 5 | 21.3 ± 5 |
| % Increase over indoximod FB | NA | 65 | 44 | 94 | 65 |
| P value | NA | 0.047 | 0.033 | 0.010 | 0.017 |
| AUC(0 -> 48 h) (μM · h) | 66 ± 17 | 101 ± 18 | 89 ± 15 | 72.5 ± 18 | 83 ± 25 |
| % Increase over indoximod FB | NA | 53 | 34 | 9 | 26 |
| P value | NA | 0.043 | 0.065 | 0.36 | 0.2 |
| Dose | 825 μmol/kg | | | | |
| Number of Animals | 4 | 4 | 4 | 4 | 4 |
| Cmax, average (μM) | 25.6 ± 12.8 | 33.4 ± 12 | 23.4 ± 12.7 | 29.4 ± 10 | 33.7 ± 8.4 |
| % Increase over indoximod FB | NA | 31 | 7 | 15 | 32 |
| P value | NA | 0.010 | 0.042 | 0.041 | 0.025 |
| AUC(0 -> 48 h) (μM · h) | 127 ± 73 | 173 ± 75 | 161 ± 81 | 141 ± 61 | 136 ± 57 |
| % Increase over indoximod FB | NA | 37 | 27 | 11 | 7 |
| P value | NA | 0.012 | 0.015 | 0.18 | 0.29 |

This study shows that the hydrochloride and phosphate salts of indoximod can produce an increase in Cmax and AUC pharmacokinetic parameters with respect to the free base, in the range of doses between 275-825 μmol/kg.

TABLE 6.1

Composition of capsules A containing indoximod in its free base or salt forms for oral dosing of rats at 37 µmol/kg

|  | indoximod Free Base | | indoximod HCl | | indoximod $H_3PO_4$ | | indoximod $H_2SO_4$ | | indoximod $CH_3SO_3H$ | |
|---|---|---|---|---|---|---|---|---|---|---|
| MW (g/mol) | 218.26 | | 254.76 | | 316.25 | | 316.33 | | 314.36 | |
|  | (mg) | % (w/w) | (mg) | % (w/w) | (mg) | % (w/w) | (mg) | % (w/w) | (mg) | % (w/w) |
| Active Ingredient | 2.50 | 12.50 | 2.92 | 14.59 | 3.62 | 18.11 | 3.62 | 18.11 | 3.60 | 18.00 |
| Microcrystalline Cellulose | 7.45 | 37.25 | 7.3 | 36.50 | 7.1 | 35.50 | 7.1 | 35.49 | 7.1 | 35.50 |
| Lactose Monohydrate | 7.45 | 37.25 | 7.3 | 36.50 | 7.1 | 35.50 | 7.1 | 35.49 | 7.1 | 35.50 |
| Croscarmellose Sodium | 2.4 | 12.00 | 2.28 | 11.40 | 1.98 | 9.90 | 1.98 | 9.90 | 2 | 10.00 |
| Magnesium Stearate | 0.2 | 1.00 | 0.2 | 1.00 | 0.2 | 1.00 | 0.2 | 1.00 | 0.2 | 1.00 |
| Total | 20.00 | 100 | 20.00 | 100 | 20.00 | 100 | 20.00 | 100 | 20.00 | 100 |
| µmol/capsule | 11.4 | | 11.4 | | 11.4 | | 11.4 | | 11.4 | |
| Capsules/animal | 1 | | 1 | | 1 | | 1 | | 1 | |
| µmol/kg | 37 | | 37 | | 37 | | 37 | | 37 | |
| mg free base/kg | 8 | | 8 | | 8 | | 8 | | 8 | |

TABLE 6.2

Composition of capsules B containing indoximod in its free base or salt forms for oral dosing of rats at 185 µmol/kg

|  | indoximod Free Base | | indoximod HCl | | D1mT $0.5 \cdot H_3PO_4$ | |
|---|---|---|---|---|---|---|
| MW (g/mol) | 218.26 | | 254.76 | | 267.3 | |
|  | (mg) | % (w/w) | (mg) | % (w/w) | (mg) | % (w/w) |
| Active Ingredient | 6.25 | 31% | 7.3 | 37% | 7.65 | 38% |
| Microcrystalline Cellulose | 5.55 | 28% | 5.1 | 26% | 5.05 | 25% |
| Lactose Monohydrate | 5.55 | 28% | 5.1 | 26% | 5.05 | 25% |
| Croscarmellose Sodium | 2.45 | 12% | 2.3 | 12% | 2.05 | 10% |
| Magnesium Stearate | 0.2 | 1% | 0.2 | 1% | 0.2 | 1% |
| Total | 20.00 | 100 | 20.00 | 100 | 20.00 | 100 |
| µmol/capsule | 28.6 | | 28.6 | | 28.6 | |
| Capsules/animal | 2 | | 2 | | 2 | |
| µmol/kg | 185 | | 185 | | 185 | |
| mg free base/kg | 40 | | 40 | | 40 | |

TABLE 6.3

Composition of capsules C containing indoximod in its free base or salt forms for oral dosing of rats at 500 µmol/kg

|  | indoximod Free Base | | indoximod HCl | | D1mT $0.5 \cdot H_3PO_4$ | |
|---|---|---|---|---|---|---|
| MW (g/mol) | 218.26 | | 254.76 | | 267.3 | |
|  | (mg) | % (w/w) | (mg) | % (w/w) | (mg) | % (w/w) |
| Active Ingredient | 10.83 | 100% | 12.6 | 100% | 13.27 | 100% |
| Total | 10.83 | 100 | 12.6 | 100 | 13.27 | 100 |
| µmol/capsule | 50 | | 50 | | 50 | |
| Capsules/animal | 3 | | 3 | | 3 | |
| µmol/kg | 500 | | 500 | | 500 | |
| mg free base/kg | 110 | | 110 | | 110 | |

To test the pharmacokinetic profile achieved by dosing indoximod in its free base or salt forms, rats were dosed by intra-stomach delivery with 1 capsule A, 2 capsules B or 3 capsules C to achieve dose levels of 37, 185 and 500 µmol/kg (equivalent to 8, 40 and 110 mg/kg of indoximod, respectively). Rats were fasted 16 h prior to dosing to eliminate any confounding food effects, and food was returned 2 h after dosing. Blood samples were obtained from each rat at 0, 15 min, 30 min, 1 h, 2 h, 4 h, 6 h, 10 h, 24 h, 48 h and 72 h after dosing. The concentration of indoximod in plasma was determined by LC-MS/MS, and pharmacokinetic parameters were calculated using the software Win-NonLin (Certara).

The most relevant pharmacokinetic parameters that were evaluated were the maximum concentration of indoximod (Cmax) and total exposure ($AUC_{0 \to \infty}$). Tables 7.1-7.3 and FIG. 6 show a summary of the experimental results.

Indoximod hydrochloride salt form results in non-statistically significant decrease in Cmax at low dose level, a statistically significant increase at the intermediate dose and a statistically significant decrease at high level. The drug exposure (AUC) for the hydrochloride salt did not show a significant change at the low and high dose level but showed a significant increase at the intermediate level. The different behavior of indoximod hydrochloride in rodents compared to primates is unexpected based on the solubility and dissolution profile of this salt, and it does not follow a dose dependent trend, which highlights the importance of conducting species-specific and dose-dependent tests for the prediction of pharmacokinetic profiles in humans.

Indoximod phosphate and hemiphosphate showed a significant increase in Cmax and AUC at the low and intermediate dose levels but a significant decrease in Cmax and a non-statistically significant decrease in exposure at the highest dose level.

The dose-dependent correlation for Cmax and AUC for the free base, HCl and $PO_4H_3$ forms of indoximod is shown in FIG. 6. This figure shows an increase in Cmax for the HCl and $PO_4H_3$ salts with respect to the free base at the low and intermediate dose levels but a saturation in the Cmax dose-response curve at the highest dose level, which is not seen for the free base. The dose-response curve for AUC shows a more linear increase of AUC with dose, except for the $PO_4H_3$ salt which seems to increase less than dose proportional at the highest dose level tested.

Similarly, other salt forms of indoximod such as sulfate or mesylate increase the Cmax and AUC 30-40% when tested at 37 μmol/kg.

These tests indicate that the hydrochloride and phosphate salts of indoximod have increased solubility with respect to the free base form and display increased Cmax and AUC parameter values.

TABLE 7.1

Comparison of Cmax and total exposure (AUC -> ∞) between indoximod free base vs its salt forms in rats dosed at 37 μmol/kg

| Dose: 37 μmol/kg | indoximod Free Base | indoximod HCl | indoximod $H_3PO_4$ | indoximod $H_2SO_4$ | indoximod $CH_3SO_3H$ |
|---|---|---|---|---|---|
| Number of Animals | 11 | 4 | 10 | 4 | 4 |
| Cmax, average (μM) | 15.9 ± 8 | 9.5 ± 2 | 22.3 ± 9 | 22.6 ± 7 | 20.3 ± 2 |
| % Increase over indoximod Free Base | NA | −40 | 40 | 42 | 28 |
| P value | NA | 0.069 | 0.044 | 0.077 | 0.18 |
| AUC(0 -> ∞) (μM · h) | 390 ± 166 | 299 ± 77 | 558 ± 185 | 553 ± 196 | 537 ± 194 |
| % Increase over indoximod Free Base | NA | −23 | 43 | 42 | 38 |
| P value | NA | 0.159 | 0.018 | 0.065 | 0.2 |

TABLE 7.2

Comparison of Cmax and total exposure (AUC -> ∞) between indoximod free base vs its salt forms in rats dosed at 185 μmol/kg

| Dose: 185 μmol/kg | indoximod Free Base | indoximod HCl | indoximod $H_3PO_4$ |
|---|---|---|---|
| Number of Animals | 8 | 6 | 6 |
| Cmax, average (μM) | 20.8 ± 4 | 38.4 ± 10 | 40.9 ± 5 |
| % Increase over indoximod Free Base | NA | 84 | 96 |
| P value | NA | <0.0001 | <0.0001 |
| AUC(0 -> ∞) (μM · h) | 1080 ± 478 | 1493 ± 728 | 1446 ± 645 |
| % Increase over indoximod Free Base | NA | 38 | 34 |
| P value | NA | <0.0001 | <0.0001 |

TABLE 7.3

Comparison of Cmax and total exposure (AUC -> ∞) between indoximod free base vs its salt forms in rats dosed at 500 μmol/kg

| Dose: 500 μmol/kg | indoximod Free Base | indoximod HCl | indoximod $H_3PO_4$ |
|---|---|---|---|
| Number of Animals | 6 | 5 | 6 |
| Cmax, average (μM) | 76.2 ± 25 | 44.4 ± 8 | 37.2 ± 10 |
| % Increase over indoximod Free Base | NA | −42 | −51 |
| P value | NA | 0.012 | 0.0027 |
| AUC(0 -> ∞) (μM · h) | 2871 ± 1379 | 2706 ± 847 | 1902 ± 1288 |
| % Increase over indoximod Free Base | NA | −6 | −34 |
| P value | NA | 0.41 | 0.12 |

Example 7: Pharmacokinetic Testing of Indoximod Prodrugs in Liquid Formulation

The pharmacokinetic profile of indoximod obtained after oral administration of several indoximod prodrugs was tested in such a way that reflected only differences in intestinal permeability and conversion of prodrug to indoximod in vivo without reflecting differences in solid state form such as differences in polymorphic crystals or amorphous solids which may impact solubility or solubilization rate for the different prodrugs. Therefore, indoximod and each of its prodrugs was solubilized in appropriate vehicle which was either saline solution, Cremaphor®: ethanol: saline (10:10: 80), or Chremaphor:EtOH:saline:HCl (10:10:80:0.1N). Indoximod or its prodrugs were dissolved at a concentration of 1 mg/mL and dosed to rats by oral gavage at 10 mL/kg to achieve a final dose of 10 mg/kg; or dissolved at 25 mg/mL and dosed to rats by oral gavage at 2 mL/kg to achieve a final dose of 50 mg/kg; or dissolved at a concentration of 10 mg/mL and dosed orally to mice by oral gavage at 5 mL/kg to achieve a final dose of 50 mg/kg. Blood samples (0.1-0.2 mL) were collected from the femoral artery port from rats or by retro-orbital bleeding from mice and plasma was immediately collected by centrifugation and stored on dry ice to avoid prodrug hydrolysis after plasma collection. Blood samples were collected at 0, 15 min, 30 min, 1 h, 2 h, 4 h, 6 h, 10 h, 24 h, 48 h and 72 h after dosing from rats or at 0, 30 min, 1 h, 2 h, 4 h, 6 h, 16 h and 24 h after dosing from mice. The concentration of indoximod and of each prodrug in plasma was determined by LC-MS/MS, and pharmacokinetic parameters were calculated for indoximod and its prodrugs. The pharmacokinetic parameters reflect the average of individual parameter values obtained from each individual rat (n) or one common parameter from a single pharmacokinetic curve derived from blood samples obtained from a group of mice (n).

Tables 8.1 and 8.2 show the indoximod Cmax and AUC$_{(0\to\infty)}$ obtained after dosing either indoximod or each one of the test prodrugs. Since all rats were orally dosed at the same dose of 10 mg/kg, but each prodrug has different molecular weight, in order to compare the values of Cmax and AUC$_{(0\to\infty)}$ obtained after dosing each prodrug vs. dosing indoximod as a free base, the measured Cmax and AUC$_{(0\to\infty)}$ and were normalized by multiplying them by the ratio of MW$_{Prodrug}$/MW$_{indoximod}$, thus assuming linear pharmacokinetics within a ~2-fold dose range.

Table 8.1 shows that some prodrugs result in an effective increase in either Cmax, AUC or both pharmacokinetic parameters. Since the prodrugs were administered in completely soluble form, this suggests that those prodrugs that show enhanced Cmax and/or AUC of indoximod in plasma do so by a mechanism that involves a combination of factors including enhanced permeability of the prodrug through the intestinal cell wall, reduced clearance of the prodrug with respect to indoximod and good rate of conversion of the prodrug to indoximod in vivo. Not every prodrug form of indoximod resulted in enhanced maximum concentration and exposure of indoximod compared to administration of indoximod. In particular, exposure (AUC) to indoximod seems to be enhanced when dosing NLG-1563, NLG-1564, NLG-1566, NLG-1548, NLG-1572, NLG-1557, NLG-1559, NLG-1570, NLG-1565, NLG-1554, NLG-1558, NLG-1551, and NLG-1547, while indoximod Cmax seems to be enhanced when dosing NLG-1557, NLG-1558, NLG-1554, NLG-1566, NLG-1570, NLG-1283 and NLG-1263.

Table 8.2 shows prodrugs that did not result in an effective increase in indoximod Cmax nor indoximod exposure when dosed orally to rats at 10 mg/kg, indicating that some of these chemical substitutions may either decrease permeability, or the rate of conversion to indoximod or increase the rate of prodrug clearance by routes that do not result in conversion to indoximod, or a combination of those effects.

Table 8.3 shows prodrugs that were tested by oral dosing to rats at 50 mg/kg. NLG-1283 causes an increase in Cmax and AUC when dosed to rats at 50 mg/kg. However, this prodrug results in a decrease in Cmax and AUC when dosed to mice at 50 mg/kg. Conversely, the highly similar molecule NLG-1284 does not produce a significant increase in Cmax or AUC when dosed at 50 mg/kg to rats, but it does produce a significant increase in Cmax and AUC in mice, suggesting that different species have different rates of absorption, elimination and metabolization of these prodrugs and that minimal changes in molecular structure can affect the outcome in different species. A dose dependent PK was carried out in mice, which were dosed at 10, 50 and 100 mg/kg of indoximod, or at similar doses for prodrug NLG-1626 or NLG-1665. A caveat of the comparison between dosing prodrugs vs indoximod as a free base was that prodrugs were fully soluble in the dosing formulation, while indoximod was insoluble at doses of 50 and 100 mg/kg. This may result in a time-dependent controlled release effect for indoximod which could result in lower Cmax but higher AUCs than when dosed in fully soluble form. NLG-1626 and NLG-1665 resulted in a significant increase in indoximod Cmax compared to what is observed when dosing indoximod in suspension, at all doses tested. However, NLG-1626 showed a dose dependent increase AUC for indoximod, where the percentage of increase in AUC decreases at higher doses. Table 8.3 also indicates that formation of carbamates on the amino group of indoximod result in prodrugs with marked reduction in pharmacokinetic parameters for indoximod.

Example 8: Pharmacokinetic Testing of Indoximod Prodrug Salts in Solid Capsule Formulation in Rats To test which prodrugs have the best combined set of pharmacological properties (solubilization rate, solubility, intestinal permeability, clearance rate and rate of metabolization to indoximod) needed to achieve greater plasma concentrations of indoximod and increased exposure to indoximod after oral dosing in a capsule formulation, the prodrugs that showed enhanced indoximod Cmax or exposure when dosed in solution were prepared in several salt forms and mixed with excipients to form a powder blend. These blends were formulated so that each capsule contained the same molar dose of each prodrug. Gelatin capsules (Torpac, 20 mg capacity) were prepared containing 11 μmol/capsule A, 28 μmol/capsule B or 50 μmol/capsule C of indoximod free base (2.5, 6.3 or 11.4 mg/capsule, respectively) or its prodrugs in diverse salt forms, in an excipient blend consisting of microcrystalline cellulose, lactose monohydrate, croscarmellose sodium and magnesium stearate, in proportions shown in Tables 9.1a and 9.1b. The composition and uniformity of a representative sample of capsules from each batch was verified by weight and by LC-MS/MS to determine the average indoximod or prodrug content.

To test the pharmacokinetic profile achieved by dosing indoximod prodrugs in different salt forms, 1 capsule A (11 μmol/capsule) or 2 capsules B (28 μmol/capsule) or 3 capsules C (50 μmol/capsule) were dosed to rats by intrastomach delivery. The dose levels tested were equivalent to 8 mg/kg (37 μmol/kg) of indoximod equivalent when dosing 1 capsule A of 11 μmol/capsule, 40 mg/kg (185 μmol/kg) of indoximod equivalent when dosing 2 capsules B of 28 μmol/capsule and 110 mg/kg (500 μmol/kg) of indoximod equivalent when dosing 3 capsules C of 50 μmol/capsule. Rats were fasted 16 h prior to dosing to eliminate any confounding food effects, and food was returned 2 h after dosing. Blood samples were obtained from each rat at 0, 15 min, 30 min, 1 h, 2 h, 4 h, 6 h, 10 h, 24 h, 48 h and 72 h after dosing. The concentration of indoximod in plasma was determined by LC-MS/MS, and pharmacokinetic parameters were calculated using the software WinNonLin (Certara).

The most relevant evaluated pharmacokinetic parameters were the maximum concentration of indoximod (Cmax) and total indoximod exposure (AUC$_{0\to\infty}$). Tables 10.1 and 10.2 show a summary of the experimental results.

The statistical comparison of pharmacokinetic parameters indicated that ethyl N$^\alpha$-(L-leucyl)-1-methyl-D-tryptophanate in its hydrochloride (NLG-1564), phosphate (NLG-1665), mesylate (NLG-1666) or besylate (NLG-1671) salt forms dosed at 37-185 μmol/kg was able to significantly ($p<0.05$) increase exposure of indoximod by 33-127%, while its sulfate salt (NLG-1691) did not result in a significant increase in Cmax or AUC at those doses. Similarly, significant increases in Cmax were observed for NLG-1564, NLG-1665 and NLG-1666. At doses of 500 μmol/kg, NLG-1564 hydrochloride, showed a minor increase in Cmax and AUC compared to indoximod.

Table 10.2 shows that 2,3-dihydroxypropyl 1-methyl-D-tryptophanate in its phosphate (NLG-1626) form resulted in significant increase in Cmax (37-153%) and AUC (46-75%), while its hydrocholoride (NLG-1558), and sulfate (NLG-1628) salts resulted in less significant increases in Cmax and AUC. Interestingly, the mesylate salt of 2,3-dihydroxypropyl 1-methyl-D-tryptophanate (NLG-1627) resulted in a decrease in Cmax and AUC, thought this decrease was not statistically significant.

Table 10.2 also shows that ethyl $N^\alpha$-(L-methionyl)-1-methyl-D-tryptophanate (HCl, and phosphate salts, NLG-3272) show a statistically significant increase in Cmax and AUC at doses of 37-500 µmol/kg.

Other prodrugs that were studied included: a) ethyl $N^\alpha$-(L-glutaminyl)-1-methyl-D-tryptophanate (free base, HCl, phosphate or mesylate salts), b) $N^\alpha$-glycyl-1-methyl-D-tryptophan (HCl or phosphate salt), c) methyl $N^4$—((R)-1-ethoxy-3-(1-methyl-1H-indol-3-yl)-1-oxopropan-2-yl)-L-asparaginate (HCl form) and d) $N^\alpha$-(L-lysyl)-1-methyl-D-tryptophan (free base, HCl, sulfate or phosphate salts). These prodrugs resulted in minor and non-statistically significant variations in the Cmax or AUC for indoximod compared to an equivalent molar dose of indoximod (Table 10.3).

Interestingly, piperidin-4-ylmethyl 1-methyl-D-tryptophanate in its HCl or phosphate salt forms (NLG-1563 and NLG-1664) resulted in a statistically significant decrease in Cmax (69-79%, $p<0.004$) and AUC (54-64%, $p<0.014$) for indoximod. Since this compound showed an increase in Cmax (24%) and AUC (75%) when administered via oral solution, the difference in solubilization rate or final solubility may account for the observed differences when administered in powder form.

Example 9: Pharmacokinetic Testing of Indoximod Prodrug Salts in Solid Capsule Formulation in Cynomolgous Monkeys Since the rat shows a non-saturable linear increase in exposure with doses of indoximod of up to 100 mg/kg, while humans show a saturable exposure above doses of 10 mg/kg, we decided to evaluate two of the prodrug in primates, which may constitute a better model to predict human pharmacokinetics than rats. Cynomolgous monkeys (4.5-5 kg) were dosed with indoximod, NLG-1564 HCl or NLG-3272 HCl at doses of 92, 275 or 875 µmol/kg in a crossover study design where each animal received the same molar dose of either indoximod, NLG1564 HCl or NLG-3272 HCl every 7 days. Capsules were prepared according to the formulation described in Table 9.2. Monkeys were orally dosed with 1 or 3 capsules A (458 µmol/capsule) or 4 capsules B (1032 µmol/capsule). Blood samples were collected at 0, 5 min, 15 min, 30 min, 1, 2, 4, 8, 12, 24, 26 and 48 h post-dose, and the concentrations of prodrug and indoximod were analyzed by validated LC-MSMS methods.

The data in Table 11.1 shows that NLG-1564 HCl increases the Cmax of indoximod from 230-500% and AUC from 195-518% in a statistically significant manner. Similarly, NLG-3272 HCl increases the Cmax of indoximod from ~305-411% and AUC from 136-393% in a statistically significant manner. The increase in pharmacodynamics indicators in primates was unexpectedly superior from the results observed in rats, indicating that in primates, prodrugs of indoximod of the present invention can provide a significant improvement in the maximum concentration and exposure to indoximod and are expected to improve exposure to the drug and therapeutic efficacy in human patients.

TABLE 8.1

Cmax and AUC for indoximod after orally dosing rats with solutions of indoximod or its prodrugs

| Prodrug ID | Name | Salt form | MW (g/mol) | Dose (mg/kg) |
|---|---|---|---|---|
| indoximod | 1-methyl-D-tryptophan | HCl | 218 | 10 |
| NLG-1563 | piperidin-4-ylmethyl 1-methyl-D-tryptophanate | HCl | 389 | 10 |
| NLG-1564 | ethyl $N^\alpha$-(L-leucyl)-1-methyl-D-tryptophanate | HCl | 396 | 10 |
| NLG-1566 | ethyl $N^\alpha$-(L-glutaminyl)-1-methyl-D-tryptophanate | HCl | 411 | 10 |
| NLG-1548 | $N^\alpha$-(L-lysyl)-1-methyl-D-tryptophan | HCl | 419 | 10 |
| NLG-1572 | 2-(tetrahydro-2H-pyran-4-yl)ethyl 1-methyl-D-tryptophanate | HCl | 367 | 10 |
| NLG-1557 | 2-(dimethylamino)ethyl 1-methyl-D-tryptophanate | HCl | 362 | 10 |
| NLG-1559 | (2-ethoxy-2-oxido-1,3,2-dioxaphospholan-4-yl)methyl 1-methyl-D-tryptophanate | HCl | 419 | 10 |
| NLG-1570 | $N^\alpha$-(L-leucyl)-1-methyl-D-tryptophan | HCl | 368 | 10 |
| NLG-1565 | ethyl $N^\alpha$-(L-isoleucyl)-1-methyl-D-tryptophanate | HCl | 396 | 10 |
| NLG-1554 | $N^\alpha$-glycyl-1-methyl-D-tryptophan hydrochloride | HCl | 312 | 10 |
| NLG-1558 | 2,3-dihydroxypropyl 1-methyl-D-tryptophanate | HCl | 329 | 10 |
| NLG-1551 | O-(1-methyl-D-tryptophyl)-L-serine | HCl | 378 | 10 |
| NLG-1547 | $N^\alpha$-(L-glutamyl)-1-methyl-D-tryptophan | HCl | 384 | 10 |
| NLG-1283 | ethyl 1-methyl-D-tryptophanate | HCl | 283 | 10 |

| Prodrug ID | n | Cmax (µM) | Norm. Cmax (µM) | % Change in Norm. Cmax | $AUC_{(0\to\infty)}$ (µM·h) | Norm. $AUC_{(0\to\infty)}$ (µM·h) | % Change in Norm AUC |
|---|---|---|---|---|---|---|---|
| indoximod | 5 | 17.3 | 17.3 | 0 | 508 | 508 | 0 |
| NLG-1563 | 5 | 12.1 | 21.5 | 24 | 500 | 889 | 75 |
| NLG-1564 | 3 | 9.3 | 16.2 | −6 | 490 | 888 | 75 |
| NLG-1566 | 5 | 13 | 24.4 | 41 | 428 | 806 | 58 |
| NLG-1548 | 5 | 8.7 | 16.7 | −3 | 414 | 795 | 56 |
| NLG-1572 | 3 | 8.9 | 15 | −14 | 460 | 774 | 52 |
| NLG-1557 | 3 | 23.8 | 39.5 | 128 | 440 | 731 | 44 |
| NLG-1559 | 3 | 8.8 | 16.9 | −2 | 327 | 628 | 23 |
| NLG-1570 | 3 | 14.5 | 24.4 | 41 | 366 | 617 | 21 |
| NLG-1565 | 3 | 7.1 | 12.8 | −26 | 334 | 606 | 19 |
| NLG-1554 | 3 | 19.6 | 28 | 62 | 419 | 599 | 18 |
| NLG-1558 | 5 | 22.1 | 33.3 | 92 | 395 | 595 | 17 |
| NLG-1551 | 3 | 7.7 | 13.3 | −23 | 339 | 588 | 16 |
| NLG-1547 | 3 | 10 | 17.6 | 2 | 326 | 574 | 13 |
| NLG-1283 | 3 | 17 | 22 | 27 | 350 | 454 | −11 |

TABLE 8.2

Cmax and AUC for indoximod after orally dosing rats with solutions of indoximod or its prodrugs

| Prodrug ID | Name | Salt form | MW (g/mol) | Dose (mg/kg) |
|---|---|---|---|---|
| indoximod | 1-methyl-D-tryptophan | HCl | 218 | 10 |
| NLG-1575 | N$^\alpha$-(L-phenylalanyl)-1-methyl-D-tryptophan | HCl | 402 | 10 |
| NLG-1560 | N$^\alpha$-(L-tryptophyl)-1-methyl-D-tryptophan | HCl | 368 | 10 |
| NLG-1569 | N$^\alpha$-(L-glutaminyl)-1-methyl-D-tryptophan | HCl | 383 | 10 |
| NLG-1553 | N$^\alpha$-(L-valyl)-1-methyl-D-tryptophan | HCl | 354 | 10 |
| NLG-1574 | ethyl N$^\alpha$-(L-phenylalanyl)-1-methyl-D-tryptophanate | HCl | 430 | 10 |
| NLG-1571 | N$^\alpha$-(L-isoleucyl)-1-methyl-D-tryptophan | HCl | 368 | 10 |
| NLG-1555 | N$^\alpha$-(L-alanyl)-1-methyl-D-tryptophan | HCl | 326 | 10 |
| NLG-1549 | 1-methyl-N$^\alpha$-(1-methyl-D-tryptophyl)-D-tryptophan | HCl | 455 | 10 |
| NLG-1556 | 1-methyl-D-tryptophyl-L-valine | HCl | 354 | 10 |
| NLG-1546 | N$^\alpha$-(D-tryptophyl)-1-methyl-D-tryptophan | HCl | 441 | 10 |
| NLG-1561 | 2-(piperidin-4-yl)ethyl 1-methyl-D-tryptophanate | HCl | 402 | 10 |
| NLG-1567 | ethyl N$^\alpha$-(D-tryptophyl)-1-methyl-D-tryptophanate | HCl | 469 | 10 |

| Prodrug ID | n | Cmax ($\mu$M) | Norm. Cmax ($\mu$M) | % Change in Norm. Cmax | AUC$_{(0->\infty)}$ ($\mu$M·h) | Norm. AUC$_{(0->\infty)}$ ($\mu$M·h) | % Change in Norm AUC |
|---|---|---|---|---|---|---|---|
| indoximod | 5 | 17.3 | 17.3 | 0 | 508 | 508 | 0 |
| NLG-1575 | 3 | 6.4 | 11.9 | −31 | 231 | 425 | −16 |
| NLG-1560 | 3 | 7.1 | 12 | −31 | 246 | 415 | −18 |
| NLG-1569 | 3 | 4.8 | 8.5 | −51 | 212 | 372 | −27 |
| NLG-1553 | 3 | 8.8 | 14.2 | −18 | 209 | 338 | −33 |
| NLG-1574 | 3 | 4 | 7.9 | −54 | 167 | 329 | −35 |
| NLG-1571 | 3 | 7.4 | 12.5 | −28 | 187 | 316 | −38 |
| NLG-1555 | 3 | 9 | 13.4 | −22 | 207 | 310 | −39 |
| NLG-1549 | 3 | 1.5 | 3 | −83 | 126 | 262 | −48 |
| NLG-1556 | 3 | 1 | 1.6 | −91 | 125 | 202 | −60 |
| NLG-1546 | 3 | 1.6 | 3.2 | −82 | 90 | 182 | −64 |
| NLG-1561 | 3 | 1.3 | 2.4 | −86 | 59.9 | 110 | −78 |
| NLG-1567 | 3 | 0 | 0 | −100 | 0 | 0 | −100 | n: number of rats used to determine the average pharmacokinetic parameters.

Cmax ($\mu$M): maximum concentration of indoximod observed in plasma. Value is the average of n values.

Norm. Cmax ($\mu$M): maximum average concentration of indoximod calculated by multiplying the observed Cmax of indoximod in plasma by the ratio of MW of each prodrug and the MW of indoximod and by the ratio of dose of indoximod and the prodrug (in mg/kg). This normalizes Cmax to the same molar dose ($\mu$mol/kg).

% Change in Norm. Cmax: Calculated as [Cmax (indoximod from Prodrug)/Cmax(indoximod from indoximod) − 1] × 100

AUC$_{(0->\infty)}$ ($\mu$M · h): Area under the curve [indoximod] vs Time observed in plasma. Value is the average of n values.

Norm. AUC$_{(0->\infty)}$ ($\mu$M · h): average AUC calculated by multiplying the observed AUC$_{(0->\infty)}$ of indoximod in plasma by the ratio of MW of each prodrug and the MW of indoximod and by the ratio of dose of indoximod and the prodrug (in mg/kg). This normalizes AUC to the same molar dose ($\mu$mol/kg).

% Change in AUC$_{(0->\infty)}$: Calculated as [AUC$_{(0->\infty)}$ (indoximod from Prodrug)/AUC$_{(0->\infty)}$ (indoximod from indoximod) − 1] × 100

TABLE 8.3

Pharmacokinetic parameters for indoximod after orally dosing mice or rats with solutions of indoximod or its prodrugs

| Drug/Prodrug | Name | Salt form | MW (g/mol) | Dose (mg/kg) | Route | Species |
|---|---|---|---|---|---|---|
| indoximod | 1-methyl-D-tryptophan | HCl | 218 | 50 | PO | Rat |
| NLG-1277 | N$^\alpha$-(ethoxycarbonyl)-1-methyl-D-tryptophan | FB | 290 | 50 | PO | Rat |
| NLG-1278 | 1-methyl-N$^\alpha$-((neopentyloxy)carbonyl)-D-tryptophan | FB | 333 | 50 | PO | Rat |
| NLG-1280 | 1-methyl-N$^\alpha$-((neopentyloxy)carbonyl)-D-tryptophan | FB | 290 | 50 | PO | Rat |
| NLG-1283 | ethyl 1-methyl-D-tryptophanate | HCl | 246 | 50 | PO | Rat |
| NLG-1284 | isopropyl 1-methyl-D-tryptophanate | FB | 261 | 50 | PO | Rat |
| NLG-1338 | benzyl 1-methyl-D-tryptophanate | HCl | 345 | 50 | PO | Rat |
| NLG-1546 | N$^\alpha$-(D-tryptophyl)-1-methyl-D-tryptophan | HCl | 441 | 50 | PO | Rat |
| indoximod | 1-methyl-D-tryptophan | FB | 218 | 10 | PO | Mouse |
| indoximod | 1-methyl-D-tryptophan | FB | 218 | 50 | PO | Mouse |
| indoximod | 1-methyl-D-tryptophan | HCl | 218 | 50 | PO | Mouse |
| indoximod | 1-methyl-D-tryptophan | FB | 218 | 100 | PO | Mouse |
| NLG-1626 | 2,3-dihydroxypropyl 1-methyl-D-tryptophanate | H$_3$PO$_4$ | 390 | 13.3 | PO | Mouse |
| NLG-1626 | 2,3-dihydroxypropyl 1-methyl-D-tryptophanate | H$_3$PO$_4$ | 390 | 66.5 | PO | Mouse |
| NLG-1626 | 2,3-dihydroxypropyl 1-methyl-D-tryptophanate | H$_3$PO$_4$ | 390 | 133 | PO | Mouse |
| NLG-1665 | ethyl N$^\alpha$-(L-leucyl)-1-methyl-D-tryptophanate | H$_3$PO$_4$ | 457 | 14 | PO | Mouse |
| NLG-1665 | ethyl N$^\alpha$-(L-leucyl)-1-methyl-D-tryptophanate | H$_3$PO$_4$ | 457 | 70 | PO | Mouse |
| NLG-1665 | ethyl N$^\alpha$-(L-leucyl)-1-methyl-D-tryptophanate | H$_3$PO$_4$ | 457 | 140 | PO | Mouse |
| NLG-1277 | N$^\alpha$-(ethoxycarbonyl)-1-methyl-D-tryptophan | FB | 290 | 50 | PO | Mouse |
| NLG-1280 | 1-methyl-N$^\alpha$-((neopentyloxy)carbonyl)-D-tryptophan | FB | 290 | 50 | PO | Mouse |

TABLE 8.3-continued

Pharmacokinetic parameters for indoximod after orally dosing mice or rats with solutions of indoximod or its prodrugs

| | | | | | | | |
|---|---|---|---|---|---|---|---|
| NLG-1283 | ethyl 1-methyl-D-tryptophanate | | HCl | 246 | 50 | PO | Mouse |
| NLG-1284 | isopropyl 1-methyl-D-tryptophanate | | FB | 261 | 50 | PO | Mouse |

| Drug/Prodrug | n | Tmax (h) | $t_{1/2}$ (h) | Cmax (μM) | Dose Norm. Cmax (μM) | % Change in Norm. Cmax | $AUC_{(0 \to \infty)}$ (μM · h) | Dose Norm. $AUC_{(0 \to \infty)}$ (μM · h) | % Increase in Norm AUC |
|---|---|---|---|---|---|---|---|---|---|
| indoximod | 1 | 8 | 28 | 27 | 27 | 0% | 1323 | 1323 | 0% |
| NLG-1277 | 1 | 4 | 25 | 4.5 | 6.0 | −78% | 172 | 229 | −83% |
| NLG-1278 | 1 | 2 | 27.4 | 0.10 | 0.15 | −99% | 3.6 | 5.5 | −100% |
| NLG-1280 | 1 | 8 | 30 | 5.4 | 7.2 | −73% | 281 | 374 | −72% |
| NLG-1283 | 1 | 6 | 27 | 58 | 66 | 143% | 2645 | 2988 | 126% |
| NLG-1284 | 1 | 6 | 21 | 23.4 | 28 | 4% | 877 | 1051 | −21% |
| NLG-1338 | 1 | 8 | 20 | 17.8 | 28 | 4% | 650 | 1028 | −22% |
| NLG-1546 | 3 | 10 | 58 | 1.6 | 3.2 | −88% | 90 | 182 | −86% |
| indoximod | 10 | 0.5 | 1.8 | 9 | 9 | 0% | 34 | 34 | 0% |
| indoximod | 10 | 1 | 2.7 | 30 | 30 | 0% | 137 | 137 | 0% |
| indoximod | 7 | 1 | 2.2 | 16 | 16 | −47% | 61 | 61 | −55% |
| indoximod | 10 | 1 | 3.5 | 43 | 43 | 0% | 325 | 325 | 0% |
| NLG-1626 | 10 | 0.5 | 4.6 | 13.3 | 18 | 99% | 44 | 59 | 74% |
| NLG-1626 | 10 | 0.75 | 4.4 | 49.1 | 66 | 120% | 162 | 218 | 59% |
| NLG-1626 | 10 | 0.75 | 3.7 | 71 | 96 | 122% | 242 | 326 | 0% |
| NLG-1665 | 10 | 0.5 | 1.5 | 6.5 | 10 | 8% | 19 | 28 | −18% |
| NLG-1665 | 10 | 0.75 | 2.3 | 33.3 | 50 | 66% | 98 | 147 | 7% |
| NLG-1665 | 10 | 0.5 | 2.7 | 77.6 | 116 | 170% | 168 | 252 | −23% |
| NLG-1277 | 7 | 0.5 | 1.1 | 0.13 | 0.17 | −99% | 0.29 | 0.39 | −100% |
| NLG-1280 | 7 | NA | NA | BLQ | BLQ | −100% | 0 | 0.0 | −100% |
| NLG-1283 | 7 | 0.25 | 3.9 | 24 | 27.1 | −10% | 27 | 30.5 | −78% |
| NLG-1284 | 7 | 0.5 | 4.4 | 70 | 84 | 180% | 218 | 261 | 91% |

TABLE 9.1a

Capsule Compositions - Rat Oral Dosing

| Active Ingredient | Name | Salt form | Dose (μmol/capsule) | n of capsules/rat | % w/w Active Ingredient | Micro-crystalline Cellulose | Lactose mono-hydrate | Cross-carmelose | Magne-sium Stearate |
|---|---|---|---|---|---|---|---|---|---|
| indoximod | 1-methyl-D-tryptophan | free base | 11 | 1 | 12.5 | 37.3 | 37.3 | 12.0 | 1.0 |
| indoximod | 1-methyl-D-tryptophan | free base | 28 | 2 | 31.3 | 27.8 | 27.8 | 12.3 | 1.0 |
| indoximod | 1-methyl-D-tryptophan | free base | 50 | 3 | 100 | 0 | 0 | 0 | 0 |
| NLG-1676 | $N^\alpha$-(L-lysyl)-1-methyl-D-tryptophan | free base | 11 | 1 | 19.8 | 33.0 | 33.0 | 13.2 | 1.0 |
| NLG-1548 | $N^\alpha$-(L-lysyl)-1-methyl-D-tryptophan | HCl | 11 | 1 | 24.0 | 32.5 | 32.5 | 10.0 | 1.0 |
| NLG-1669 | $N^\alpha$-(L-lysyl)-1-methyl-D-tryptophan | $H_2SO_4$ | 11 | 1 | 25.5 | 31.5 | 31.5 | 10.5 | 1.0 |
| NLG-1670 | $N^\alpha$-(L-lysyl)-1-methyl-D-tryptophan | $H_3PO_4$ | 11 | 1 | 31.1 | 29.0 | 29.0 | 9.9 | 1.0 |
| NLG-1564 | ethyl $N^\alpha$-(L-leucyl)-1-methyl-D-tryptophanate | HCl | 11 | 1 | 22.7 | 32.0 | 32.0 | 12.3 | 1.0 |
| NLG-1564 | ethyl $N^\alpha$-(L-leucyl)-1-methyl-D-tryptophanate | HCl | 28 | 2 | 57.6 | 16.2 | 16.2 | 10.0 | 1.0 |
| NLG-1564 | ethyl $N^\alpha$-(L-leucyl)-1-methyl-D-tryptophanate | HCl | 50 | 3 | 100 | 0 | 0 | 0 | 0 |
| NLG-1665 | ethyl $N^\alpha$-(L-leucyl)-1-methyl-D-tryptophanate | $H_3PO_4$ | 11 | 1 | 26.0 | 30.8 | 30.8 | 11.5 | 1.0 |
| NLG-1665 | ethyl $N^\alpha$-(L-leucyl)-1-methyl-D-tryptophanate | $H_3PO_4$ | 28 | 2 | 53.1 | 17.7 | 17.7 | 10.5 | 1.0 |
| NLG-1666 | ethyl $N^\alpha$-(L-leucyl)-1-methyl-D-tryptophanate | $CH_3SO_3H$ | 11 | 1 | 25.3 | 31.3 | 31.3 | 11.2 | 1.0 |
| NLG-1671 | ethyl $N^\alpha$-(L-leucyl)-1-methyl-D-tryptophanate | Besylate | 11 | 1 | 29.6 | 30.0 | 30.0 | 9.4 | 1.0 |
| NLG-1691 | ethyl $N^\alpha$-(L-leucyl)-1-methyl-D-tryptophanate | $H_2SO_4$ | 11 | 1 | 23.4 | 31.5 | 31.5 | 12.6 | 1.0 |
| NLG-1558 | 2,3-dihydroxypropyl 1-methyl-D-tryptophanate | HCl | 11 | 1 | 18.8 | 33.5 | 33.5 | 13.2 | 1.0 |
| NLG-1626 | 2,3-dihydroxypropyl 1-methyl-D-tryptophanate | $H_3PO_4$ | 11 | 1 | 22.4 | 32.5 | 32.5 | 11.6 | 1.0 |
| NLG-1626 | 2,3-dihydroxypropyl 1-methyl-D-tryptophanate | $H_3PO_4$ | 28 | 2 | 55.9 | 16.7 | 16.7 | 9.6 | 1.0 |
| NLG-1627 | 2,3-dihydroxypropyl 1-methyl-D-tryptophanate | $CH_3SO_3H$ | 11 | 1 | 22.2 | 32.3 | 32.3 | 12.3 | 1.0 |
| NLG-1628 | 2,3-dihydroxypropyl 1-methyl-D-tryptophanate | $H_2SO_4$ | 11 | 1 | 19.6 | 33.5 | 33.5 | 12.4 | 1.0 |
| NLG-1672 | ethyl $N^\alpha$-(L-glutaminyl)-1-methyl-D-tryptophanate | free base | 11 | 1 | 21.4 | 32.5 | 32.5 | 12.5 | 1.0 |
| NLG-1566 | ethyl $N^\alpha$-(L-glutaminyl)-1-methyl-D-tryptophanate | HCl | 11 | 1 | 23.5 | 31.3 | 31.3 | 13.0 | 1.0 |
| NLG-1629 | ethyl $N^\alpha$-(L-glutaminyl)-1-methyl-D-tryptophanate | $H_3PO_4$ | 11 | 1 | 27.1 | 30.5 | 30.5 | 10.9 | 1.0 |
| NLG-1630 | ethyl $N^\alpha$-(L-glutaminyl)-1-methyl-D-tryptophanate | $H_2SO_4$ | 11 | 1 | 24.3 | 31.2 | 31.2 | 12.2 | 1.0 |
| NLG-1631 | ethyl $N^\alpha$-(L-glutaminyl)-1-methyl-D-tryptophanate | $CH_3SO_3H$ | 11 | 1 | 26.9 | 30.0 | 30.0 | 12.1 | 1.0 |

TABLE 9.1b

Capsule Compositions - Rat Oral Dosing

| Active Ingredient | Name | Salt form | Dose (μmol/ capsule) | n of capsules/ rat | % w/w Active Ingredient | Micro-crystalline Cellulose | Lactose mono-hydrate | Cross-carmelose | Magnesium Stearate |
|---|---|---|---|---|---|---|---|---|---|
| NLG-1563 | piperidin-4-ylmethyl 1-methyl-D-tryptophanate | HCl | 11 | 1 | 22.2 | 32.0 | 32.0 | 12.8 | 1.0 |
| NLG-1664 | piperidin-4-ylmethyl 1-methyl-D-tryptophanate | $H_3PO_4$ | 11 | 1 | 29.3 | 28.8 | 28.8 | 12.2 | 1.0 |
| NLG-1663 | piperidin-4-ylmethyl 1-methyl-D-tryptophanate | $H_2SO_4$ | 11 | 1 | 27.6 | 29.5 | 29.5 | 12.5 | 0.9 |
| NLG-1585 | methyl $N^4$-((R)-1-ethoxy-3-(1-methyl-1H-indol-3-yl)-1-oxopropan-2-yl)-L-asparaginate | HCl | 11 | 1 | 23.6 | 31.5 | 31.5 | 12.4 | 1.0 |
| NLG-1554 | $N^\alpha$-glycyl-1-methyl-D-tryptophan hydrochloride | HCl | 11 | 1 | 17.9 | 33.5 | 33.5 | 14.1 | 1.0 |
| NLG-1677 | $N^\alpha$-glycyl-1-methyl-D-tryptophan hydrochloride | $H_3PO_4$ | 11 | 1 | 22.2 | 31.7 | 31.7 | 13.4 | 0.9 |
| NLG-3272 | ethyl $N^\alpha$-(L-methionyl)-1-methyl-D-tryptophanate | $H_3PO_4$ | 11 | 1 | 27.2 | 30.4 | 30.4 | 11.0 | 1.0 |
| NLG-3272 | ethyl $N^\alpha$-(L-methionyl)-1-methyl-D-tryptophanate | $H_3PO_4$ | 28 | 2 | 48.3 | 21.6 | 21.6 | 7.8 | 0.7 |
| NLG-3272 | ethyl $N^\alpha$-(L-methionyl)-1-methyl-D-tryptophanate | HCl | 11 | 1 | 23.7 | 31.9 | 31.9 | 11.5 | 1.0 |
| NLG-3272 | ethyl $N^\alpha$-(L-methionyl)-1-methyl-D-tryptophanate | HCl | 28 | 2 | 43.7 | 23.5 | 23.5 | 8.5 | 0.8 |
| NLG-3272 | ethyl $N^\alpha$-(L-methionyl)-1-methyl-D-tryptophanate | HCl | 50 | 3 | 100 | 0 | 0 | 0 | 0 |
| NLG-3380 | $N^\alpha$-(L-methionyl)-1-methyl-D-tryptophan | HCl | 11 | 1 | 23.3 | 32.0 | 32.0 | 11.5 | 1.0 |
| NLG-3380 | $N^\alpha$-(L-methionyl)-1-methyl-D-tryptophan | HCl | 28 | 2 | 42 | 24.2 | 24.2 | 8.8 | 0.8 |
| NLG-3380 | $N^\alpha$-(L-methionyl)-1-methyl-D-tryptophan | $H_3PO_4$ | 28 | 2 | 45.6 | 22.7 | 22.7 | 8.2 | 0.7 |

TABLE 9.2

Capsule Compositions - Monkey Oral Dosing

| Active Ingredient | Name | Salt form | Dose (μmol/ capsule) | n of capsules dosed | % w/w Active Ingredient | Micro-crystalline Cellulose | Man-nitol | Cross-carmelose | Magnesium Stearate |
|---|---|---|---|---|---|---|---|---|---|
| indoximod | 1-methyl-D-tryptophan | free base | 458 | 1, 3 | 70 | 12.5 | 12.5 | 5.0 | 0.0 |
| indoximod | 1-methyl-D-tryptophan | free base | 1032 | 4 | 70 | 12.5 | 12.5 | 5.0 | 0.0 |
| NLG-1564 | ethyl $N^\alpha$-(L-leucyl)-1-methyl-D-tryptophanate | HCl | 458 | 1, 3 | 70 | 12.5 | 12.5 | 5.0 | 0.0 |
| NLG-1564 | ethyl $N^\alpha$-(L-leucyl)-1-methyl-D-tryptophanate | HCl | 1032 | 4 | 70 | 12.5 | 12.5 | 5.0 | 0.0 |
| NLG-3272 | ethyl $N^\alpha$-(L-methionyl)-1-methyl-D-tryptophanate | HCl | 458 | 1, 3 | 70 | 12.5 | 12.5 | 5.0 | 0.0 |
| NLG-3272 | ethyl $N^\alpha$-(L-methionyl)-1-methyl-D-tryptophanate | HCl | 1032 | 4 | 70 | 12.5 | 12.5 | 5.0 | 0.0 |

TABLE 10.1

Comparison of Cmax and total exposure ($AUC_{0\rightarrow\infty}$) between indoximod free base vs. its prodrugs in different salt forms after oral dosing of rats with capsules

| Drug/ Prodrug ID | Name | Salt form | Dose (μmol/ kg) | n | Cmax (μM) | % Change Cmax | p Value | $AUC_{(0\rightarrow\infty)}$ (μM · h) | % Change in AUC | pValue |
|---|---|---|---|---|---|---|---|---|---|---|
| indoximod | 1-methyl-D-tryptophan | free base | 37 | 11 | 15.9 ± 8 | 0 | | 390 ± 166 | 0 | |
| indoximod | 1-methyl-D-tryptophan | free base | 185 | 8 | 20.8 ± 4 | 0 | | 1080 ± 478 | 0 | |
| indoximod | 1-methyl-D-tryptophan | free base | 500 | 6 | 76.2 ± 25 | 0 | | 2871 ± 1379 | 0 | |
| NLG-1676 | $N^\alpha$-(L-lysyl)-1-methyl-D-tryptophan | free base | 37 | 4 | 13.3 ± 2 | −17 | 0.26 | 340 ± 57 | −13 | 0.28 |
| NLG-1548 | $N^\alpha$-(L-lysyl)-1-methyl-D-tryptophan | HCl | 37 | 4 | 17.2 ± 9 | 8 | 0.39 | 350 ± 83 | −10 | 0.33 |
| NLG-1669 | $N^\alpha$-(L-lysyl)-1-methyl-D-tryptophan | $H_2SO_4$ | 37 | 4 | 15.3 ± 5 | −4 | 0.44 | 446 ± 101 | 10 | 0.27 |
| NLG-1670 | $N^\alpha$-(L-lysyl)-1-methyl-D-tryptophan | $H_3PO_4$ | 37 | 4 | 11.5 ± 4 | 4 | 0.15 | 325 ± 61 | −17 | 0.23 |
| NLG-1564 | ethyl $N^\alpha$-(L-leucyl)-1-methyl-D-tryptophanate | HCl | 37 | 4 | 30.4 ± 10 | 92 | 0.005 | 664 ± 134 | 70 | 0.006 |
| NLG-1564 | ethyl $N^\alpha$-(L-leucyl)-1-methyl-D-tryptophanate | HCl | 185 | 8 | 44.2 ± 10 | 112 | <0.0001 | 1860 ± 609 | 87 | <0.0001 |
| NLG-1564 | ethyl $N^\alpha$-(L-leucyl)-1-methyl-D-tryptophanate | HCl | 500 | 6 | 80.0 ± 22 | 5 | 0.39 | 3300 ± 391 | 15 | 0.26 |
| NLG-1665 | ethyl $N^\alpha$-(L-leucyl)-1-methyl-D-tryptophanate | $H_3PO_4$ | 37 | 7 | 29.2 ± 13 | 84 | 0.008 | 628 ± 145 | 61 | 0.003 |
| NLG-1665 | ethyl $N^\alpha$-(L-leucyl)-1-methyl-D-tryptophanate | $H_3PO_4$ | 185 | 10 | 35.3 ± 7 | 69 | 0.0001 | 1433 ± 858 | 33 | 0.024 |
| NLG-1666 | ethyl $N^\alpha$-(L-leucyl)-1-methyl-D-tryptophanate | $CH_3SO_3H$ | 37 | 4 | 33.6 ± 3 | 111 | 0.0004 | 886 ± 273 | 127 | 0.0004 |
| NLG-1671 | ethyl $N^\alpha$-(L-leucyl)-1-methyl-D-tryptophanate | Besylate | 37 | 4 | 20.5 ± 2 | 29 | 0.14 | 565 ± 82 | 45 | 0.034 |

TABLE 10.1-continued

Comparison of Cmax and total exposure (AUC$_{0\to\infty}$) between indoximod free base vs. its prodrugs in different salt forms after oral dosing of rats with capsules

| Drug/ Prodrug ID | Name | Salt form | Dose (μmol/ kg) | n | Cmax (μM) | % Change Cmax | p Value | AUC$_{(0\to\infty)}$ (μM·h) | % Change in AUC | pValue |
|---|---|---|---|---|---|---|---|---|---|---|
| NLG-1691 | ethyl N$^\alpha$-(L-leucyl)-1-methyl-D-tryptophanate | H$_2$SO$_4$ | 37 | 4 | 12.2 ± 4 | −23 | 0.19 | 369 ± 145 | −5 | 0.41 |

TABLE 10.2

Comparison of Cmax and total exposure (AUC$_{0\to\infty}$) between indoximod free base vs. its prodrugs in different salt forms after oral dosing of rats with capsules

| Drug/ Prodrug ID | Name | Salt form | Dose (μmol/ kg) | n | Cmax (μM) | % Change Cmax | p Value | AUC$_{(0\to\infty)}$ (μM·h) | % Change in AUC | pValue |
|---|---|---|---|---|---|---|---|---|---|---|
| indoximod | 1-methyl-D-tryptophan | free base | 37 | 11 | 15.9 ± 8 | 0 | | 390 ± 166 | 0 | |
| indoximod | 1-methyl-D-tryptophan | free base | 185 | 8 | 20.8 ± 4 | 0 | | 1080 ± 478 | 0 | |
| indoximod | 1-methyl-D-tryptophan | free base | 500 | 6 | 76.2 ± 25 | 0 | | 2871 ± 1379 | 0 | |
| NLG-1558 | 2,3-dihydroxypropyl 1-methyl-D-tryptophanate | HCl | 37 | 4 | 20.2 ± 5 | 28 | 0.16 | 472 ± 58 | 21 | 0.18 |
| NLG-1626 | 2,3-dihydroxypropyl 1-methyl-D-tryptophanate | H$_3$PO$_4$ | 37 | 8 | 21.7 ± 3 | 37 | 0.032 | 571 ± 95 | 46 | 0.0067 |
| NLG-1626 | 2,3-dihydroxypropyl 1-methyl-D-tryptophanate | H$_3$PO$_4$ | 185 | 7 | 52.8 ± 23 | 153 | 0.0002 | 1896 ± 765 | 75 | 0.014 |
| NLG-1627 | 2,3-dihydroxypropyl 1-methyl-D-tryptophanate | CH$_3$SO$_3$H | 37 | 4 | 11.6 ± 5 | −27 | 0.16 | 285 ± 39 | −27 | 0.12 |
| NLG-1628 | 2,3-dihydroxypropyl 1-methyl-D-tryptophanate | H$_2$SO$_4$ | 37 | 4 | 17.6 ± 2 | 2 | 0.34 | 472 ± 120 | 21 | 0.19 |
| NLG-3380 | N$^\alpha$-(L-methionyl)-1-methyl-D-tryptophan | HCl | 37 | 8 | 18.4 ± 7 | 16 | 0.25 | 485 ± 130 | 24 | 0.099 |
| NLG-3380 | N$^\alpha$-(L-methionyl)-1-methyl-D-tryptophan | HCl | 185 | 8 | 92.7 ± 69 | 345 | 0.005 | 3043 ± 2700 | 181 | 0.003 |
| NLG-3380 | N$^\alpha$-(L-methionyl)-1-methyl-D-tryptophan | H$_3$PO$_4$ | 185 | 2 | 45.4 ± 15 | 118 | 0.0009 | 1794 ± 761 | 66 | 0.00002 |
| NLG-3272 | ethyl N$^\alpha$-(L-methionyl)-1-methyl-D-tryptophanate | H$_3$PO$_4$ | 37 | 8 | 21.0 ± 11 | 32 | 0.13 | 400 ± 136 | 2 | 0.45 |
| NLG-3272 | ethyl N$^\alpha$-(L-methionyl)-1-methyl-D-tryptophanate | H$_3$PO$_4$ | 185 | 8 | 31.1 ± 8 | 49 | 0.003 | 1236 ± 498 | 14 | 0.27 |
| NLG-3272 | ethyl N$^\alpha$-(L-methionyl)-1-methyl-D-tryptophanate | HCl | 37 | 8 | 19.2 ± 6 | 21 | 0.16 | 439 ± 114 | 13 | 0.24 |
| NLG-3272 | ethyl N$^\alpha$-(L-methionyl)-1-methyl-D-tryptophanate | HCl | 185 | 8 | 52.4 ± 15 | 152 | <0.0001 | 1898 ± 852 | 76 | 0.017 |
| NLG-3272 | ethyl N$^\alpha$-(L-methionyl)-1-methyl-D-tryptophanate | HCl | 500 | 6 | 121 ± 46 | 59 | 0.031 | 4269 ± 1255 | 49 | 0.048 |

TABLE 10.3

Comparison of Cmax and total exposure (AUC$_{0\to\infty}$) between indoximod free base vs. its prodrugs in different salt forms after oral dosing of rats with capsules

| Drug/ Prodrug ID | Name | Salt form | Dose (μmol/ kg) | n | Cmax (μM) | % Change Cmax | p Value | AUC$_{(0\to\infty)}$ (μM·h) | % Change in AUC | pValue |
|---|---|---|---|---|---|---|---|---|---|---|
| indoximod | 1-methyl-D-tryptophan | free base | 37 | 11 | 15.9 ± 8 | | | 390 ± 166 | | |
| indoximod | 1-methyl-D-tryptophan | free base | 185 | 8 | 20.8 ± 4 | | | 1080 ± 478 | | |
| indoximod | 1-methyl-D-tryptophan | free base | 500 | 6 | 76.2 ± 25 | | | 2871 ± 1379 | | |
| NLG-1672 | ethyl N$^\alpha$-(L-glutaminyl)-1-methyl-D-tryptophanate | free base | 37 | 4 | 16.7 ± 9 | 5 | 0.43 | 327 ± 12 | −16 | 0.24 |
| NLG-1566 | ethyl N$^\alpha$-(L-glutaminyl)-1-methyl-D-tryptophanate | HCl | 37 | 4 | 17.8 ± 4 | 12 | 0.33 | 386 ± 89 | −1 | 0.48 |
| NLG-1629 | ethyl N$^\alpha$-(L-glutaminyl)-1-methyl-D-tryptophanate | H$_3$PO$_4$ | 37 | 4 | 10.9 ± 3 | −32 | 0.12 | 280 ± 21 | −28 | 0.11 |
| NLG-1630 | ethyl N$^\alpha$-(L-glutaminyl)-1-methyl-D-tryptophanate | H$_2$SO$_4$ | 37 | 4 | 19 ± 8 | 20 | 0.25 | 314 ± 105 | −20 | 0.21 |
| NLG-1631 | ethyl N$^\alpha$-(L-glutaminyl)-1-methyl-D-tryptophanate | CH$_3$SO$_3$H | 37 | 4 | 16.5 ± 6 | 4 | 0.45 | 342 ± 97 | −12 | 0.3 |
| NLG-1563 | piperidin-4-ylmethyl 1-methyl-D-tryptophanate | HCl | 37 | 4 | 4.9 ± 0.4 | −69 | 0.008 | 180 ± 18 | −54 | 0.014 |

TABLE 10.3-continued

Comparison of Cmax and total exposure (AUC$_{0->\infty}$) between indoximod free base vs. its prodrugs in different salt forms after oral dosing of rats with capsules

| Drug/ Prodrug ID | Name | Salt form | Dose (μmol/ kg) | n | Cmax (μM) | % Change Cmax | p Value | AUC$_{(0->\infty)}$ (μM · h) | % Change in AUC | pValue |
|---|---|---|---|---|---|---|---|---|---|---|
| NLG-1664 | piperidin-4-ylmethyl 1-methyl-D-tryptophanate | H$_3$PO$_4$ | 37 | 4 | 3.3 ± 1 | −79 | 0.004 | 141 ± 45 | −64 | 0.006 |
| NLG-1585 | methyl N$^4$-((R)-2-ethoxy-3-(1-methyl-1H-indol-3-yl)-1-oxopropan-2-yl)-L-asparaginate | HCl | 37 | 4 | 19.9 ± 6 | 25 | 0.18 | 409 ± 72 | 5 | 0.41 |
| NLG-1554 | N$^\alpha$-glycyl-1-methyl-D-tryptophan hydrochloride | HCl | 37 | 4 | 17.5 ± 2 | 10 | 0.35 | 394 ± 103 | 1 | 0.48 |
| NLG-1677 | N$^\alpha$-glycyl-1-methyl-D-tryptophan hydrochloride | H$_3$PO$_4$ | 37 | 4 | 15.4 ± 5 | −3 | 0.45 | 403 ± 153 | 3 | 0.45 |

TABLE 11.1

Comparison of Cmax and total exposure (AUC$_{0->\infty}$) between indoximod free base vs. its prodrugs in different salt forms after oral dosing of cynomolgous monkeys with capsules

| Drug/ Prodrug ID | Name | Salt form | Dose (μmol/ kg) | n | Cmax (μM) | % Change Cmax | p Value | AUC$_{(0->\infty)}$ (μM · h) | % Change in AUC | pValue |
|---|---|---|---|---|---|---|---|---|---|---|
| indoximod | 1-methyl-D-tryptophan | free base | 92 | 3 | 8.2 ± 0.4 | | | 38.5 ± 4 | | |
| indoximod | 1-methyl-D-tryptophan | free base | 275 | 3 | 17.5 ± 3 | | | 74.9 ± 5 | | |
| indoximod | 1-methyl-D-tryptophan | free base | 875 | 3 | 27.8 ± 8 | | | 165 ± 52 | | |
| NLG-1564 | ethyl N$^\alpha$-(L-leucyl)-1-methyl-D-tryptophanate | HCl | 92 | 3 | 50.6 ± 8 | 518 | 0.0004 | 114 ± 2 | 195 | <0.0001 |
| NLG-1564 | ethyl N$^\alpha$-(L-leucyl)-1-methyl-D-tryptophanate | HCl | 275 | 3 | 101 ± 28 | 476 | 0.003 | 463 ± 36 | 518 | <0.0001 |
| NLG-1564 | ethyl N$^\alpha$-(L-leucyl)-1-methyl-D-tryptophanate | HCl | 875 | 2 | 92 ± 17 | 230 | 0.005 | 853 ± 349 | 416 | 0.017 |
| NLG-3272 | ethyl N$^\alpha$-(L-methionyl)-1-methyl-D-tryptophanate | HCl | 92 | 3 | 33 ± 5 | 305 | 0.0005 | 90.7 ± 11 | 136 | 0.0007 |
| NLG-3272 | ethyl N$^\alpha$-(L-methionyl)-1-methyl-D-tryptophanate | HCl | 275 | 3 | 88 ± 32 | 402 | 0.009 | 370 ± 113 | 393 | 0.005 |
| NLG-3272 | ethyl N$^\alpha$-(L-methionyl)-1-methyl-D-tryptophanate | HCl | 875 | 3 | 142 ± 57 | 411 | 0.013 | 761 ± 516 | 369 | 0.059 |

REFERENCES

1. McGaha, T. L., et al., *Amino acid catabolism: a pivotal regulator of innate and adaptive immunity.* Immunol Rev, 2012. 249(1): p. 135-57.
2. Li, L., et al., *Altered tryptophan metabolism as a paradigm for good and bad aspects of immune privilege in chronic inflammatory diseases.* Front Immunol, 2012. 3: p. 109.
3. Munn, D. H., et al., *Prevention of allogeneic fetal rejection by tryptophan catabolism.* science, 1998. 281(5380): p. 1191-3.
4. Muller, A. J., et al., *Inhibition of indoleamine 2,3-dioxygenase, an immunoregulatory target of the cancer suppression gene Bin1, potentiates cancer chemotherapy.* Nat Med, 2005. 11(3): p. 312-9.
5. Peterson, A. C., et al., *Evaluation of functionalized tryptophan derivatives and related compounds as competitive inhibitors of indoleamine 2,3-dioxygenase.* Medicinal Chemistry Research, 1994. 3: p. 531-544.
6. Hou, D. Y., et al., *Inhibition of indoleamine 2,3-dioxygenase in dendritic cells by stereoisomers of 1-methyl-tryptophan correlates with antitumor responses.* Cancer Res, 2007. 67(2): p. 792-801.
7. Metz, R., et al., *IDO inhibits a tryptophan sufficiency signal that stimulates mTOR: A novel IDO effector pathway targeted by D-1-methyl-tryptophan.* Oncoimmunology, 2012. 1(9): p. 1460-1468.
8. Sharma, M. D., et al., *Plasmacytoid dendritic cells from mouse tumor-draining lymph nodes directly activate mature Tregs via indoleamine 2,3-dioxygenase.* J Clin Invest, 2007. 117(9): p. 2570-82.
9. Sharma, M. D., et al., *Indoleamine 2,3-dioxygenase controls conversion of Foxp3+ Tregs to TH17− like cells in tumor-draining lymph nodes.* Blood, 2009.
10. Holmgaard, R. B., et al., *Indoleamine 2,3-dioxygenase is a critical resistance mechanism in antitumor T cell immunotherapy targeting CTLA-4.* J Exp Med, 2013. 210(7): p. 1389-402.
11. Munn, D. H., et al., *GCN2 kinase in T cells mediates proliferative arrest and anergy induction in response to indoleamine 2,3-dioxygenase.* Immunity, 2005. 22(5): p. 633-42.
12. Fallarino, F., et al., *The combined effects of tryptophan starvation and tryptophan catabolites down-regulate T cell receptor zeta-chain and induce a regulatory phenotype in naive T cells.* J Immunol, 2006. 176(11): p. 6752-61.
13. Kumar, S., et al., *Structure based development of phenylimidazole-derived inhibitors of indoleamine 2,3-dioxygenase.* J Med Chem, 2008. 51(16): p. 4968-77.
14. Banerjee, T., et al., *A key in vivo antitumor mechanism of action of natural product-based brassinins is inhibition of indoleamine 2,3-dioxygenase.* Oncogene, 2008. 27(20): p. 2851-7.

We claim:

1. A salt of indoximod according to Formula 1a:

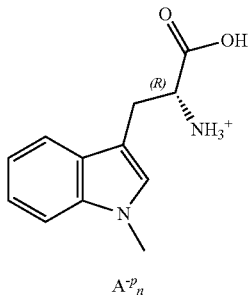

Formula 1a $A^{-p}{}_n$ wherein $A^{-p}{}_n$ is an inorganic or organic anion in an ionization state p, the anion present at a stoichiometric ratio n that ensures molecular charge neutrality.

2. The salt of claim 1, wherein $A^{-p}{}_n$ is an anion selected from the group consisting of chloride, phosphate, sulfate, mesylate, besylate, acetate, ascorbate, aspartate, glutamate, glutarate, lactate, maleate, malonate, oxalate, succinate, fumarate, tartrate and citrate, wherein the ionization state −p is −1, −2 or −3 and the stoichiometric ratio n is 1, ½ or ⅓, respectively, so that it satisfies stoichiometric conditions of charge neutrality.

3. The salt of claim 2, wherein the phosphate is $HPO_4^{-2}$, the $HPO_4^{-2}$ present at a stoichiometric ratio n of 0.5.

4. The salt of claim 2, wherein the phosphate is $HPO_4^{-}$, the $HPO_4^{-}$ present at a stoichiometric ratio n of 1.

5. The salt of claim 1, wherein the anion $A^{-pn}$ is $Cl^{-}$, the $Cl^{-}$ present at a stoichiometric ratio n of 1.

6. The salt of claim 2, wherein the mesylate is $CH_3SO_3^{-}$, the $CH_3SO_3^{-}$ present at a stoichiometric ratio n of 1.

7. A salt of indoximod, according to Formula 1b:

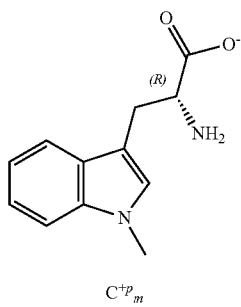

Formula 1b $C^{+p}{}_m$ wherein $C^{+p}{}_m$ is an inorganic cation in an ionization state +p, the cation present at a stoichiometric ratio m that ensures molecular charge neutrality of the salt.

8. The salt of claim 7 wherein $C^{+p}{}_m$ is selected from the group consisting of $Li^+$, $Na^+$, $K^+$, $Mg^{+2}$ and $Ca^{+2}$, wherein when p is +1, m is 1, and when p is +2, m is ½.

9. A prodrug of indoximod, in free base or salt form, according to Formula 2:

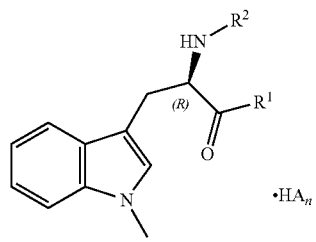

Formula 2

·$HA_n$ wherein:
(a) $R^1$ is —OH, —$OC_{2-3}$alkyl, —$OCH_2CH(OH)CH_2OH$, —$O(CH_2)_2N(CH_3)_2$, —$OC_{1-3}$alkyl-$R^3$, —$NHC^{(S)}HR^4(COOH)$, —$NHC^{(R)}HR^4(COOH)$, —$OC_{1-6}$alkyl$R^6$, —$OC_{1-2}$alkyl-$C^{(S)}H(NH_2)$ (COOH), or —$OC_{1-2}$alkyl-$C^{(R)}H(NH_2)(COOH)$;
(b) $R^2$ is H, —$C(O)C^{(S)}H(NH_2)R^4$, —$C(O)C^{(R)}H(NH_2)R^4$, —$C(O)CH_2C^{(S)}H(NH_2)$, —$C(O)OCH_3$, —$C(O)OR^5$, or —$C(O)NHR^5$;
(c) $R^3$ is tetrahydropyran or

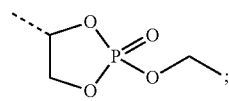

;

(d) $R^4$ is H, —$C_{1-5}$alkyl, —$(CH_2)_{1-2}SH$, $C_{1-5}$alkyl$SC_{1-5}$alkyl, $C_{1-5}$alkyl$OC_{1-5}$alkyl, —$CH_2$—$R^6$, —$CH_2OH$, —$CH(OH)CH_3$, —$(CH_2)_{1-2}C(O)NH_2$, —$(CH_2)_{1-3}C(O)OH$, —$(CH_2)_{1-4}NH_2$, or —$(CH_2)_{1-3}NC(=NH_2)NH_2$;
(e) $C^{(S)}$ and $C^{(R)}$ are carbons with the S or R stereochemistry, respectively, when $R^4$ is not H;
(f) $R^5$ is H, $C_{1-6}$alkyl$R^6$, or $R^6$
(g) $R^6$ is H, aryl, alkylaryl, heteroaryl, cycloalkyl, or heterocycloalkyl, wherein the aryl, alkylaryl, heteroaryl, cycloalkyl or heterocycloalkyl is optionally substituted with one, two or three $R^7$ groups;
(h) each $R^7$ is independently halogen, cyano, nitro, —OR, —$N(R)_2$, —SR, —C(O)OR, $C_{1-6}$alkyl, $C_{1-6}$haloalkyl, —$C(O)N(R)_2$, —C(O)R, —S(O)R, —S(O)OR, —$S(O)N(R)_2$, —$S(O)_2R$, —$S(O)_2OR$, —$S(O)_2N(R)_2$, —OC(O)R, —OC(O)OR, —$OC(O)N(R)_2$, —N(R)C(O)R, —N(R)C(O)OR, or —$N(R)C(O)N(R)_2$, wherein R is H or $C_{1-4}$alkyl;

with the proviso that $R^1$ cannot be —OH when $R^2$ is H, and the compound cannot be $N^\alpha$-tert-butoxycarbonyl-1-methyl-D-tryptophan, ethyl $N^\alpha$-benzyl-1-methyl-D-tryptophanate, or benzyl $N^\alpha$-(tert-butoxycarbonyl)-1-methyl-D-tryptophanate; and $HA_n$ is an acid selected from the group consisting of $PO_4H_3$ (phosphoric acid), $SO_4H_2$ (sulfuric acid), HCl (hydrochloric acid), $HSO_3CH_3$ (methyl sulfonic acid), $C_6H_5SO_3H$ (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid, wherein the stoichiometric ratio n of the acid is 0, 0.5, 1 or 2 such that the prodrug is charge neutral.

10. The prodrug of claim 9, wherein:
(a) $R^1$ is —OH, —$OC_{2-3}$alkyl, —$OCH_2CH(OH)CH_2OH$, —$O(CH_2)_2N(CH_3)_2$, or —$OC_{1-3}$alkyl-$R^3$;
(b) $R^2$ is H or —$C(O)C^{(S)}H(NH_2)R^4$, (c) R³ is tetrahydropyran, or

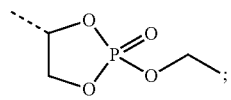

(d) R⁴ is H, —C₁₋₅alkyl, —(CH₂)₁₋₂SH, —(CH₂)₁₋₃SCH₃, —(CH₂)₁₋₃OCH₃—CH₂—R⁶, —CH₂OH, —CH(OH)CH₃, —(CH₂)₁₋₂C(O)NH₂, —(CH₂)₁₋₃C(O)OH, —(CH₂)₁₋₄NH₂, or —(CH₂)₁₋₃NC(=NH₂)NH₂;
(e) C$^{(S)}$ is a carbon with the S stereochemistry, when R⁴ is not H;
(f) R⁶ is H, aryl, alkylaryl, heteroaryl, cycloalkyl, or heterocycloalkyl, wherein the aryl, alkylaryl, heteroaryl, cycloalkyl or heterocycloalkyl is optionally substituted with one two or three R⁷ groups;
(g) each R⁷ is independently halogen, cyano, nitro, —OR, —N(R)₂, —SR, —C(O)OR, C₁₋₆alkyl, C₁₋₆haloalkyl, —C(O)N(R)₂, —C(O)R, —S(O)R, —S(O)OR, —S(O)N(R)₂, —S(O)₂R, —S(O)₂OR, —S(O)₂N(R)₂, —OC(O)R, —OC(O)OR, —OC(O)N(R)₂, —N(R)C(O)R, —N(R)C(O)OR, or —N(R)C(O)N(R)₂, wherein R is H or C₁₋₄alkyl;
with the proviso that R¹ cannot be —OH when R² is H; and
HA$_n$ is an acid selected from the group consisting of PO₄H₃ (phosphoric acid), SO₄H₂ (sulfuric acid), HCl (hydrochloric acid), HSO₃CH₃ (methyl sulfonic acid), C₆H₅SO₃H (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid, wherein the stoichiometric ratio n is 0, 0.5, 1 or 2 such that the prodrug is charge neutral.

11. The prodrug of claim 9, wherein:
(a) R¹ is —OH, —OC₂₋₃alkyl, —OCH₂CH(OH)CH₂OH, —O(CH₂)₂N(CH₃)₂, or —OC₁₋₃alkyl-R³;
(b) R² is H or —C(O)C$^{(S)}$H(NH₂)R⁴;
(c) R³ is tetrahydropyran, or

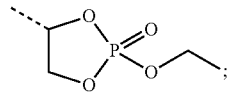

(d) R⁴ is H, —C₁₋₅alkyl, —(CH₂)₂SCH₃, —CH₂—R⁶, —(CH₂)₁₋₂C(O)NH₂, —(CH₂)₁₋₃C(O)OH, or —(CH₂)₁₋₄NH₂;
(e) C$^{(S)}$ is a carbon with the S stereochemistry, when R⁴ is not H;
(f) R⁶ is H, aryl, alkylaryl, or heteroaryl, wherein the aryl, alkylaryl or heteroaryl is optionally substituted with one R⁷ group;
(g) each R⁷ is independently halogen, cyano, nitro, —OR, —N(R)₂, —SR, —C(O)OR, —C₁₋₆alkyl, C₁₋₆haloalkyl, —C(O)N(R)₂, —C(O)R, —S(O)R, —S(O)OR, —S(O)N(R)₂, —S(O)₂R, —S(O)₂OR, —S(O)₂N(R)₂, —OC(O)R, —OC(O)OR, —OC(O)N(R)₂, —N(R)C(O)R, —N(R)C(O)OR, or —N(R)C(O)N(R)₂, wherein R is H or C₁₋₄alkyl;
with the proviso that R¹ cannot be —OH when R² is H;
HA$_n$ is an acid selected from the group of PO₄H₃ (phosphoric acid), SO₄H₂ (sulfuric acid), HCl (hydrochloric acid), HSO₃CH₃ (methyl sulfonic acid), C₆H₅SO₃H (benzyl sulfonic acid), wherein the stoichiometric ratio n of the acid is 0, 0.5, 1 or 2 such that the prodrug is charge neutral.

12. The prodrug of claim 9, wherein
(a) R¹ is —OH, —OC₂₋₃alkyl, —OCH₂CH(OH)CH₂OH, —O(CH₂)₂N(CH₃)₂, or —OC₁₋₃alkyl-R³;
(b) R² is H or —C(O)C$^{(S)}$H(NH₂)R⁴;
(c) R³ is tetrahydropyran, or

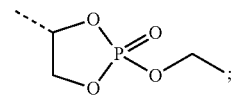

(d) R⁴ is —CH₂CH(CH₃)₂, —(CH₂)₂SCH₃, —C$^{(S)}$H(CH₃)CH₂CH₃, —CH₂—R⁶, —(CH₂)₂C(O)NH₂, —(CH₂)₃C(O)OH, or —(CH₂)₄NH₂;
(e) C$^{(S)}$ is a carbon with the S stereochemistry;
(f) R⁶ is phenyl;
with the proviso that R¹ cannot be —OH when R² is H;
HA$_n$ is an acid selected from the group of PO₄H₃ (phosphoric acid), SO₄H₂ (sulfuric acid), HCl (hydrochloric acid), HSO₃CH₃ (methyl sulfonic acid), C₆H₅SO₃H (benzyl sulfonic acid), and wherein the stoichiometric ratio n of the acid is 0, 0.5, 1 or 2 such that the prodrug is charge neutral.

13. The prodrug of claim 9, wherein:
(a) R¹ is —OC₂₋₃alkyl or —OCH₂CH(OH)CH₂OH;
(b) R² is H or —C(O)C$^{(S)}$H(NH₂)R⁴;
(c) R⁴ is —CH₂CH(CH₃)₂, —(CH₂)₂SCH₃ or —(CH₂)₂C(O)NH₂;
(d) C$^{(S)}$ is a carbon with the S stereochemistry;
with the proviso that R¹ cannot be —OH when R² is H;
HA$_n$ is an acid selected from the group of PO₄H₃ (phosphoric acid), SO₄H₂ (sulfuric acid), HCl (hydrochloric acid), HSO₃CH₃ (methyl sulfonic acid) or C₆H₅SO₃H (benzyl sulfonic acid); and wherein the stoichiometric ratio n of the acid is of 0, 0.5, 1 or 2 such that the prodrug is charge neutral.

14. A prodrug comprising one of the following compounds:
ethyl N$^α$-(L-leucyl)-1-methyl-D-tryptophanate;
ethyl N$^α$-(L-methionyl)-1-methyl-D-tryptophanate;
2,3-dihydroxypropyl 1-methyl-D-tryptophanate;
N$^α$-(L-leucyl)-1-methyl-D-tryptophan;
N$^α$-(L-methionyl)-1-methyl-D-tryptophan;
ethyl N$^α$-(L-isoleucyl)-1-methyl-D-tryptophanate;
N$^α$-(L-glycyl)-1-methyl-D-tryptophan;
(S)-5-amino-6-(((R)-1-carboxy-2-(1-methyl-1H-indol-3-yl)ethyl)amino)-6-oxohexanoic acid;
N$^α$-(L-lysyl)-1-methyl-D-tryptophan;
N$^α$-(L-phenylalanyl)-1-methyl-D-tryptophan;
ethyl N$^α$-(L-glutaminyl)-1-methyl-D-tryptophanate;
2-(dimethylamino)ethyl 1-methyl-D-tryptophanate;
(2-ethoxy-2-oxido-1,3,2-dioxaphospholan-4-yl)methyl 1-methyl-D-tryptophanate;
2-(tetrahydro-2H-pyran-4-yl)ethyl 1-methyl-D-tryptophanate;
ethyl 1-methyl-D-tryptophanate; or
isopropyl 1-methyl-D-tryptophanate.

15. A pharmaceutical composition of indoximod according to Formula 1a:

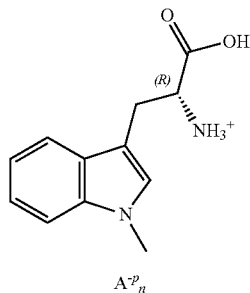

Formula 1a wherein $A^{-p}_n$ is an inorganic or organic anion in an ionization state –p, the anion present at a stoichiometric ratio n that ensures molecular charge neutrality.

16. The pharmaceutical composition of claim 15, wherein $A^{-p}_n$ is an anion selected from the group consisting of chloride, phosphate, sulfate, mesylate, besylate, acetate, ascorbate, aspartate, glutamate, glutarate, lactate, maleate, malonate, oxalate, succinate, fumarate, tartrate and citrate, wherein the ionization state p is –1, –2 or –3 and the stoichiometric ratio n is 1, ½ or ⅓, respectively, so that it satisfies stoichiometric conditions of charge neutrality.

17. The pharmaceutical composition of claim 16, wherein the phosphate is $HPO_4^{-2}$, the $HPO_4^{-2}$ present at a stoichiometric ratio n of 0.5.

18. The pharmaceutical composition of claim 16, wherein the phosphate is $HPO_4^-$, the $HPO_4^-$ present at a stoichiometric ratio n of 1.

19. The pharmaceutical composition of claim 15, wherein the anion $A^{-pn}$ is $Cl^-$, the $Cl^-$ present at a stoichiometric ratio n of 1.

20. The pharmaceutical composition of claim 16, wherein the mesylate is $CH_3SO_3^-$, the $CH_3SO_3^-$ present at a stoichiometric ratio n of 1.

21. A pharmaceutical composition of indoximod, according to Formula 1b:

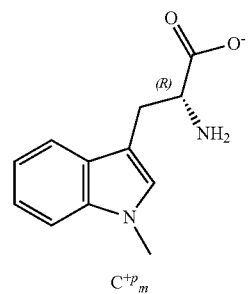

Formula 1b wherein $C^{+p}_m$ is a cation in an ionization state +p, the cation present at a stoichiometric ratio m that ensures molecular charge neutrality of the salt.

22. The pharmaceutical composition of claim 21 wherein $C^{+p}_m$ is selected from the group consisting of $Li^+$, $Na^+$, $K^+$, $Mg^{+2}$ and $Ca^{+2}$, wherein when p is +1, m is 1, and when p is +2, m is ½.

23. A pharmaceutical composition of indoximod, in free base or salt form, according to Formula 2:

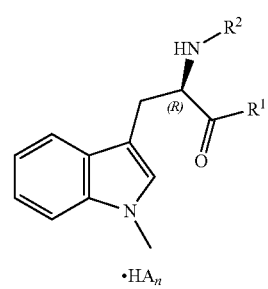

Formula 2 wherein:
(a) $R^1$ is —OH, —$OC_{2-3}$alkyl, —$OCH_2CH(OH)CH_2OH$, —$O(CH_2)_2N(CH_3)_2$, —$OC_{1-3}$alkyl-$R^3$, —$NHC^{(S)}HR^4(COOH)$, —$NHC^{(R)}HR^4(COOH)$, —$OC_{1-6}$alkyl$R^6$, —$OC_{1-2}$alkyl, —$C^{(S)}H(NH_2)$ (COOH), or —$OC_{1-2}$alkyl-$C^{(R)}H(NH_2)$(COOH);
(b) $R^2$ is H, —$C(O)C^{(S)}H(NH_2)R^4$, —$C(O)C^{(R)}H(NH_2)R^4$, —$C(O)CH_2C(S)H(NH_2)$, —$C(O)OCH_3$, —$C(O)OR^5$, or —$C(O)NHR^5$;
(c) $R^3$ is tetrahydropyran or

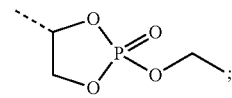

;

(d) $R^4$ is H, —$C_{1-5}$alkyl, —$(CH_2)_{1-2}SH$, $C_{1-5}$alkyl$SC_{1-5}$alkyl, $C_{1-5}$alkyl$OC_{1-5}$alkyl, —$CH_2$—$R^6$, —$CH_2OH$, —$CH(OH)CH_3$, —$(CH_2)_{1-2}C(O)NH_2$, —$(CH_2)_{1-3}C(O)OH$, —$(CH_2)_{1-4}NH_2$, or —$(CH_2)_{1-3}NC(=NH_2)NH_2$;
(e) $C^{(S)}$ and $C^{(R)}$ are carbons with the S or R stereochemistry, respectively, when $R^4$ is not H;
(f) $R^5$ is H, $C_{1-6}$alkyl$R^6$, or $R^6$
(g) $R^6$ is H, aryl, alkylaryl, heteroaryl, cycloalkyl, or heterocycloalkyl, wherein the aryl, alkylaryl, heteroaryl, cycloalkyl or heterocycloalkyl is optionally substituted with one two or three $R^7$ groups;
(h) each $R^7$ is independently halogen, cyano, nitro, —OR, —$N(R)_2$, —SR, —$C(O)OR$, $C_{1-6}$alkyl, $C_{1-6}$haloalkyl, —$C(O)N(R)_2$, —$C(O)R$, —$S(O)R$, —$S(O)OR$, —$S(O)N(R)_2$, —$S(O)_2R$, —$S(O)_2OR$, —$S(O)_2N(R)_2$, —$OC(O)R$, —$OC(O)OR$, —$OC(O)N(R)_2$, —$N(R)C(O)R$, —$N(R)C(O)OR$, or —$N(R)C(O)N(R)_2$, wherein R is H or $C_{1-4}$alkyl;
with the proviso that $R^1$ cannot be —OH when $R^2$ is H, and the compound cannot be $N^\alpha$-tert-butoxycarbonyl-1-methyl-D-tryptophan, ethyl $N^\alpha$-benzyl-1-methyl-D-tryptophanate, or benzyl $N^\alpha$-(tert-butoxycarbonyl)-1-methyl-D-tryptophanate; and
$HA_n$ is an acid selected from the group consisting of $PO_4H_3$ (phosphoric acid), $SO_4H_2$ (sulfuric acid), HCl (hydrochloric acid), $HSO_3CH_3$ (methyl sulfonic acid), $C_6H_5SO_3H$ (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid, wherein the stoichiometric ratio n of the acid is 0, 0.5, 1 or 2 such that the prodrug is charge neutral.

24. The pharmaceutical composition of claim 23, wherein:
(a) $R^1$ is —OH, —OC$_{2-3}$alkyl, —OCH$_2$CH(OH)CH$_2$OH, —O(CH$_2$)$_2$N(CH$_3$)$_2$, or —OC$_{1-3}$alkyl-R$^3$;
(b) $R^2$ is H or —C(O)C$^{(S)}$H(NH$_2$)R$^4$,
(c) $R^3$ is tetrahydropyran, or

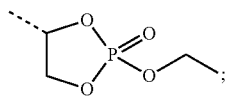

(d) $R^4$ is H, —C$_{1-5}$alkyl, —(CH$_2$)$_{1-2}$SH, —(CH$_2$)$_{1-3}$SCH$_3$, —(CH$_2$)$_{1-3}$OCH$_3$, —CH$_2$—R$^6$, —CH$_2$OH, —CH(OH)CH$_3$, —(CH$_2$)$_{1-2}$C(O)NH$_2$, —(CH$_2$)$_{1-3}$C(O)OH, —(CH$_2$)$_{1-4}$NH$_2$, or —(CH$_2$)$_{1-3}$NC(=NH$_2$)NH$_2$;
(e) C$^{(S)}$ is a carbon with the S stereochemistry, when R$^4$ is not H;
(f) R$^6$ is H, aryl, alkylaryl, heteroaryl, cycloalkyl, or heterocycloalkyl, wherein the aryl, alkylaryl, heteroaryl, cycloalkyl or heterocycloalkyl is optionally substituted with one two or three R$^7$ groups;
(g) each R$^7$ is independently halogen, cyano, nitro, —OR, —N(R)$_2$, —SR, —C(O)OR, C$_{1-6}$alkyl, C$_{1-6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, or —N(R)C(O)N(R)$_2$, wherein R is H or C$_{1-4}$alkyl;
with the proviso that R$^1$ cannot be —OH when R$^2$ is H; and
HA$_n$ is an acid selected from the group consisting of PO$_4$H$_3$ (phosphoric acid), SO$_4$H$_2$ (sulfuric acid), HCl (hydrochloric acid), HSO$_3$CH$_3$ (methyl sulfonic acid), C$_6$H$_5$SO$_3$H (benzyl sulfonic acid), acetic acid, ascorbic acid, aspartic acid, glutamic acid, glutaric acid, lactic acid, maleic acid, malonic acid, oxalic acid, succinic acid, fumaric acid, tartaric acid and citric acid, wherein the stoichiometric ratio n is 0, 0.5, 1 or 2 such that the prodrug is charge neutral.

25. The pharmaceutical composition of claim 23, wherein:
(a) $R^1$ is —OH, —OC$_{2-3}$alkyl, —OCH$_2$CH(OH)CH$_2$OH, —O(CH$_2$)$_2$N(CH$_3$)$_2$, or —OC$_{1-3}$alkyl-R$^3$;
(b) $R^2$ is H or —C(O)C$^{(S)}$H(NH$_2$)R$^4$;
(c) $R^3$ is tetrahydropyran, or

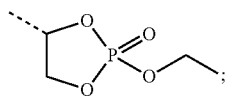

(d) $R^4$ is H, —C$_{1-5}$alkyl, —(CH$_2$)$_2$SCH$_3$, —CH$_2$—R$^6$, —(CH$_2$)$_{1-2}$C(O)NH$_2$, —(CH$_2$)$_{1-3}$C(O)OH, or —(CH$_2$)$_{1-4}$NH$_2$;
(e) C$^{(S)}$ is a carbon with the S stereochemistry, when R$^4$ is not H;
(f) R$^6$ is H, aryl, alkylaryl, or heteroaryl, wherein the aryl, alkylaryl or heteroaryl is optionally substituted with one R$^7$ group;
(g) each R$^7$ is independently halogen, cyano, nitro, —OR, —N(R)$_2$, —SR, —C(O)OR, —C$_{1-6}$alkyl, C$_{1-6}$haloalkyl, —C(O)N(R)$_2$, —C(O)R, —S(O)R, —S(O)OR, —S(O)N(R)$_2$, —S(O)$_2$R, —S(O)$_2$OR, —S(O)$_2$N(R)$_2$, —OC(O)R, —OC(O)OR, —OC(O)N(R)$_2$, —N(R)C(O)R, —N(R)C(O)OR, and —N(R)C(O)N(R)$_2$, wherein R is H or C$_{1-4}$alkyl;
with the proviso that R$^1$ cannot be —OH when R$^2$ is H;
HA$_n$ is an acid selected from the group consisting of PO$_4$H$_3$ (phosphoric acid), SO$_4$H$_2$ (sulfuric acid), HCl (hydrochloric acid), HSO$_3$CH$_3$ (methyl sulfonic acid), and C$_6$H$_5$SO$_3$H (benzyl sulfonic acid), wherein the stoichiometric ratio n of the acid is 0, 0.5, 1 or 2 such that the prodrug is charge neutral.

26. The pharmaceutical composition of claim 23, wherein:
(a) $R^1$ is —OH, —OC$_{2-3}$alkyl, —OCH$_2$CH(OH)CH$_2$OH, —O(CH$_2$)$_2$N(CH$_3$)$_2$, or —OC$_{1-3}$alkyl-R$^3$;
(b) $R^2$ is H or —C(O)C$^{(S)}$H(NH$_2$)R$^4$;
(c) $R^3$ is tetrahydropyran, or

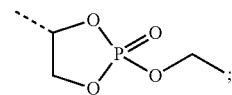

(d) $R^4$ is —CH$_2$CH(CH$_3$)$_2$, —(CH$_2$)$_2$SCH$_3$, —C$^{(S)}$H(CH$_3$)CH$_2$CH$_3$, —CH$_2$—R$^6$, —(CH$_2$)$_2$C(O)NH$_2$, —(CH$_2$)$_3$C(O)OH, or —(CH$_2$)$_4$NH$_2$;
(e) C$^{(S)}$ is a carbon with the S stereochemistry;
(f) R$^6$ is phenyl;
with the proviso that R$^1$ cannot be —OH when R$^2$ is H;
HA$_n$ is an acid selected from the group consisting of PO$_4$H$_3$ (phosphoric acid), SO$_4$H$_2$ (sulfuric acid), HCl (hydrochloric acid), HSO$_3$CH$_3$ (methyl sulfonic acid), and C$_6$H$_5$SO$_3$H (benzyl sulfonic acid), and wherein the stoichiometric ratio n of the acid is 0, 0.5, 1 or 2 such that the prodrug is charge neutral.

27. The pharmaceutical composition of claim 23, wherein:
(e) $R^1$ is —OC$_{2-3}$alkyl or —OCH$_2$CH(OH)CH$_2$OH;
(f) $R^2$ is H or —C(O)C$^{(S)}$H(NH$_2$)R$^4$;
(g) $R^4$ is —CH$_2$CH(CH$_3$)$_2$, —(CH$_2$)$_2$SCH$_3$, or —(CH$_2$)$_2$C(O)NH$_2$;
(h) C$^{(S)}$ is a carbon with the S stereochemistry;
with the proviso that R$^1$ cannot be —OH when R$^2$ is H, HA$_n$ is an acid selected from the group of PO$_4$H$_3$ (phosphoric acid), SO$_4$H$_2$ (sulfuric acid), HCl (hydrochloric acid), HSO$_3$CH$_3$ (methyl sulfonic acid) or C$_6$H$_5$SO$_3$H (benzyl sulfonic acid); and wherein the stoichiometric ratio n of the acid is of 0, 0.5, 1 or 2 such that the prodrug is charge neutral.

28. A pharmaceutical composition comprising one of the following compounds:
ethyl N$^\alpha$-(L-leucyl)-1-methyl-D-tryptophanate;
ethyl N$^\alpha$-(L-methionyl)-1-methyl-D-tryptophanate;
2,3-dihydroxypropyl 1-methyl-D-tryptophanate;
N$^\alpha$-(L-leucyl)-1-methyl-D-tryptophan;
N$^\alpha$-(L-methionyl)-1-methyl-D-tryptophan;
ethyl N$^\alpha$-(L-isoleucyl)-1-methyl-D-tryptophanate;
N$^\alpha$-(L-glycyl)-1-methyl-D-tryptophan;
(S)-5-amino-6-(((R)-1-carboxy-2-(1-methyl-1H-indol-3-yl)ethyl)amino)-6-oxohexanoic acid;
N$^\alpha$-(L-lysyl)-1-methyl-D-tryptophan;
N$^\alpha$-(L-phenylalanyl)-1-methyl-D-tryptophan;
ethyl N$^\alpha$-(L-glutaminyl)-1-methyl-D-tryptophanate;
2-(dimethylamino)ethyl 1-methyl-D-tryptophanate;
(2-ethoxy-2-oxido-1,3,2-dioxaphospholan-4-yl)methyl 1-methyl-D-tryptophanate;

2-(tetrahydro-2H-pyran-4-yl)ethyl 1-methyl-D-tryptophanate;
ethyl 1-methyl-D-tryptophanate; or
isopropyl 1-methyl-D-tryptophanate.

29. The pharmaceutical composition of any of claims 15-28, wherein the composition is a solid capsule, tablet or pill.

30. The pharmaceutical composition of any of claims 15-28, wherein the composition is a dissolvable capsule.

* * * * *

UNITED STATES PATENT AND TRADEMARK OFFICE
CERTIFICATE OF CORRECTION

PATENT NO. : 9,732,035 B2
APPLICATION NO. : 15/171031
DATED : August 15, 2017
INVENTOR(S) : Mario Mautino et al.

Page 1 of 1

It is certified that error appears in the above-identified patent and that said Letters Patent is hereby corrected as shown below:

At Claim 1, Column 125, Line 20, please replace "ionization state p" with "ionization state -p".

At Claim 23, Column 130, between Lines 22 and 23, please replace "-$OC_{1-2}$alkyl, -$C^{(S)}H(NH_2)(COOH)$" with "-$OC_{1-2}$alkyl-$C^{(S)}H(NH_2)(COOH)$".

At Claim 23, Column 130, Line 25, please replace "-$C(O)CH_2C(S)H(NH_2)$" with "-$C(O)CH_2C^{(S)}H(NH_2)$".

Signed and Sealed this
Eighteenth Day of September, 2018

Andrei Iancu
*Director of the United States Patent and Trademark Office*